(12) United States Patent
Kira et al.

(10) Patent No.: US 7,524,847 B2
(45) Date of Patent: Apr. 28, 2009

(54) FUSED 1,3-DIHYDRO-IMIDAZOLE RING COMPOUNDS

(75) Inventors: Kazunobu Kira, Tsukuba (JP); Richard Clark, Tsuchiura (JP); Seiji Yoshikawa, Kashima-gun (JP); Taisuke Uehara, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 463 days.

(21) Appl. No.: 10/537,227

(22) PCT Filed: Dec. 2, 2003

(86) PCT No.: PCT/JP03/15402

§ 371 (c)(1),
(2), (4) Date: Dec. 27, 2005

(87) PCT Pub. No.: WO2004/050656

PCT Pub. Date: Jun. 17, 2004

(65) Prior Publication Data

US 2006/0111362 A1  May 25, 2006

(30) Foreign Application Priority Data

Dec. 4, 2002 (JP) ............................. 2002-352186

(51) Int. Cl.
| | |
|---|---|
| C07D 473/40 | (2006.01) |
| C07D 473/34 | (2006.01) |
| C07D 473/18 | (2006.01) |
| A61K 31/52 | (2006.01) |
| A61K 31/522 | (2006.01) |
| C07D 471/04 | (2006.01) |
| A61P 3/10 | (2006.01) |
| A61P 3/06 | (2006.01) |
| A61P 3/04 | (2006.01) |

(52) U.S. Cl. ................... 514/252.16; 514/263.22; 544/276; 544/277; 546/118

(58) Field of Classification Search ........... 544/276, 544/277; 514/263.2, 263.22, 252.16
See application file for complete search history.

(56) References Cited

U.S. PATENT DOCUMENTS

| | | | | |
|---|---|---|---|---|
| 5,057,517 A | * | 10/1991 | Johnston et al. | ........ 514/252.16 |
| 7,122,665 B2 | * | 10/2006 | Sun et al. | ................... 544/118 |
| 2004/0082570 A1 | | 4/2004 | Yoshikawa et al. | |
| 2004/0116328 A1 | | 6/2004 | Yoshikawa et al. | |
| 2005/0215573 A1 | * | 9/2005 | Schilling et al. | ......... 514/266.2 |

FOREIGN PATENT DOCUMENTS

| | | |
|---|---|---|
| AU | 200029414 B2 | 1/2003 |
| EP | 0300726 A1 | 1/1989 |
| EP | 1 338 595 A2 | 8/2003 |
| JP | 2000-86663 A | 3/2000 |
| JP | 2001-151777 A | 6/2001 |
| WO | WO 03/104229 A1 | 12/2003 |
| WO | WO 2004/028524 A1 | 4/2004 |
| WO | WO 2005/044793 A2 | 5/2005 |

OTHER PUBLICATIONS

Patient Information JANUVIA™ <http://www.merck.com/product/usa/pi_circulars/j/januvia/januvia_ppi.pdf> downloaded from the internet Apr. 30, 2008.*
CAPLUS Database accession No. 1972:488447; abstract of: Korsunskii, V., et al., "Syntheses of purines XXIX. 8- and 2-[bis(aziridino)-phosphinamido]purines," 1992, *Khimiko-Farmatsevticheskii Zhurnal*, vol. 6(6), pp. 28-31.
Kira, Kazunobu et al.; "Development of a novel inhibitor of DPP-IV using a byproduct as the lead compound"; *National Meeting & Exposition Program: 228th National Meeting*; Aug. 22-26, 2004; Abstract 262; American Chemical Society; Philadelphia, PA.
Kira, Kazunobu et al.; "Development of a novel inhibitor of DPP-IV using a byproduct as the lead compound"; *Yakku Zasshi: Journal of the Pharmaceutical Society of Japan: The 23rd Medicinal Chemistry Symposium; The 12th Annual Meeting of Division of Medicinal Chemistry* (Tsukuba): Nov. 24-26, 2004; poster 2P-10; pp. 1-13; The Pharmaceutical Society of Japan, Division of Medicinal Chemistry.

* cited by examiner

*Primary Examiner*—Mark L Berch
(74) *Attorney, Agent, or Firm*—Townsend and Townsend and Crew LLP

(57) ABSTRACT

The objective of this invention is to provide novel compounds that show excellent DPPIV-inhibiting activity. The present invention provides compounds represented by the general formula (I), salts thereof, or hydrates thereof,

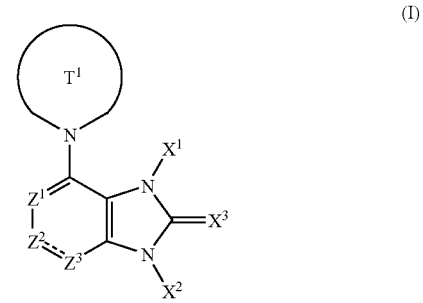

(I)

[wherein,
$T^1$ stands for a monocyclic or bicyclic 4 to 12-membered heterocycle having 1 or 2 nitrogen atoms in the ring, which may have substituents; in formula (I), the following formula

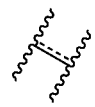

represents a double bond or a single bond; $X^3$ denotes an oxygen atom or a sulfur atom; $X^1$ denotes a $C_{2-6}$ alkyl group which may have substituents; $Z^1$ denotes a nitrogen atom or the formula $-CR^3=$; $Z^2$ and $Z^3$ each independently denote a nitrogen atom, the formula $-CR^1=$, a carbonyl group, or the formula $-NR^2-$; $R^1$, $R^2$, $R^3$, and $X^2$ each independently denote a $C_{1-6}$ alkyl group which may have substituents, and such].

8 Claims, No Drawings

FUSED 1,3-DIHYDRO-IMIDAZOLE RING COMPOUNDS

TECHNICAL FIELD

The present invention relates to novel compounds having DPPIV-inhibiting activities, and particularly relates to fused 1,3-dihydro-imidazole ring compounds that are useful as DPPIV inhibitors.

BACKGROUND ART

Dipeptidyl peptidase-IV (DPPIV) is a kind of serine protease that specifically hydrolyzes the dipeptide-X-Pro (X may be any amino acid) from the free N terminus of a polypeptide chain.

Glucose-dependent insulinotropic hormone (incretin; GLP-1, Glucagon-Like Peptide-1 and GIP; Glucose-dependent Insulinotropic Polypeptide), which is secreted postprandially from the intestinal tract, is quickly degraded and inactivated by this DPPIV Suppressing this degradation of GLP-1 by DPPIV enhances the action of incretin (GLP-1 and GIP), and facilitates insulin secretion from pancreatic β-cells due to glucose stimulus. It has been shown that, as a result, postchallenge hyperglycemia is improved in oral glucose tolerance tests (see Non-patent document 1). Furthermore, it has also been shown that GLP-1 is involved in suppressive effects on appetite and food intake, and also in β cell protection based on its promotional effect on pancreatic β cell differentiation and growth.

Therefore, DPPIV inhibitors can be expected to serve as useful therapeutic and preventive agents against diseases involving GLP-1 and GIP, such as obesity and diabetes.

As shown below, a relationship has been reported between various diseases, including diabetes, and DPPIV DPPIV inhibitors can therefore be expected to become therapeutic agents for such diseases.

(1) Preventive and therapeutic agents for AIDS (see Non-patent document 2), (2) preventive and therapeutic agents for osteoporosis (see Non-patent document 3), (3) preventive and therapeutic agents for intestinal disorders (see Non-patent document 4), (4) preventive and therapeutic agents for hyperlipidemia, diabetes, and obesity, (see Non-patent documents 5 and 6), (5) preventive and therapeutic agents for angiogenesis (see Non-patent document 7), (6) preventive and therapeutic agents for infertility (see Patent document 1), (7) preventive and therapeutic agents for inflammatory diseases, autoimmune diseases, and chronic rheumatoid arthritis (see Non-patent document 8), and (8) preventive and therapeutic agents for cancer (see Non-patent documents 9 and 10), (9) preventive and therapeutic agents for multiple sclerosis (see Non-patent document 11)

Although a number of DPPIV inhibitors are known (see Patent documents 2-11), DPPIV inhibitors comprising a fused 1,3-dihydroimidazole ring are not known.

[Non-patent document 1]

Diabetologia 1999 November, 42(11): 1324-31

[Non-patent document 2]

Science 1993, 262: 2045-2050

[Non-patent document 3]

Clinical chemistry 1988, 34: 2499-2501

[Non-patent document 4]

Endocrinology 2000, 141: 4013-4020

[Non-patent document 5]

Diabetes 1998, 47: 1663-1670,

[Non-patent document 6]

Life Sci 2000, 66(2): 91-103

[Non-patent document 7]

Agents and actions 1991, 32: 125-127

[Non-patent document 8]

The Journal of Immunology 2001, 166: 2041-2048

[Non-patent document 9]

Br J Cancer 1999 March, 79(7-8): 1042-8

[Non-patent document 10]

J Androl 2000 March-April, 21(2): 220-6

[Non-patent document 11]

The Journal of Immunology 2001, 166: 2041-48

[Patent document 1]

WO 00/56296

[Patent document 2]

US Patent Application No. 2001020006

[Patent document 3]

U.S. Pat. No. 6,303,661

[Patent document 4]

U.S. Pat. No. 6,011,155

[Patent document 5]

U.S. Pat. No. 5,543,396

[Patent document 6]

WO 02/02560

[Patent document 7]

WO 00/34241

[Patent document 8]

WO 99/61431

[Patent document 9]

WO 99/67279

[Patent document 10]

WO 97/40832

[Patent document 11]

WO 95/29691

[Patent document 12]

WO 02/068420

As described above, compounds with DPPIV-inhibiting activity useful as pharmaceutical agents are being earnestly sought. However, a compound with excellent DPPIV-inhibiting activity, which is also very useful as a clinically effective pharmaceutical, has yet to be discovered. Thus, an objective of the present invention is to search for and find compounds with DPPIV-inhibiting activity that can be used as preventive or therapeutic agents for the above-mentioned diseases (particularly diabetes and such).

DISCLOSURE OF THE INVENTION

As a result of earnest investigations to achieve the above-mentioned objective, the present inventors succeeded in synthesizing novel fused 1,3-dihydro-imidazole ring compounds, discovering that these compounds have excellent DPPIV-inhibiting activities, and thus accomplishing this invention.

That is to say, the present invention comprises:

(1) a compound represented by the general formula (I), or a salt or a hydrate thereof,

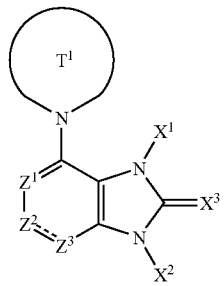

(I)

[wherein, $T^1$ stands for a monocyclic or bicyclic 4 to 12-membered heterocycle containing 1 or 2 nitrogen atoms in the ring, which may have substituents;

$X^3$ denotes an oxygen atom, sulfur atom, or a group of the formula

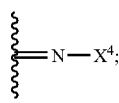

$X^4$ denotes a hydrogen atom, a $C_{1-6}$ alkyl group which may have substitutents, a $C_{3-8}$ cycloalkyl group which may have substitutents, or a $C_{6-10}$ aryl $C_{1-6}$ alkyl group which may have substitutents;

$X^1$ denotes a $C_{1-6}$ alkyl group which may have substitutents, a $C_{2-6}$ alkenyl group which may have substitutents, a $C_{2-6}$ alkynyl group which may have substitutents, a $C_{6-10}$ aryl group which may have substitutents, a 5 to 10-membered heteroaryl group which may have substitutents, a $C_{6-10}$ aryl $C_{1-6}$ alkyl group which may have substitutents, or a 5 to 10-membered heteroaryl $C_{1-6}$ alkyl group which may have substitutents;

$Z^1$ denotes a nitrogen atom, or a group of the formula —$CR^3$=;

$Z^2$ and $Z^3$ each independently denote a nitrogen atom, a group of the formula —$CR^1$=, a carbonyl group, or a group of the formula —$NR^2$—;

in formula (I), the following formula

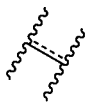

denotes a double bond or a single bond;

in formula (I), when the following formula

denotes a double bond, $Z^2$ and $Z^3$ each independently denote a nitrogen atom or a group of the formula —$CR^1$=;

$R^1$, $R^2$, $R^3$, and $X^2$ each independently denote a hydrogen atom, a 4 to 8-membered heterocyclic group which may have substitutents, or a group represented by the formula —$A^0$—$A^1$—$A^2$;

$A^0$ denotes a single bond, or a $C_{1-6}$ alkylene group that may have 1 to 3 substituents selected from the following substituent group A;

$A^1$ denotes a single bond, oxygen atom, sulfur atom, a sulfinyl group, a sulfonyl group, a carbonyl group, a group of the formula —O—CO, a group of the formula —CO—O—, a group of the formula —$NR^A$—, a group of the formula —CO—$NR^A$—, a group of the formula $NR^A$—CO—, a group of the formula —$SO_2$—$NR^A$—, or a group of the formula —$NR^A$—$SO_2$—;

$A^2$ and $R^A$ each independently denote a hydrogen atom, a cyano group, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5 to 10-membered heteroaryl group, a 4 to 8-membered heterocyclic group, or a $C_{6-10}$ aryl $C_{1-6}$ alkyl group;

however, $A^2$ and $R^A$ each independently may have 1 to 3 substituents selected from the substituent group A described below:

<Substituent Group A> substituent group A refers to a group consisting of: a hydroxyl group, a mercapto group, a cyano group, a halogen atom, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5 to 10-membered heteroaryl group, a 4 to 8-membered heterocyclic group, a $C_{1-6}$ alkoxy group, a $C_{1-6}$ alkylthio group, a group of the formula —$NR^{B4}$—$R^{B5}$ (where $R^{B4}$ and $R^{B5}$ denote hydrogen atoms or $C_{1-6}$ alkyl groups), a group of the formula —CO—$R^{B6}$ (where $R^{B6}$ denotes a 1-pyrrolidinyl group, a 1-morpholinyl group, a 1-piperazinyl group, or a 1-piperidyl group), and a group of the formula —CO—$R^B$—$R^{B2}$ (where $R^B$ denotes a single bond, an oxygen atom, or a group represented by the formula —$NR^{B3}$—; $R^{B2}$ and $R^{B3}$ each independently denote a hydrogen atom, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5 to 10-membered heteroaryl group, a $C_{6-10}$ aryl $C_{1-6}$ alkyl group, or a 5 to 10-membered heteroaryl $C_{1-6}$ alkyl group)];

(2) a compound represented by the general formula (II), or a salt or a hydrate thereof,

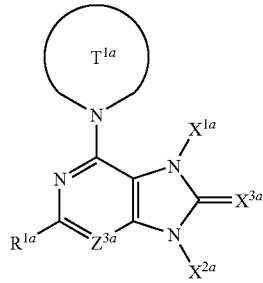

(II)

[wherein, $Z^{3a}$ denotes a nitrogen atom or a group of the formula $—CR^{2a}=$;

$X^{3a}$ denotes an oxygen atom or a sulfur atom;

$T^1a$ stands for a monocyclic 4 to 8-membered heterocycle containing 1 or 2 nitrogen atoms in the ring, which may have an amino group or a $C_{1-6}$ alkylamino group;

$X^{1a}$ denotes a hydrogen atom, a $C_{2-6}$ alkenyl group, a $C_{2-6}$ alkynyl group, or a benzyl group;

$R^{1a}$ and $R^{2a}$ each independently denote a hydrogen atom, a halogen atom, a $C_{1-6}$ alkyl group, a cyano group, or a group represented by the formula $—A^{0a}—A^{1a}$;

$A^{0a}$ denotes an oxygen atom, a sulfur atom, or a group represented by the formula $—NA^{2a}—$;

$A^{1a}$ denotes a hydrogen atom, a $C_{1-6}$ alkyl group, a $C_{2-6}$ alkenyl group, a $C_{2-6}$ alkynyl group, a phenyl group, a cyanophenyl group, a carbamoylphenyl group, a benzyl group, a pyridylmethyl group, or a pyridyl group;

$A^{2a}$ denotes a hydrogen atom, or a $C_{1-6}$ alkyl group;

$X^{2a}$ denotes a hydrogen atom, a $C_{2-6}$ alkenyl group, a $C_{2-6}$ alkynyl group, a cyclohexenyl group, a 1H-pyridin-2-on-yl group, a 1-methyl-1H-pyridin-2-on-yl group, a $C_{1-6}$ alkyl group that may have a group selected from substituent group B described below, a phenyl group that may have a group selected from substituent group B described below, a 5 or 6-membered heteroaryl group that may have a group selected from substituent group B described below, a phenyl $C_{1-6}$ alkyl group that may have a group selected from substituent group B described below, or a pyridyl $C_{1-6}$ alkyl group that may have a group selected from substituent group B described below:

<Substituent Group B> substituent group B refers to a group consisting of a chlorine atom, a bromine atom, a cyano group, a $C_{1-6}$ alkyl group, a $C_{2-6}$ alkenyl group, a $C_{2-6}$ alkynyl group, a $C_{3-8}$ cycloalkyl group, a $C_{1-6}$ alkoxy group, a carbamoyl group, a carboxyl group, and a $C_{1-6}$ alkoxycarbonyl group];

(3) a compound represented by the general formula (III), or a salt or a hydrate thereof,

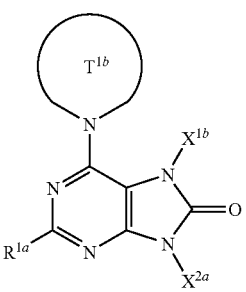

(III)

[wherein, $T^{1b}$ stands for a piperazin-1-yl group, a 3-amino-piperidin-1-yl group, or a 3-methylamino-piperidin-1-yl group;

$X^{1b}$ denotes a 2-pentynyl group, a 2-butynyl group, a 3-methyl-2-butenyl group, a 2-butenyl group, or a benzyl group; and $R^{1a}$ and $X^{2a}$ have the same meaning as $R^{1a}$ and $X^{2a}$ of (2) defined above];

(4) the compound of (2) or (3), or a salt or a hydrate thereof, wherein $R^{1a}$ is a hydrogen atom, a chlorine atom, a cyano group, a methoxy group, an ethoxy group, an i-propyloxy group, a methylthio group, an allyloxy group, a 2-butynyloxy group, a phenyloxy group, a cyanophenyloxy group, a carbamoylphenyloxy group, a phenylmethyloxy group, a (phenylmethyl)amino group, a pyridylmethyloxy group, a pyridyloxy group, an amino group, a methylamino group, a dimethylamino group, or a diethylamino group;

(5) the compound of (2) or (3), or a salt or a hydrate thereof, wherein $R^{1a}$ is a hydrogen atom, a methoxy group, an ethoxy group, an i-propyloxy group, a 2-cyanophenyloxy group, or a 2-carbamoylphenyloxy group;

(6) the compound of any one of (2) to (5), or a salt or a hydrate thereof, wherein $X^{2a}$ is a hydrogen atom, a methyl group, an ethyl group, an n-propyl group, a 2-methylpropyl group, a group represented by the formula $—CH_2—R^{10}$ (where $R^{10}$ denotes a carbamoyl group, a carboxyl group, a methoxycarbonyl group, a cyano group, a cyclopropyl group, or a methoxy group), a 3-cyanopropyl group, an allyl group, a 2-propionyl group, a 2-butynyl group, a 2-methyl-2-propenyl group, a 2-cyclohexynyl group, a chloropyridyl group, a methoxypyridyl group, a methoxypyrimidyl group, a pyridyl group, a furyl group, a thienyl group, a pyridylmethyl group, a 1H-pyridin-2-on-5-yl group, a 1-methyl-1H-pyridin-2-on-5-yl group, a phenyl group that may have a group selected from substituent group Y described below, a benzyl group that may have a group selected from substituent group Y described below, or a phenethyl group that may have a group selected from substituent group Y described below: substituent group Y is a group consisting of: a chlorine atom, a bromine atom, a methoxy group, a cyano group, a vinyl group, and a methyl group;

(7) the compound of any one of (2) to (5), a salt thereof, or a hydrate thereof, wherein $X^{2A}$ is a methyl group, n-propyl group, allyl group, 2-propynyl group, 2-butynyl group, cyclopropylmethyl group, phenyl group, 3-pyridyl group, 3-furyl group, 3-thienyl group, 2-methoxy-5-pyrimidinyl group, 2-methoxy-5-pyridyl group, 2-chloro-4-pyridyl group, or 1H-pyridin-2-on-5-yl group;

(8) a pharmaceutical comprising the compound of (1), a salt thereof, or a hydrate thereof;

(9) a dipeptidyl peptidase IV inhibitor comprising the compound of (1), a salt thereof, or a hydrate thereof;

(10) a pharmaceutical composition comprising the compound of (1), a salt thereof, or a hydrate thereof, and an adjuvant for formulation;

(11) a preventive or therapeutic agent for diabetes, obesity, hyperlipidemia, AIDS, osteoporosis, gastrointestinal disorder, angiogenesis, infertility, inflammatory disease, multiple sclerosis, allergic disease, or cancer, or an immunoregulatory agent, hormone regulatory agent, or antirheumatic agent, which comprises the compound of (1), a salt thereof, or a hydrate thereof;

(12) a preventive or therapeutic agent for diabetes, comprising the compound of (1), a salt thereof, or a hydrate thereof;

(13) a method for treatment or prevention of a disease for which dipeptidyl peptidase IV inhibition is effective, wherein the method comprises the step of administering a patient with a pharmaceutically effective dose of the compound of (1), a salt thereof, or a hydrate thereof;

(14) the method of treatment or prevention of (13), wherein the disease for which dipeptidyl peptidase IV inhibition is effective is diabetes;

(15) the use of the compound of (1), a salt thereof or a hydrate thereof for producing a pharmaceutical;

(16) the use of (15), wherein the pharmaceutical is a therapeutic agent or a preventive agent for a disease for which dipeptidyl peptidase IV inhibition is effective;

(17) the use of (15), wherein the pharmaceutical is a therapeutic agent or a preventive agent for diabetes.

Hereinafter, the present invention is described specifically by describing the meaning of terms, symbols, and such used in this description.

In this description, the structural formula of the compounds represents a certain isomer for convenience, however, the present invention includes all isomers, such as geometric isomers, optical isomers based on asymmetric carbon, stereoisomers, and tautomers that structurally arise from compounds, as well as mixtures of isomers, and is not to be limited to the formula represented for convenience, and may be any one or a mixture of isomers. Therefore, optically active substances and racemic substances with asymmetric carbon atoms in the molecule may exist, but the present invention has no particular limitations, and any of them are included. Furthermore, crystal polymorphism may exist, but similarly, there are no limitations, and the crystal form may be any one form or may be a mixture, and may be an anhydride or a hydrate.

The compounds of this invention may also be solvates that have absorbed some other type of solvent.

Furthermore, the compounds of the present invention include compounds exhibiting a desired activity even after being metabolized, such as after being oxidized, reduced, hydrolyzed, or conjugated in vivo. The present invention also includes compounds that produce the compounds of this invention after being metabolized, such as after being oxidized, reduced, and hydrolyzed in vivo.

The phrase "$C_{1-6}$ alkyl group" means a linear or branched alkyl group containing 1 to 6 carbon atoms, which is a monovalent group derived by removal of any one of the hydrogen atoms from an aliphatic hydrocarbon containing 1 to 6 carbons, and specific examples include a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group.

The phrase "$C_{2-6}$ alkenyl group" means a linear or branched alkenyl group containing 2 to 6 carbons, and specific examples include a vinyl group, an allyl group, a 1-propenyl group, a 1-methylvinyl group, a 1-butenyl group, a 2-butenyl group, a 3-butenyl group, a pentenyl group, and a hexenyl group.

The phrase "$C_{2-6}$ alkynyl group" means a linear or branched alkynyl group containing 2 to 6 carbons, and specific examples include an ethynyl group, a 1-propynyl group, a 2-propynyl group, a butynyl group, a pentynyl group, and a hexynyl group.

The phrase "$C_{3-8}$ cycloalkyl group" means a cyclic aliphatic hydrocarbon group containing 3 to 8 carbon atoms, and specific examples include a cyclopropyl group, a cyclobutyl group, a cyclopentyl group, a cyclohexyl group, a cycloheptyl group, and a cyclooctynyl group.

The phrase "$C_{1-6}$ alkylene group" means a divalent group derived by removal of another arbitrary hydrogen atom from an above-defined "$C_{1-6}$ alkyl group", and specific examples include a methylene group, a 1,2-ethylene group, a 1,1-ethylene group, a 1,3-propylene group, a tetramethylene group, a pentamethylene group, and a hexamethylene group.

The phrase "$C_{1-6}$ alkoxy group" means an oxygen atom to which an above-defined "$C_{1-6}$ alkyl group" is bound, and specific examples include a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, and a 2,3-dimethyl-2-butyloxy group.

The phrase "$C_{1-6}$ alkoxycarbonyl group" means a carbonyl group to which an above-defined "$C_{1-6}$ alkoxy group" is bound, and specific examples include a methoxycarbonyl group, an ethoxycarbonyl group, a 1-propyloxycarbonyl group, a 2-propyloxycarbonyl group, a 2-methyl-1-propyloxycarbonyl group, and a 2-methyl-2-propyloxycarbonyl group.

The phrase "$C_{1-6}$ alkylthio group" means a sulfur atom to which an above-defined "$C_{1-6}$ alkyl group" is bound, and specific examples include a methylthio group, an ethylthio group, a 1-propylthio group, a 2-propylthio group, a 2-methyl-1-propylthio group, a 2-methyl-2-propylthio group, a 1-butylthio group, a 2-butylthio group, a 1-pentylthio group, a 2-pentylthio group, a 3-pentylthio group, a 2-methyl-1-butylthio group, a 3-methyl-1-butylthio group, a 2-methyl-2- butylthio group, a 3-methyl-2-butylthio group, a 2,2-dimethyl-1-propylthio group, a 1-hexylthio group, a 2-hexylthio group, a 3-hexylthio group, a 2-methyl-1-pentylthio group, a 3-methyl-1-pentylthio group, a 4-methyl-1-pentylthio group, a 2-methyl-2-pentylthio group, a 3-methyl-2-pentylthio group, a 4-methyl-2-pentylthio group, a 2-methyl-3-pentylthio group, a 3-methyl-3-pentylthio group, a 2,3-dimethyl-1-butylthio group, a 3,3-dimethyl-1-butylthio group, a 2,2-dimethyl-1-butylthio group, a 2-ethyl-1-butylthio group, a 3,3-dimethyl-2-butylthio group, and a 2,3-dimethyl-2-butylthio group.

The phrase "halogen atom" means a fluorine atom, a chlorine atom, a bromine atom, or an iodine atom.

The phrase "heteroatom" means a sulfur atom, an oxygen atom, or a nitrogen atom.

The phrase "4 to 8-membered heterocycle" means a non-aromatic ring, wherein 1) the number of atoms constituting the ring of the cyclic group ranges from 4 to 8;

2) 1 to 2 heteroatoms exist among the atoms constituting the ring of the cyclic group;

3) the number of double bonds in the ring is in the range of 0 to 2;

4) the number of carbonyl groups in the ring is in the range of 0 to 3; and 5) the ring is monocyclic.

Specific examples of the "4 to 8-membered heterocycle" include a pyrrolidine ring, a piperidine ring, an azepane ring, a tetrahydrofuran ring, a tetrahydropyran ring, a morpholine ring, a thiomorpholine ring, a piperazine ring, a thiazolidine ring, a dioxane ring, an imidazoline ring, a thiazoline ring, an azetidine ring, and a ring represented by one of the formulae:

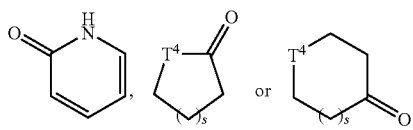

(where s stands for an integer of 1 to 3; and $T^4$ denotes a methylene group, an oxygen atom, or a group represented by the formula —$NT^5$-(where $T^5$ denotes a hydrogen atom, or a $C_{1-6}$ alkyl group)).

The phrase "4 to 8-membered heterocyclic group" means a monovalent group derived by removal of one hydrogen atom at a random position from an above-described "4 to 8-membered heterocycle".

The phrase "$C_{6-10}$ aryl group" means an aromatic hydrocarbon ring group containing 6 to 10 carbon atoms, and specific examples include a phenyl group, a 1-naphthyl group, and a 2-naphthyl group.

The phrase "5 to 10-membered heteroaryl ring" means an aromatic ring group containing 5 to 10 atoms which constitute the ring of a cyclic group among which heteroatoms are included, and specific examples include a pyridine ring, a thiophene ring, a furan ring, a pyrrole ring, an oxazole ring, an isoxazole ring, a thiazole ring, an isothiazole ring, an imidazole ring, a triazole ring, a pyrazole ring, a furazan ring, a thiadiazole ring, an oxadiazole ring, a pyridazine ring, a pyrimidine ring, a pyrazine ring, an indole ring, an isoindole ring, an indazole ring, a chromene ring, a quinoline ring, an isoquinoline ring, a cinnoline ring, a quinazoline ring, a quinoxaline ring, a naphthyridine ring, a phthalazine ring, a purine ring, a pteridine ring, a thienofuran ring, an imidazothiazole ring, a benzofuran ring, a benzothiophene ring, a benzoxazole ring, a benzothiazole ring, a benzothiadiazole ring, a benzimidazole ring, imidazopyridine ring, a pyrrolopyridine ring, a pyrrolopyrimidine ring, and a pyridopyrimidine ring.

The phrase "5 to 10-membered heteroaryl group" means a monovalent group derived by removal of one hydrogen atom at a random position from an above-described "5 to 10-membered heteroaryl ring".

The phrase "$C_{6-10}$ aryl $C_{1-6}$ alkyl group" means a group in which a random hydrogen atom in an above-described "$C_{1-6}$ alkyl group" is substituted with an above-described "$C_{6-10}$ aryl group", and specific examples include a benzyl group, a phenethyl group, and a 3-phenyl-1-propyl group.

The phrase "5 to 10-membered heteroaryl $C_{1-6}$ alkyl group" means a group in which a random hydrogen atom in an above-described "$C_{1-6}$ alkyl group" is substituted with an above-described "5 to 10-membered heteroaryl group", and specific examples include a 2-pyridylmethyl group, and a 2-thienylmethyl group.

The phrase "5 or 6-membered heteroaryl ring" means an aromatic ring group containing 5 to 6 atoms which constitute the ring of a cyclic group among which one or more heteroatoms are included, and specific examples include a pyridine ring, a thiophene ring, a furan ring, a pyrrole ring, an oxazole ring, an isoxazole ring, a thiazole ring, an isothiazole ring, an imidazole ring, a triazole ring, a pyrazole ring, a thiadiazole ring, an oxadiazole ring, a pyridazine ring, a pyrimidine ring, and a pyrazine ring.

The phrase "5 or 6-membered heteroaryl group" means a monovalent group derived by removal of one hydrogen atom at a random position from this "5 or 6-membered aromatic heteroaryl ring".

The phrase "pyridyl group" means a 2-pyridyl group, a 3-pyridyl group, or a 4-pyridyl group.

The phrase "furyl group" means a 2-furyl group, or a 3-furyl group.

The phrase "thienyl group" means a 2-thienyl group or a 3-thienyl group.

The phrase "cyclohexenyl group" means a 1-cyclohexenyl group, a 2-cyclohexenyl group, or a 3-cyclohexenyl group.

The phrase "1H-pyridin-2-on-yl group" means a monovalent group derived by removal of one random hydrogen atom from a "1H-pyridin-2-one", and specific examples include groups represented by the formulae:

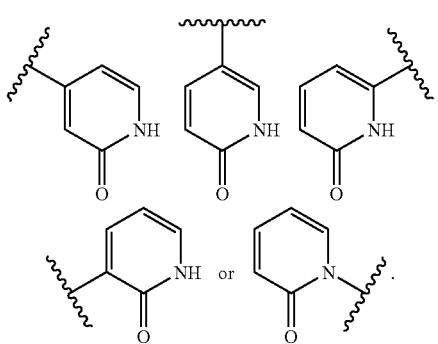

The phrase "1-methyl-1H-pyridin-2-on-yl group" means a monovalent group derived by removal of one random hydrogen atom from a "1-methyl-1H-pyridin-2-one", and specific examples include groups represented by the formulae:

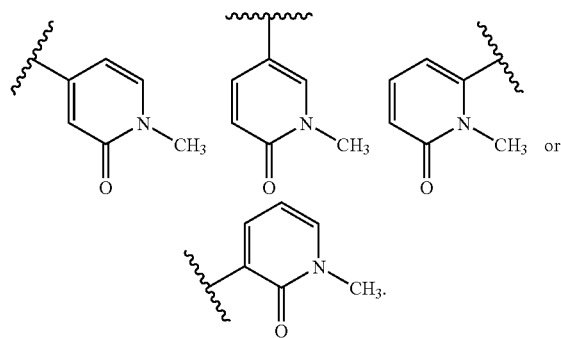

The phrase "phenyl $C_{1-6}$ alkyl group" means a group wherein a random hydrogen atom of an above-described "$C_{1-6}$ alkyl group" is substituted with a phenyl group, and specific examples include a benzyl group, a phenethyl group, and a 3-phenyl-1-propyl group.

The phrase "pyridyl $C_{1-6}$ alkyl group" means a group wherein a random hydrogen atom of an above-described "$C_{1-6}$ alkyl group" is substituted with an above-described "pyridyl group", and specific examples include a 2-pyridylmethyl group, a 3-pyridylmethyl group, and a 4-pyridylmethyl group.

The phrase "pyridylmethyl group" means a 2-pyridylmethyl group, a 3-pyridylmethyl group, or a 4-pyridylmethyl group.

The phrase "pyridyloxy group" means a 2-pyridyloxy group, a 3-pyridyloxy group, or a 4-pyridyloxy group.

The phrase "pyridylmethyloxy group" means a 2-pyridylmethyloxy group, a 3-pyridylmethyloxy group, or a 4-pyridylmethyloxy group.

The phrase "cyanophenyl group" means a 2-cyanophenyl group, a 3-cyanophenyl group, or a 4-cyanophenyl group.

The phrase "carbamoylphenyl group" means a 2-carbaomylphenyl group, a 3-carbamoylphenyl group, or a 4-carbamoylphenyl group.

The phrase "cyanophenyloxy group" means a 2-cyanophenyloxy group, a 3-cyanophenyloxy group, or a 4-cyanophenyloxy group.

The phrase "carbamoylphenyloxy group" means a 2-carbamoylphenyloxy group, a 3-carbamoylphenyloxy group, or a 4-carbamoylphenyloxy group.

The phrase "chloropyridyl group" means a group wherein a random hydrogen atom in an above-described "pyridyl group" is substituted with a chlorine atom, and specific examples include a 2-chloropyridine-3-yl group, a 2-chloropyridin-4-yl group, and a 6-chloropyridin-3-yl group.

The phrase "methoxypyridyl group" means a group wherein a random hydrogen atom in an above-described "pyridyl group" is substituted with a methoxy group, and specific examples include a 2-methoxypyridine-3-yl group, a 2-methoxypyridine-4-yl group, and a 6-methoxypyridin-3-yl group.

The phrase "methoxypyrimidyl group" means a group wherein a random hydrogen atom in an above-described "pyrimidyl group" is substituted with a methoxy group, and specific examples include a 2-methoxypyrimidin-5-yl group, and a 2-methoxypyrimidin-4-yl group.

The phrase "monocyclic or bicyclic 4 to 12-membered heterocycle containing 1 or 2 nitrogen atoms in the ring, which may have substituents" means a non-aromatic ring, wherein 1) the number of atoms constituting the ring of the cyclic group ranges from 4 to 12;

2) 1 or 2 nitrogen atoms are included among the atoms constituting the ring of the cyclic group;

3) the ring may have substituents; and 4) the ring is monocyclic or bicyclic.

More specifically, it refers to a group represented by one of the formulae:

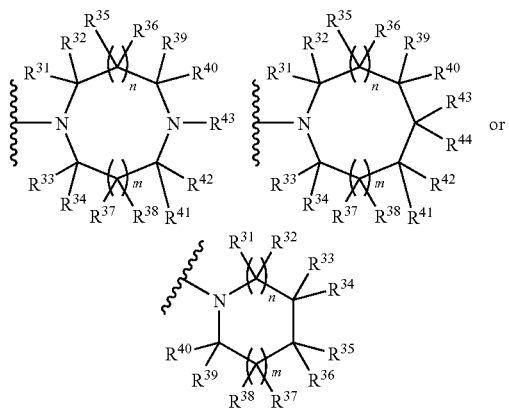

(where m and n each independently denote 0 or 1; any two from among $R^{31}$ to $R^{44}$ may together form a $C_{1-6}$ alkylene group.)

[Definition of $T^{1a}$]

$T^{1a}$ denotes a "monocyclic 4 to 8-membered heterocyclic group containing 1 or 2 nitrogen atoms in the ring, that may have an amino group or a $C_{1-6}$ alkylamino group", wherein 1) the number of atoms constituting the ring of the cyclic group ranges from 4 to 8;

2) 1 or 2 nitrogen atoms are included among the atoms constituting the ring of the cyclic group;

3) the ring may have an amino group or a $C_{1-6}$ alkylamino group as a substituent; and 4) the ring is a monocyclic non-aromatic ring group.

The phrase "$C_{1-6}$ alkylamino group" means a nitrogen atom to which 1 or 2 of an above-described "$C_{1-6}$ alkyl groups" are bound, and specific examples include a methylamino group, an ethylamino group, a propylamino group, a dimethylamino group, a diethylamino group, and a dipropylamino group. $T^{1a}$ is (1) preferably a piperazin-1-yl group, a [1.4]diazepan-1-yl group, a [1.5]diazocan-1-yl group, an azetidin-1-yl group that may have an amino group or a $C_{1-6}$ alkylamino group, a pyrrolidin-1-yl group that may have an amino group or a $C_{1-6}$ alkylamino group, a piperidin-1-yl group that may have an amino group or a $C_{1-6}$ alkylamino group, an azepan-yl group that may have an amino group or a $C_{1-6}$ alkylamino group, or an azocan-yl group that may have an amino group or a $C_{1-6}$ alkylamino group;

(2) more preferably a group represented by one of the formulae:

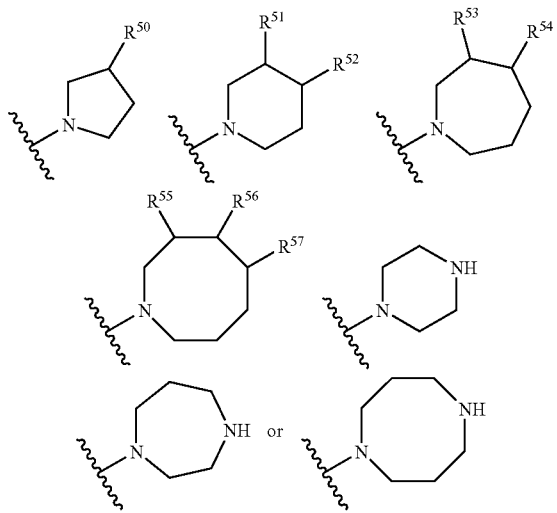

(where $R^{50}$ denotes an amino group or a methylamino group; $R^{51}$ or $R^{52}$ denote either an amino group or a methylamino group, and the other denotes a hydrogen atom; $R^{53}$ or $R^{54}$ denotes either an amino group or a methylamino group, and the other denotes a hydrogen atom; and any one of $R^{55}$ to $R^{57}$ denotes an amino group or a methylamino group, and the remaining two denote hydrogen atoms.);

(3) even more preferably a piperazin-1-yl group, a 3-amino-piperidin-1-yl group, or a 3-methylamino-piperidin-1-yl group; and (4) most preferably a piperazin-1-yl group.

[Definition of $T^{1b}$]

$T^{1b}$ denotes a piperazin-1-yl group, a 3-amino-piperidin-1-yl group, or a 3-methylamino-piperidin-1-yl group, and especially preferably a piperazin-1-yl group.

[Definition of $X^{3a}$]

$X^{3a}$ denotes an oxygen atom or a sulfur atom, and especially preferably an oxygen atom.

[Definition of $X^{1a}$]

$X^{1a}$ denotes a hydrogen atom, a $C_{2-6}$ alkenyl group, a $C_{2-6}$ alkynyl group, or a benzyl group, especially (1) preferably a hydrogen atom, a 2-pentynyl group, a 2-butynyl group, a 3-methyl-2-butenyl group, a benzyl group, or a 2-butenyl group;

(2) more preferably a 2-butynyl group, or a 2-butenyl group; and (3) even more preferably a 2-butynyl group.

[Definition of $X^{1b}$]

$X^{1b}$ denotes a hydrogen atom, a 2-pentynyl group, a 2-butynyl group, a 3-methyl-2-butenyl group, a benzyl group, or a 2-butenyl group, especially (1) preferably a 2-butynyl group, or a 2-butenyl group; and (2) more preferably a 2-butynyl group.

[Definition of $R^{1a}$]

$R^{1a}$ denotes "a hydrogen atom, a halogen atom, a $C_{1-6}$ alkyl group, a cyano group, or a group represented by the formula $A^{0a}$—$A^{1a}$ (where $A^{0a}$ denotes an oxygen atom, a sulfur atom, or a group represented by —$NA^{2a}$—; $A^{1a}$ denotes a hydrogen atom, a $C_{1-6}$ alkyl group, a $C_{2-6}$ alkenyl group, a $C_{2-6}$ alkynyl group, a phenyl group, a cyanophenyl group, a carbamoylphenyl group, a benzyl group, a pyridylmethyl group, or a pyridyl group; and $A^{2a}$ denotes a hydrogen atom, or a $C_{1-6}$ alkyl group)", especially (1) preferably a hydrogen atom, a chlorine atom, a cyano group, a methoxy group, an ethoxy group, an i-propyloxy group, a methylthio group, an allyloxy group, a 2-butynyloxy group, a phenyloxy group, a cyanophenyloxy group, a carbamoylphenyloxy group, a phenylmethyloxy group, a (phenylmethyl)amino group, a pyridylmethyloxy group, a pyridyloxy group, an amino group, a methylamino group, a dimethylamino group, or a diethylamino group;

(2) more preferably a hydrogen atom, a methoxy group, an ethoxy group, an i-propyloxy group, a 2-cyanophenyloxy group, or a 2-carbamoylphenyloxy group; and (3) even more preferably a hydrogen atom, a methoxy group, an ethoxy group, or an i-propyloxy group.

[Definition of $X^{2a}$]

$X^{2a}$ denotes a hydrogen atom, a $C_{2-6}$ alkenyl group, a $C_{1-6}$ alkynyl group, a cyclohexenyl group, a 1H-pyridin-2-on-yl group, a 1-methyl-1H-pyridin-2-on-yl group, a $C_{1-6}$ alkyl group that may have groups selected from substituent group B mentioned below, a phenyl group that may have groups selected from substituent group B mentioned below, a 5 or 6-membered heteroaryl group that may have groups selected from substituent group B mentioned below, a phenyl $C_{1-6}$ alkyl group that may have groups selected from substituent group B mentioned below, or a pyridyl $C_{1-6}$ alkyl group that may have groups selected from substituent group B mentioned below:

(substituent group B refers to a group consisting of: a chlorine atom, a bromine atom, a cyano group, a $C_{1-6}$ alkyl group, a $C_{2-6}$ alkenyl group, a $C_{2-6}$ alkynyl group, a $C_{3-8}$ cycloalkyl group, a $C_{1-6}$ alkoxy group, a carbamoyl group, carboxyl group, and a $C_{1-6}$ alkoxycarbonyl group), especially (1) preferably a hydrogen atom, a methyl group, an ethyl group, an n-propyl group, a 2-methylpropyl group, a group represented by the formula —$CH_2$—$R^{11}$ (where $R^{10}$ denotes a carbamoyl group, a carboxyl group, a methoxycarbonyl group, a cyano group, a cyclopropyl group, or a methoxy group), a 3-cyanopropyl group, an aryl group, a 2-propynyl group, a 2-butynyl group, a 2-methyl-2-propenyl group, a 2-cyclohexynyl group, a chloropyridyl group, methoxypyridyl group, a methoxypyrimidyl group, a pyridyl group, a furyl group, an thienyl group, a pyridylmethyl group, a 1H-pyridin-2-on-5-yl group, a 1-methyl-1H-pyridin-2-on-5-yl group, a phenyl group that may have groups selected from substituent group Y mentioned below, a benzyl group that may have groups selected from substituent group Y mentioned below, or a phenethyl group that may have groups selected from substituent group Y mentioned below (substituent group Y is a group consisting of a chlorine atom, a bromine atom, a methoxy group, a cyano group, a vinyl group, and a methyl group);

(2) more preferably a methyl group, an n-propyl group, an aryl group, a 2-propynyl group, a 2-butynyl group, a cyclopropylmethyl group, a phenyl group, a 3-pyridyl group, a 3-furyl group, a 3-thienyl group, a 2-methoxy-5-pyrimidinyl group, a 2-methoxy-5-pyridyl group, a 2-chloro-4-pyridyl group, or a 1H-pyridin-2-on-5-yl group; and (3) even more preferably a methyl group, an allyl group, a cyclopropylmethyl group, a 3-pyridyl group, a 3-furyl group, a 2-methoxy-5-pyrimidinyl group, a 2-methoxy-5-pyridyl group, a 2-chloro-4-pyridyl group, or a 1H-pyridin-2-on-5-yl group.

Preferred groups were indicated in the definitions of $T^{1a}$ or $T^{1b}$, $X^{3a}$, $X^{1a}$ or $X^{1b}$, $R^{1a}$, and $X^{2a}$, and specific examples of compounds include compounds in which the preferred groups are selected from a group consisting of $T^{1a}$ or $T^{1b}$, $X^{3a}$, $X^{1a}$ or $X^{1b}$, $R^{1a}$, and $X^{2a}$, and the selected groups are combined randomly.

The phrase "may have substituents" has the same meaning as "in the substitutable sites, may have a random combination of 1 or 3 substituents". Specific examples of the substituents include:

(1) a halogen atom;

(2) a nitro group;

(3) a cyano group;

(4) a trifluoromethyl group;

(5) a group represented by the formula —$T^2$—$T^3$ (where $T^2$ denotes a single bond, a $C_{1-6}$ alkylene group, an oxygen atom, a sulfur atom, a sulfinyl group, a sulfonyl group, a carbonyl group, a groups represented by the formula —O—CO—, a groups represented by the formula —CO—O—, a groups represented by the formula —$NR^T$—, a groups represented by the formula —CO—$NR^T$—, a groups represented by the formula —$NR^T$—CO—, a groups represented by the formula —$SO_2$—$NR^T$—, or a groups represented by the formula —$NR^T$—$SO_2$—; $T^3$ and $R^T$ each independently denote a hydrogen atom, a $C_{1-6}$ alkyl group, a $C_{1-6}$ alkoxy group, a $C_{3-8}$ cycloalkyl group, a $C_{2-6}$ alkenyl group, a $C_{2-6}$ alkynyl group, a $C_{6-10}$ aryl group, a 5 to 10-membered heteroaryl group, or a 4 to 8-membered heterocyclic group; however, $T^3$ and $R^T$ each independently may have 1 to 3 substituents selected from substituent group T described below; however, cases in which $T^2$ is a single bond and $T^3$ is a hydrogen atom are excluded:

<Substituent Group T> substituent group T is a group consisting of a hydroxyl group, a cyano group, a halogen atom, and groups represented by a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5 to 10-membered heteroaryl group, a 4 to 8-membered heterocyclic group, a $C_{1-6}$ alkoxy group, and a $C_{1-6}$ alkylthio group).

Examples of the "salts" of this invention include salts with inorganic acids, salts with organic acids, salts with inorganic bases, salts with organic bases, and salts with acidic or basic amino acids, and pharmaceutically acceptable salts are particularly favorable.

Favorable examples of salts with inorganic acids include salts with hydrochloric acid, hydrobromic acid, sulfuric acid, nitric acid, and phosphoric acid. Favorable examples of salts with organic acids include salts with acetic acid, succinic acid, fumaric acid, maleic acid, tartaric acid, citric acid, lactic acid, stearic acid, benzoic acid, methanesulfonic acid, and p-toluenesulfonic acid.

Favorable examples of salts with inorganic bases include alkali metal salts such as sodium salts, and potassium salts; alkaline earth metal salts such as calcium salts, and magnesium salts; aluminum salts; and ammonium salts. Favorable examples of salts with organic bases include salts with diethylamine, diethanolamine, meglumine, and N,N'-dibenzylethylenediamine.

Favorable examples of salts with an acidic amino acid include salts with aspartic acid and glutamic acid, and favorable examples of salts with a basic amino acid include salts with arginine, lysine, and ornithine.

Hereinafter, the meaning of each symbol in the production methods will be described. $R^1$, $R^{2a}$, $X^1$, $X^2$, $X^{3a}$, and $T^1$ have the same meaning as defined above. $U^1$ and $U^2$ denote leaving groups (for example, chlorine atoms, bromine atoms, iodine atoms, methanesulfonyloxy groups, p-toluenesulfonyloxy groups, —$B(OH)_2$, 4,4,5,5-tetramethyl-1,3,2-dioxaborolan-2-yl groups, or groups represented by the formula —$Sn(R^Z)_3$ (where $R^Z$ denotes a $C_{1-6}$ alkyl group)). Hal denotes a halogen atom, such as a chlorine atom, a bromine atom, or an iodine atom. $M^1$ denotes a hydrogen atom, a sodium atom, a potassium atom, a lithium atom, —MgCl, —MgBr, —$Sn(R^Z)_3$ (where $R^Z$ has the same meaning as defined above), and so on. Y denotes a halogen atom such as a chlorine atom, a bromine atom, or an iodine atom, or a hydrogen atom. $P^1$ and $P^2$ each independently denote an amino protecting group, such as a benzyl group, a pivaloyloxymethyl group, a t-butoxycarbonyl group, or a cyanoethyl group. $T^{2b}$ has the same meaning as $T^1$, or denotes $T^1$ that has a protecting group (t-butoxycarbonyl group and such)-bound amino group.

Production Method A

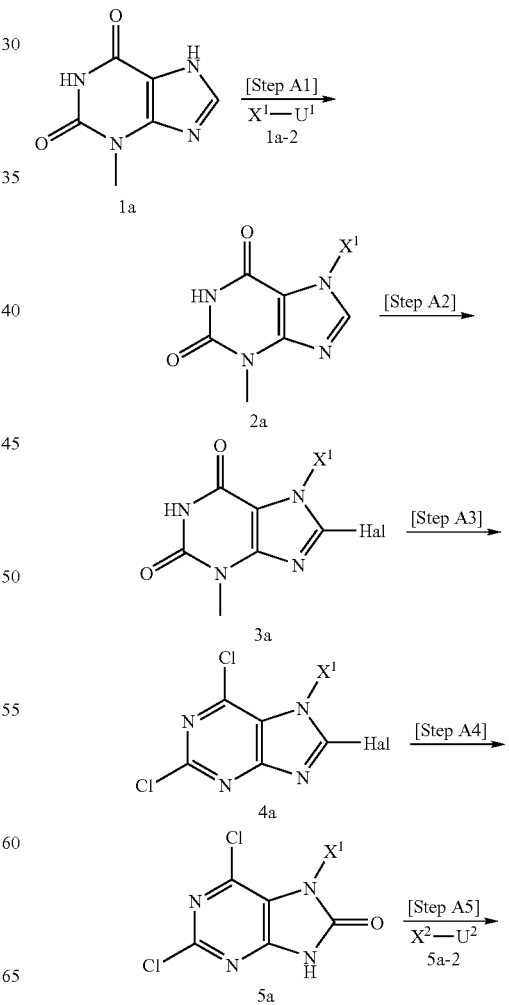

-continued

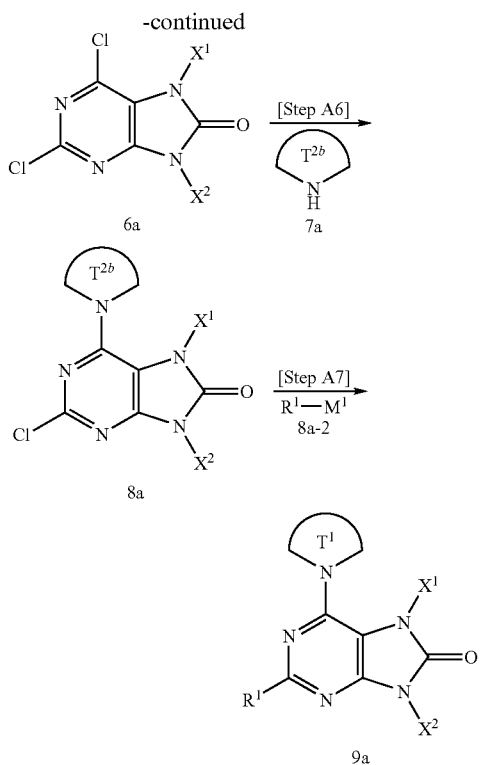

[Step A1]

This is a step for obtaining compound (2a) by performing a substitution reaction between compound (1a) [CAS No. 1076-22-8] and compound (1a-2) to introduce a substituent to the amino group at position 7 of compound (1a).

When compound (1a-2) is an electrophilic reagent represented by the formula $X^1$—$U^1$ (where $X^1$ and $U^1$ have the same meaning as defined above), or more specifically an alkyl halide such as iodomethane, iodoethane, iodopropane, or benzyl bromide; alkenyl halide such as allyl bromide, or 1-bromo-3-methyl-2-butene; alkynyl halide such as propargyl bromide, or 1-bromo-2-butyne, or such, the reaction can be performed under the conditions below. In such cases, the use of 1 to 2 times the amount of compound (1a-2) relative to compound (1a) is preferred.

Reaction conditions for the substitution reaction are not particularly limited, and for example, the reaction can be performed in a solvent such as dimethylsulfoxide, N,N-dimethylformamide, N-methylpyrrolidone, dioxane, tetrahydrofuran, or toluene, in the presence of a base such as lithium hydroxide, sodium hydroxide, potassium hydroxide, lithium carbonate, sodium carbonate, potassium carbonate, cesium carbonate, lithium hydride, sodium hydride, potassium hydride, butyllithium, methyllithium, lithium bistrimethylsilylamide, sodium bistrimethylsilylamide, or potassium bistrimethylsilylamide, at a temperature in the range of 0° C. to 150° C. In this case, the use of 1 to 2 times the amount of base relative to compound (1a) is preferred.

Specifically, when the $X^1$ that is introduced is a $C_{6-10}$ aryl group which may have substituents, or a 5 to 10-membered heteroaryl group which may have substituents, the reaction can be performed using aryl boronic acid, heteroaryl boronic acid, or such for compound (1a-2). In such a case, the use of 1 to 10 times the amount of compound (1a-2) relative to compound (1a) is preferred.

In this case, the reaction can be carried out in solvents such as dichloromethane, chloroform, 1,4-dioxane, tetrahydrofuran, toluene, pyridine, N,N-dimethylformamide, or N-methylpyrrolidone, in the presence of a base such as triethylamine, diisopropylethylamine, pyridine, N,N-dimethylamino pyridine, and a copper catalyst such as copper (II) acetate, copper (II) trifluoroacetate, copper (II) chloride, or copper (II) iodide, at a temperature in the range of 0° C. to 150° C. In this case, the use of 0.1 to 2 times the amount of copper catalyst relative to compound (1a) is preferred.

[Step A2]

This is a step for obtaining compound (3a) by reacting a halogenation reagent with compound (2a).

Specific examples of the halogenation reagent include N-chlorosuccinimide, N-bromosuccinimide, and N-iodosuccinimide. The use of 1 to 4 times the amount of such halogenation reagent relative to compound (2a) is preferred.

Reaction conditions for the halogenation are not particularly limited, and the reaction may be performed in a solvent such as acetonitrile, N,N-dimethylformamide, N-methylpyrrolidone, 1,4-dioxane, tetrahydrofuran, and dimethoxyethane, at a temperature in the range of 0° C. to 150° C.

[Step A3]

This is a step for obtaining compound (4a) by chlorinating compound (3a).

Reaction conditions are not particularly limited, and the reaction can be performed on compound (3a) with phosphorus oxychloride, phosphorus pentachloride, or a mixture thereof, in a solvent or without solvent, at a temperature in the range of 0° C. to 150° C. Toluene, acetonitrile, dichloroethane, and such may be used as the solvent.

[Step A4]

This is a step for obtaining compound (5a) by hydrolysis of compound (4a).

The reaction can be carried out using a base such as sodium acetate, potassium carbonate, or sodium hydroxide, in a solvent such as dimethylsulfoxide (wet), N-methylpyrrolidone (wet), tetrahydrofuran (wet), or water, or a mixture of such solvents, at a temperature in the range of 0° C. to 150° C. The use of 1 to 10 times the amount of base relative to compound (4a) is preferred.

[Step A5]

This is a step for obtaining compound (6a) by performing a substitution reaction between compound (5a) and compound (5a-2). When $X^2$ is a hydrogen atom, this step can be omitted.

When compound (5a-2) is an electrophilic reagent represented by the formula $X^2$—$U^2$ (where $X^2$ and $U^2$ have the same meaning as defined above), or more specifically an alkyl halide such as iodomethane, iodoethane, iodopropane, or benzyl bromide; an alkenyl halide such as allyl bromide, or 1-bromo-3-methyl-2-butene; an alkynyl halide such as propargyl bromide, or 1-bromo-2-butyne, or such, the reaction can be performed under the conditions below. In such cases, the use of 1 to 2 times the amount of compound (5a-2) relative to compound (5a) is preferred.

Reaction conditions for the substitution reaction are not particularly limited, and for example, the reaction can be performed in a solvent such as dimethylsulfoxide, N,N-dimethylformamide, N-methylpyrrolidone, dioxane, tetrahydrofuran, or toluene, in the presence of a base such as lithium hydroxide, sodium hydroxide, potassium hydroxide, lithium carbonate, sodium carbonate, potassium carbonate, cesium carbonate, lithium hydride, sodium hydride, potassium hydride, butyllithium, methyllithium, lithium bistrimethylsilylamide, sodium bistrimethylsilylamide, or potassium bistrimethylsilylamide, at a temperature in the range of 0° C. to 150° C. In this case, the use of 1 to 2 times the amount of base relative to compound (5a) is preferred.

When the $X^2$ that is introduced is a $C_{6-10}$ aryl group which may have substituents, or a 5 to 10-membered heteroaryl group which may have substituents, specifically, the reaction can be performed using aryl boronic acid, heteroaryl boronic acid, or such for compound (5a-2). In such a case, 1 to 10 times the amount of compound (5a-2) relative to compound (5a) is preferably used.

In this case, the reaction can be carried out in solvents such as dichloromethane, chloroform, 1,4-dioxane, tetrahydrofuran, toluene, pyridine, N,N-dimethylformamide, or N-methylpyrrolidone, in the presence of a base such as triethylamine, diisopropylethylamine, pyridine, or N,N-dimethylaminopyridine, and a copper catalyst such as copper (II) acetate, copper (III) trifluoroacetate, copper (II) chloride, or copper (II) iodide, at a temperature in the range of 0° C. to 15° C. In this case, the use of 0.1 to 2 times the amount of copper catalyst relative to compound (5a) is preferred.

[Step A6]

This is a step for obtaining compound (8a) by reacting compound (7a) with compound (6a). In this case, the use of 1 to 4 times the amount of compound (7a) relative to compound (6a) is preferred.

The reaction conditions are not particularly limited. For example, the reaction can be performed by mixing compound (6a) and compound (7a) in the presence or absence of a solvent such as N,N-dimethylformamide, N-methylpyrrolidone, methanol, ethanol, 1,4-dioxane, acetonitrile, toluene, or xylene, in the presence or absence of a base such as triethylamine, sodium bicarbonate, or potassium carbonate, at a temperature in the range of 0° C. to 200° C.

[Step A7]

This is a step for obtaining compound (9a) by introducing a substituent at position 2 of compound (8a), by performing a substitution reaction between compound (8a) and compound (8a-2).

Compound (8a-2), represented by the formula $R^1$—$M^1$ (where $R^1$ and $M^1$ each independently have the same meaning as defined above), is acceptable if it is a compound that may act as a nucleophilic agent in the presence or absence of an appropriate base, and specific preferred examples are alkyl alcohols such as methanol, n-propanol, isopropanol, and benzylalcohol; aryl alcohols such as phenol, and salicylamide; alkylamines such as ammonia, methylamine, dimethylamine, and diethylamine; arylamines such as aniline; alkylmercaptans such as methanethiol and t-butylmercaptan; arylmercaptans such as thiophenol; or others such as organolithium reagents; Grignard reagents; and organocopper reagents. In this case, the use of compound (8a-2) at 1 to 10 times the amount of compound (8a), or at a weight ratio of 5 to 100 times that of compound (8a), is preferred.

The reaction solvents that may be used include acetonitrile, N,N-dimethylformamide, N-methylpyrrolidone, 1,4-dioxane, tetrahydrofuran, dimethoxyethane, methanol, and ethanol.

The reaction can be carried out in the presence or absence of a base, and when performing the reaction in the presence of a base, lithium hydroxide, sodium hydroxide, potassium hydroxide, lithium carbonate, sodium carbonate, potassium carbonate, cesium carbonate, lithium hydride, sodium hydride, potassium hydride, butyllithium, methyllithium, lithium bistrimethylsilylamide, sodium bistrimethylsilylamide, potassium bistrimethylsilylamide, triethylamine, and such may be used as the base. In this case, the use of 1 to 10 times the amount of base relative to compound (8a) is preferred. The reaction can be performed at a temperature in the range of 0° C. to 150° C.

Compound (9a) can be obtained by reacting compound (8a), in the presence of a transition metal catalyst such as a palladium catalyst, with compound (8a-2) in which $M^1$ denotes MgCl, MgBr, Sn($R^Z$)$_3$ (where, $R^Z$ has the same meaning as defined above), or such. In this case, the use of 1 to 50 times the amount of compound (8a-2) relative to compound (8a) is preferred.

Herein, acetonitrile, N,N-dimethylformamide, N-methylpyrrolidone, 1,4-dioxane, tetrahydrofuran, dimethoxyethane, or such may be used as the reaction solvent.

Examples of the metal catalyst include palladium catalysts or copper catalysts. Tetrakistriphenylphosphine palladium, palladium acetate, dibenzylideneacetone palladium, or such may be used as the palladium catalyst, and copper iodide or such may be used as the copper catalyst. The use of 0.01 to 2 times the amount of metal catalyst relative to compound (8a) is preferred.

The reaction can be carried out in the presence of an organophosphorus ligand, and ortho-tolylphosphine, diphenylphosphinoferrocene, or such may be used as the organophosphorus ligand when performing a reaction in the presence of an organophosphorus ligand. In this case, the use of 1 to 5 times the amount of organic ligand relative to the metal catalyst is preferred.

The reaction can be performed in the presence or absence of a base, and when performing the reaction in the presence of a base, lithium hydroxide, sodium hydroxide, potassium hydroxide, lithium carbonate, sodium carbonate, potassium carbonate, cesium carbonate, lithium hydride, sodium hydride, potassium hydride, calcium phosphate, lithium bistrimethylsilylamide, sodium bistrimethylsilylamide, potassium bistrimethylsilylamide, triethylamine, or such may be used as the base. The reaction can be performed at a reaction temperature in the range of 0° C. to 150° C.

When $T^{2b}$ in compound (8a) contains an amino group protected by a protecting group such as t-butoxycarbonyl group, Step A7 is followed by deprotection. Regarding the conditions for the deprotection reaction, there are different methods depending on the protecting group that is used, and conditions generally used for cleavage of the leaving group can be used. For example, when the protecting group is a t-butoxycarbonyl group, deprotection can be carried out using an anhydrous methanol solution of hydrogen chloride, an anhydrous ethanol solution of hydrogen chloride, an anhydrous dioxane solution of hydrogen chloride, trifluoroacetic acid, or formic acid.

Production Method B

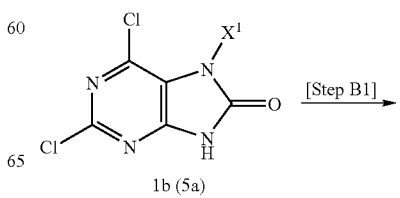

1b (5a)

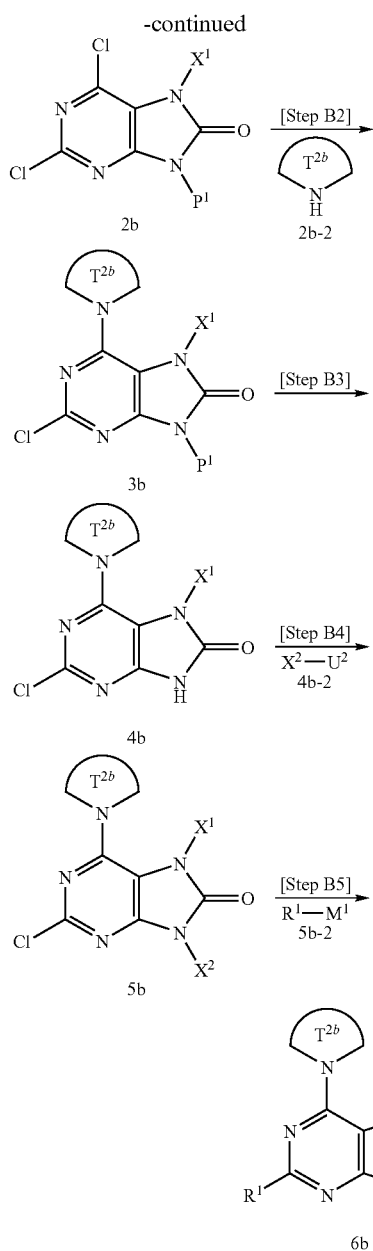

[Step B1]

This is a step for obtaining compound (2b) by protecting the amino group at position 9 of compound (1b) (compound 5a in Production method A). The introduction reaction of a protecting group can be performed under generally used conditions, depending on the reagent type used.

For the amino protecting reagent, a reagent generally used to introduce an amino protecting group can be used, and specifically, chloromethylpivalate and such may be used. The use of 1 to 2 times the amount of the protecting reagent relative to compound (1b) is preferred. The reaction can be performed using acetonitrile, N,N-dimethylformamide, N-methylpyrrolidone, 1,4-dioxane, tetrahydrofuran, dimethoxyethane, or such as the reaction solvent, and the use of N,N-dimethylformamide is preferred.

The reaction can be performed in the presence of a base. Examples of the base used herein include cesium carbonate, lithium carbonate, sodium carbonate, potassium carbonate, and sodium hydride, and the use of sodium hydride is preferred. Herein, the use of 1 to 5 times the amount of the base relative to compound (1b) is preferred. The reaction may be performed at a temperature in the range of 0° C. to 150° C., or preferably at room temperature.

[Step B2]

This is a step for obtaining compound (3b) by reacting compound (2b) with compound (2b-2). Reaction conditions similar to those of Production method A [Step A6] can be used.

[Step B3]

This is a step for obtaining compound (4b) by deprotecting the amino protecting group at position 9 of compound (3b).

The reaction conditions differ depending on the protecting group used, and for example, when the protecting group is a pivalyloxymethyl group, the reaction can be carried out in methanol, or a mixed solution of methanol and tetrahydrofuran, in the presence of a base such as sodium methoxide, sodium hydride, or 1,8-diazabicyclo[5.4.0]-7-undecene, at a temperature in the range of 0° C. to 150° C. In this case, the use of 0.1 to 2 times the amount of the base relative to compound (3b) is preferred.

[Step B4]

This is a step for obtaining compound (5b) by introducing a substituent to the amino group at position 9 of compound (4b) by performing a substitution reaction between compound (4b) and compound (4b-2). Reaction conditions similar to those of Production method A [Step A5] may be used.

[Step B5]

This is a step for obtaining compound (6b) by introducing a substituent at position 2 of compound (5b) by performing a substitution reaction between compound (5b) and compound (5b-2). Reaction conditions similar to those of Production method A [Step A7] may be used.

When compound (2b-2) containing an amino group protected with a protecting group such as a t-butoxycarbonyl group, is introduced in [Step B2], [Step B5] is followed by deprotection. Deprotection reaction conditions similar to those of Production method A [Step A7] may be used.

Production Method C-1

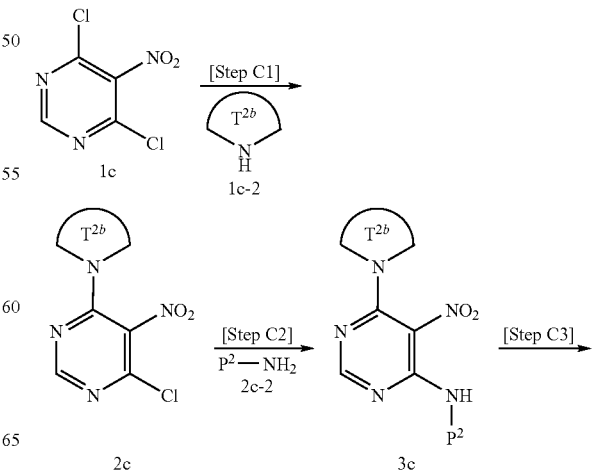

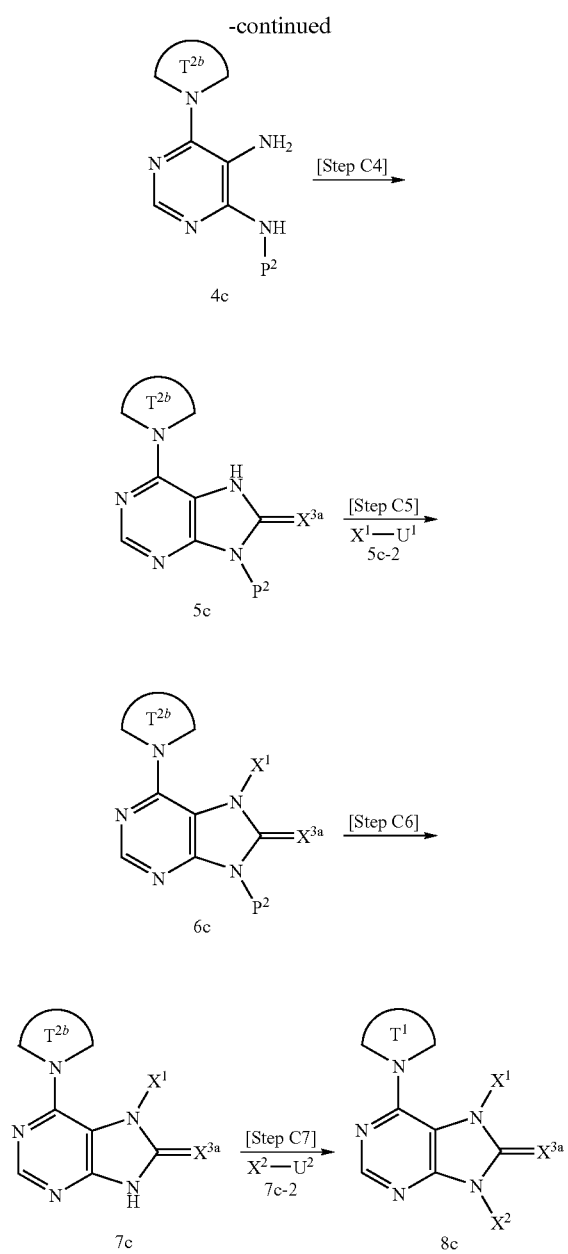

presence or absence of a base such as triethylamine, sodium bicarbonate, or potassium carbonate, at a temperature in the range of 0° C. to 150° C.

[Step C3]

This is a step for obtaining compound (4c) by reducing the nitro group of compound (3c).

The reaction conditions are not particularly limited, and for example catalytic reduction can be performed using a metal catalyst under hydrogen atmosphere or in the presence of 2 to 3 times the amount of hydrazine. Methanol, ethanol, N,N-dimethylformamide, tetrahydrofuran, 1,2-dimethoxyethane, 1,4-dioxane, water, and mixed solvents thereof may be used as the solvent. Palladium carbon, platinum oxide, Raney nickel, or such may be used as the metal catalyst. Use of the metal catalyst at a mass ratio of 0.5 to 20% relative to compound (3c) is preferred. The reaction can be performed at a temperature in the range of 0° C. to 150° C.

[Step C4]

This is a step for converting compound (4c) into compound (5c).

The reaction conditions are not particularly limited, and the reaction can be performed in a solvent such as acetonitrile, tetrahydrofuran, ethanol, methanol, 1,4-dioxane, toluene, or xylene, in the presence or absence of a base such as triethylamine, sodium bicarbonate, or potassium carbonate, with N,N'-disuccinimidyl carbonate, carbonyldiimidazole, triphosgene, thiocarbonyldiimidazole, and such, at a temperature in the range of 0° C. to 150° C. The use of 1 to 10 times the amount of N,N'-disuccinimidyl carbonate is preferred.

[Step C5]

This is a step for obtaining compound (6c) by performing a substitution reaction between compound (5c) and compound (5c-2) to introduce a substituent to the amino group at position 7 of compound (5c).

Reaction conditions similar to those of Production method A [Step A1] can be used.

[Step C6]

This is a step for obtaining compound (7c) by removing protecting group $P^2$ on the amino group at position 9 of compound (6c).

The reaction conditions used differ depending on the protecting group used, and for example, when the protecting group is a cyanoethyl group, the compound can be obtained in methanol, or a mixed solution of methanol and tetrahydrofuran, by the action of a base such as sodium methoxide or sodium hydride, at a temperature in the range of 0° C. to 150° C. In this case, the use of 1 to 10 times the amount of the base relative to compound (6c) is preferred.

[Step C7]

This is a step for obtaining compound (8c) by performing a substitution reaction between compound (7c) and compound (7c-2) to introduce a substituent to the amino group at position 9 of compound (7c). Reaction conditions similar to those of Production method A [Step A5] can be used.

When compound (1c-2), containing an amino group protected by a protecting group such as a t-butoxycarbonyl group, is introduced in [Step C1], [Step C7] is followed by deprotection. Deprotection reaction conditions similar to those of Production method A [Step A7] may be used.

[Step C1]

This is a step for obtaining compound (2c) by reacting 4,6-dichloro-5-nitropyrimidine (1c) [CAS No. 4316-93-2] with compound (1c-2). Reaction conditions similar to those of Production method A [Step A6] may be used.

[Step C2]

This is a step for obtaining compound (3c) by reacting compound (2c) with amine (2c-2) that has a $P^2$-protected amino group. Herein, the use of 1 to 10 times the amount of amine (2c-2) is desirable.

The reaction conditions are not particularly limited, and the reaction can be performed by mixing compound (2c) and compound (2c-2) with or without a solvent such as N,N-dimethylformamide, N-methylpyrrolidone, methanol, ethanol, 1,4-dioxane, acetonitrile, toluene, or xylene, and in the Production Method C-2

Production Method D

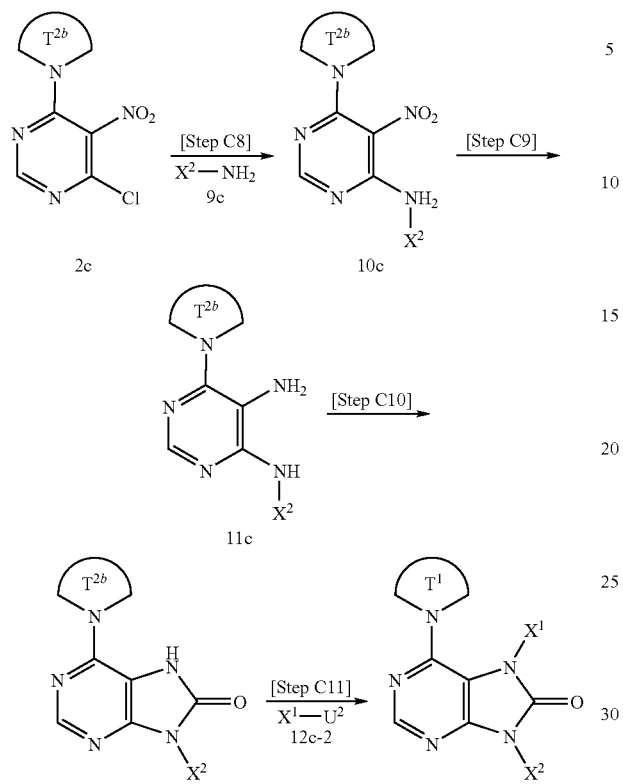

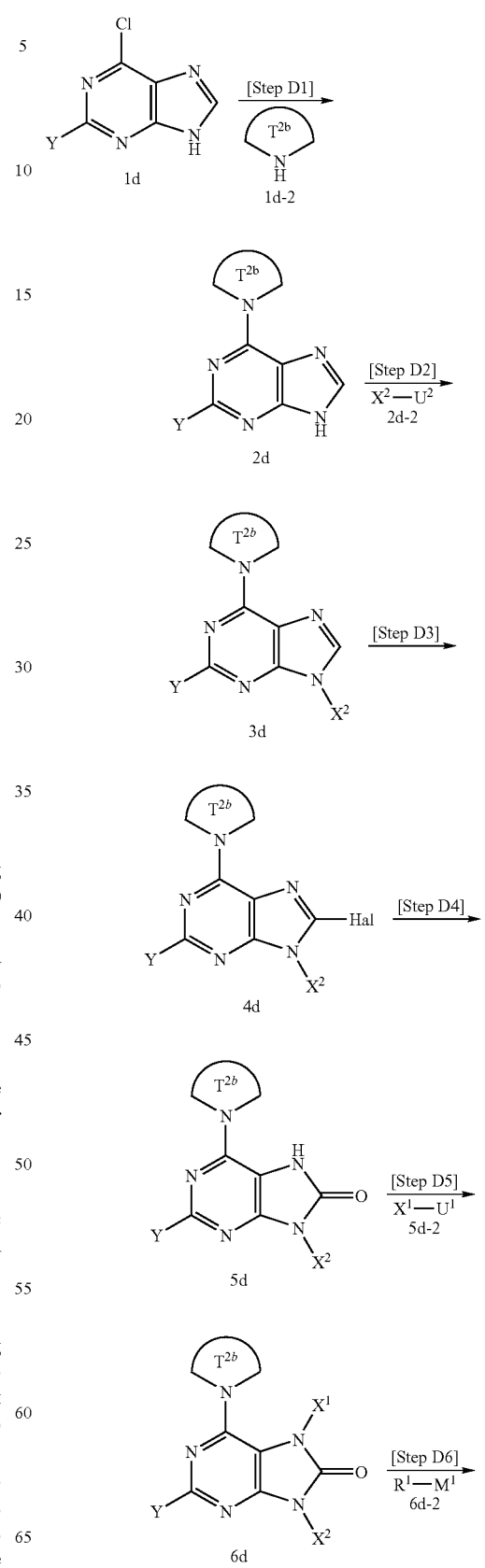

[Step C8]

This is a step for obtaining compound (10c) by reacting compound (2c) with amine (9c). In this case, the use of 1 to 10 times the amount of amine (9c) is desirable.

The reaction conditions are not particularly limited, and conditions similar to those of Production method C-1 [Step C2] may be used.

[Step C9]

This is a step for obtaining compound (11c) by reducing the nitro group of compound (10c). Reaction conditions similar to those of Production method C [Step C3] may be used.

[Step C10]

This is a step for converting compound (11c) into cyclic urea (12c). Reaction conditions similar to those of Production method C [Step C4] may be used.

[Step C11]

This is a step for obtaining compound (13c) by performing a substitution reaction between compound (12c) and compound (12c-2) to introduce a substituent to the amino group at position 7 of compound (12c). Reaction conditions similar to those of Production method A [Step A1] may be used.

When $T^{2b}$ contains an amino group protected by a protecting group such as a t-butoxycarbonyl group, [Step C11] is followed by deprotection. Deprotection reaction conditions similar to those of Production method A [Step A7] may be used.

-continued

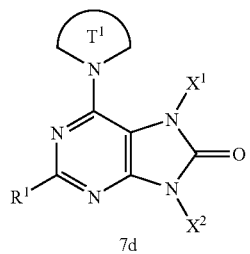

7d

[Step D1]

This is a step for obtaining compound (2d) by reacting compound (1d) with compound (1d-2). Reaction conditions similar to those of Production method A [Step A6] may be used.

[Step D2]

This is a step for obtaining compound (3d) by performing a substitution reaction between compound (2d) and compound (2d-2) to introduce a substituent to the amino group at position 9 of compound (2d). Reaction conditions similar to those of Production method A [Step A5] may be used.

[Step D3]

This is a step for obtaining compound (4d) by reacting compound (3d) with a halogenation reagent. Reaction conditions similar to those of Production method A [Step A2] may be used.

[Step D4]

This is a step for obtaining compound (5d) by hydrolysis of compound (4d). Reaction conditions similar to those of Production method A [Step A4] may be used.

[Step D5]

This is a step for obtaining compound (6d) by introducing a substituent to the amino group at position 7 of compound (5d). Reaction conditions similar to those of Production method A [Step A1] may be used.

[Step D6]

When Y is a halogen group such as a chlorine atom, a substituent can be introduced at position 2 of compound (6d). This is a step for obtaining compound (7d) by performing a substitution reaction between compound (6d) and compound (6d-2) to introduce a substituent at position 2 of compound (6d). Reaction conditions similar to those of Production method A [Step A7] may be used. When Y is a hydrogen atom, this step is omitted.

In [Step D1], when compound (1d-2) containing an amino group protected by a protecting group such as a t-butoxycarbonyl group is introduced, [Step D6] is followed by deprotection. Deprotection reaction conditions similar to those of Production method A [Step A7] may be used.

Production Method E

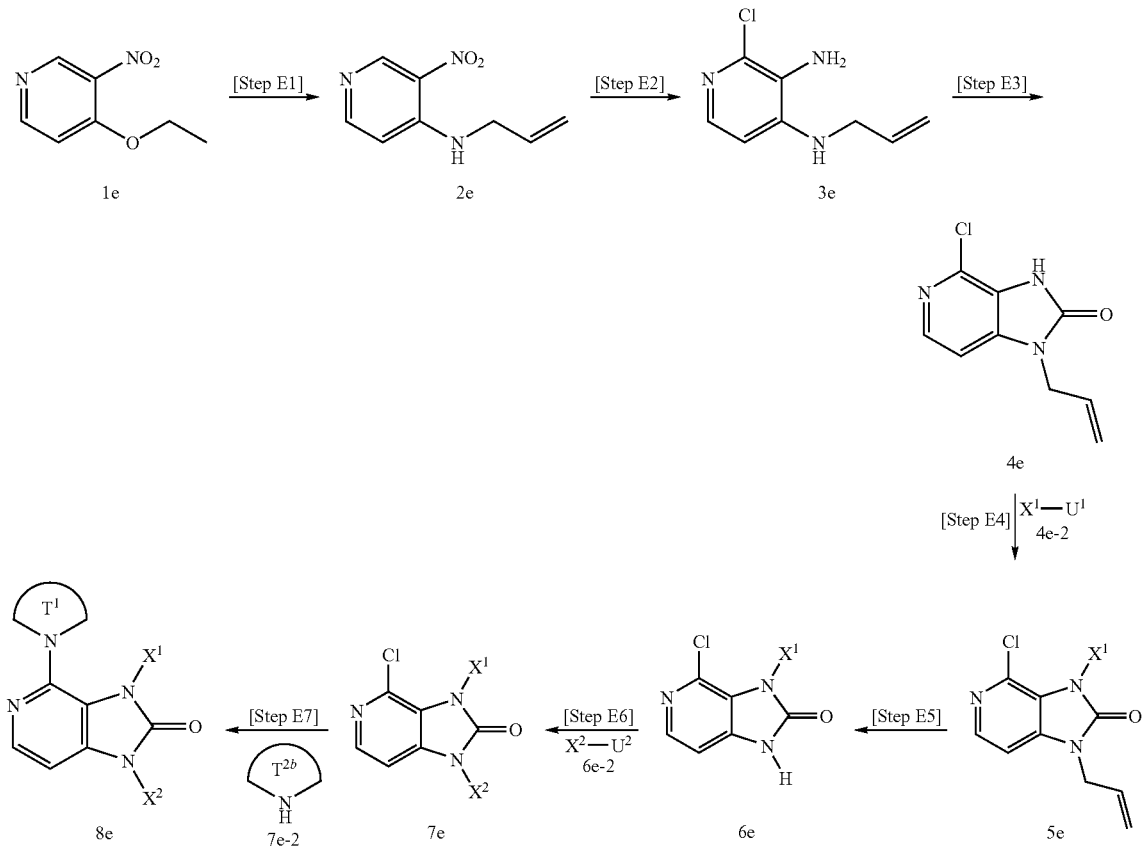

[Step E1]

This is a step for obtaining compound (2e) by reacting 4-ethoxy-3-nitropyridine hydrochloride (1e) [CAS No. 94602-04-7] with allylamine. In this case, the use of 1 to 20 times the amount of allylamine relative to compound (1 e) is preferred.

The reaction can be performed at a temperature in the range of 20° C. to 150° C. Methanol, ethanol, water, or a mixed solvent thereof may be used as the reaction solvent.

[Step E2]

This is a step for obtaining compound (3e) by subjecting compound (2e) to reductive chlorination.

Tin salts such as tin chloride may be used as the reducing agent. In this case, the use of 4 to 20 times the amount of reducing agent relative to compound (2e) is preferred. Con-

[Step E6]

This is a step for obtaining compound (7e) by reacting compound (6e) with compound (6e-2) to introduce a substituent to the amino group at position 1 of compound (6e). Reaction conditions similar to those of Production method A [Step A5] may be used.

[Step E7]

This is a step for obtaining compound (8e) by reacting compound (7e) with compound (7e-2). Reaction conditions similar to those of Production method A [Step A6] may be used.

In [Step E7], when compound (7e-2) containing an amino group protected by a protecting group such as a t-butoxycarbonyl group, is introduced, [Step E7] is followed by deprotection. Deprotection reaction conditions similar to those of Production method A [Step A7] may be used.

Production Method F

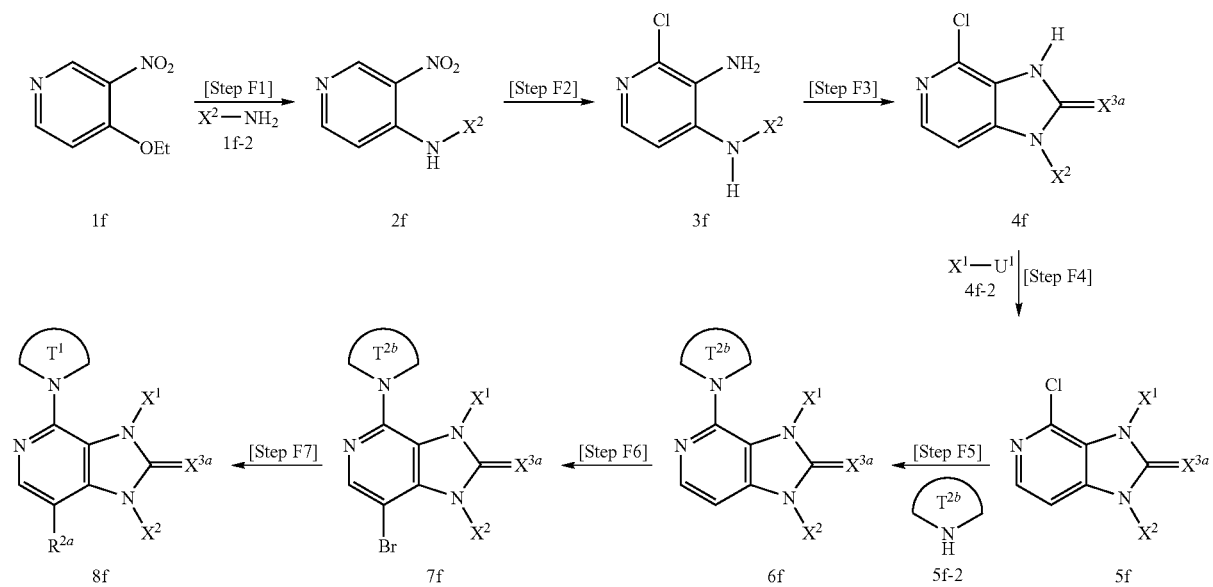

centrated hydrochloric acid can be used as the solvent. The reaction can be performed at a temperature in the range of 20° C. to 150° C.

[Step E3]

This is a step for converting compound (3e) into cyclic urea (4e). Reaction conditions similar to those of Production method C [Step C4] may be used.

[Step E4]

This is a step for obtaining compound (5e) by reacting compound (4e) with compound (4e-2). Reaction conditions similar to those of Production method A [Step A1] may be used.

[Step E5]

This is a step for obtaining compound (6e) by dissociating the allyl group of compound (5e).

The reaction conditions are not particularly limited, and compound (6e) can be obtained by the action of osmic acid and sodium periodate in a solvent such as tetrahydrofuran, 1,4-dioxane, 1,2-dimethoxyethane, or water at 20° C. to 100° C.

[Step F1]

This is a step for obtaining compound (2f) by reacting compound (1f) with compound (1f-2).

The reaction can be performed at a temperature in the range of 20° C. to 150° C. Methanol, ethanol, water, a mixed solvent thereof, or such may be used as the reaction solvent. In this case, the use of 5 to 100 times the amount of compound (1f-2) relative to compound (1f) is preferred.

[Step F2]

This is a step for obtaining compound (3f) by subjecting compound (2f) to reductive chlorination. Reaction conditions similar to those of Production method E [Step E2] may be used.

[Step F3]

This is a step for converting compound (3f) into compound (4f). Reaction conditions similar to those of Production method C [Step C4] may be used.

[Step F4]

This is a step for obtaining compound (5f) by introducing a substituent to the amino group at position 3 of compound (4f). Reaction conditions similar to those of Production method A [Step A1] may be used.

[Step F5]

This is a step for obtaining compound (6f) by reacting compound (5f) with compound (5f-2). Reaction conditions similar to those of Production method A [Step A6] may be used.

[Step F6]

This is a step for obtaining compound (7f) by reacting a halogenation reagent with compound (6f). Reaction conditions similar to those of Production method A [Step A2] may be used.

[Step F7]

This is a step for obtaining compound (8f) by reacting a nucleophilic agent with compound (7f) in the presence of a catalyst and a base.

Derivatives of phenol or aniline or such can be used as the nucleophilic agent, and the use of 1 to 3 times the amount of nucleophilic agent relative to compound (7f) is preferred. Cesium carbonate and such may be used as the base, and the use of 1 to 3 times the amount of base relative to compound (7f) is preferred. A copper catalyst such as copper (I) chloride, and 2,2,6,6-tetramethyl-3,5-heptadione may be used as the catalyst, and the use of 0.001 to 0.2 times the amount of each is preferred. 1-methyl-2-pyrrolidone, N,N-dimethylformamide, and such may be used as the reaction solvent. The reaction can be performed in the range of 20° C. to 150° C.

In [Step F5], when compound (5f-2) that contains an amino group protected by a protecting group such as a t-butoxycarbonyl group, is introduced, [Step F7] is followed by deprotection. Deprotection reaction conditions similar to those of Production method A [Step A7] may be used.

The methods indicated above are representative methods for producing compound (1) of the present invention. The starting compounds and various reagents to be used in the methods for producing compounds of the present invention may be salts or hydrates, or solvates depending on the types of starting materials, solvents to be used, or such, and are not limited as long as they do not inhibit the reactions. The types of solvents to be used depend on the types of starting compounds, reagents to be used, or such, and are not limited as long as they do not inhibit the reactions and dissolve starting materials to some extent. When a compound (1) of the present invention is obtained in a free form, it can be converted by conventional methods to a salt or hydrate, which are possible forms of the above-mentioned compound (1).

When compound (I) of the present invention is obtained as a salt or hydrate, such a product can be converted by a conventional method to a free form of the above-described compound (I).

In addition, various isomers of compound (I) of the present invention (for example, geometric isomers, enantiomers due to asymmetric carbons, rotamers, stereoisomers, and tautomers) can be purified and isolated by typical means for isolation, examples of which include recrystallization, diastereomer salt methods, enzyme-based separation, and various chromatographic methods (for example, thin layer chromatography, column chromatography, and gas chromatography).

Compounds of the present invention, salts thereof, or hydrates thereof, can be formulated by conventional methods into tablets, powders, particles, granules, coated tablets, capsules, syrups, troches, inhalants, suppositories, injections, ointments, eye ointments, eye drops, nasal drops, ear drops, epithem, lotions, etc. Such formulations can be achieved using typical diluting agents, binders, lubricants, colorants, flavoring agents, and if required, stabilizers, emulsifiers, absorbefacients, surfactants, pH modulators, preservatives, antioxidants, etc., and materials commonly used as ingredients of pharmaceutical preparations according to conventional methods. For example, an oral preparation can be produced by combining a compound of the present invention, or a pharmaceutically acceptable salt thereof, with a diluting agent, and if required, a binder, disintegrating agent, lubricant, colorant, flavoring agent, or such, and formulating the mixture into powders, particles, granules, tablets, coated tablets, capsules, or the like, according to conventional methods. Examples of the materials include, for example, animal and vegetable oils such as soya bean oil, beef tallow, and synthetic glyceride; hydrocarbons such as liquid paraffin, squalane, and solid paraffin; ester oils such as octyldodecyl myristate and isopropyl myristate; higher alcohols such as cetostearyl alcohol and behenyl alcohol; silicon resins; silicone oils; surfactants such as polyoxyethylene fatty acid ester, sorbitan fatty acid ester, glycerol fatty acid ester, polyoxyethylene sorbitan fatty acid ester, polyoxyethylene hydrogenated castor oil, and polyoxyethylene polyoxypropylene block co-polymer; water-soluble polymers such as hydroxyethyl cellulose, poly-acrylic acid, carboxyvinyl polymer, polyethylene glycol, polyvinylpyrrolidone, and methyl cellulose; lower alcohols such as ethanol and isopropanol; polyhydric alcohols such as glycerol, propylene glycol, dipropylene glycol, and sorbitol; sugars such as glucose and sucrose; inorganic powder such as anhydrous silicic acid, magnesium aluminum silicate, and aluminum silicate; and pure water. Diluting agents include, for example, lactose, corn starch, white sugar, glucose, mannitol, sorbitol, crystal cellulose, and silicon dioxide. Binders include, for example, polyvinyl alcohol, polyvinyl ether, methyl cellulose, ethyl cellulose, gum arabic, tragacanth, gelatin, shellac, hydroxypropyl methyl cellulose, hydroxypropyl cellulose, polyvinylpyrrolidone, polypropylene glycol-polyoxyethylene block co-polymer, and meglumine. Disintegrating agents include, for example, starch, agar, gelatin powder, crystalline cellulose, calcium carbonate, sodium bicarbonate, calcium citrate, dextrin, pectin, and calcium carboxymethyl cellulose. Lubricants include, for example, magnesium stearate, talc, polyethylene glycol, silica, and hydrogenated vegetable oil. Colorants include pharmaceutically acceptable colorants. Flavoring agents include cocoa powder, peppermint camphor, aromatic powders, peppermint oil, Borneo camphor, and cinnamon powder. Tablets and granules may be coated with sugar, or other appropriate coatings can be made as required. Solutions such as syrups or injectable preparations can be formulated by combining a compound of the present invention, or a pharmaceutically acceptable salt thereof, with a pH modulator, a solubilizing agent, an isotonizing agent, or such, and if required, with an auxiliary solubilizing agent, a stabilizer, or the like, according to conventional methods. Methods for producing an external preparation are not limited, and such preparations can be produced by conventional methods. Specifically, various materials typically used for producing pharmaceuticals, quasi drugs, cosmetics, and such can be used as base materials for external formulations. Specifically, base materials to be used include, for example, animal and vegetable oils, mineral oils, ester oils, waxes, higher alcohols, fatty acids, silicone oils, surfactants, phospholipids, alcohols, polyhydric alcohols, water-soluble polymers, clay minerals, and pure water. Furthermore, external preparations of the present invention can contain, as required, pH modulators, antioxidants, chelating agents, antibacterial/antifungal agents, coloring agents, odoriferous substances, etc. But this does not limit the type of base materials that are to be used in external preparations of the present invention. If required, the preparations may contain differentiation inducers, blood flow improving agents, antimicrobial agents, antiphlogistics, cell activators, vitamins, amino acids, humectants, keratolytic agents, etc. The amount of base materials listed above is adjusted within a concentration range used for producing typical external preparations.

When a compound of the present invention, or a salt thereof, or a hydrate thereof is administered, the forms of a compound are not limited and a compound can be given orally or parenterally by a conventional method. For example, a compound can be administered as a dosage form such as a tablet, powder, granule, capsule, syrup, troche, inhalant, suppository, injection, ointment, eye ointment, eye drop, nasal drop, ear drop, epithem, and lotion. The dose of a pharmaceutical of the present invention can be selected appropriately based on symptom severity, age, sex, weight, compound form, salt type, specific type of disease, etc.

The dose varies depending on the patient's disease, symptom severity, age, sex, and drug susceptibility, etc. A pharmaceutical agent of this invention is administered once or several times at a dose of approximately 0.03 to approximately 1000 mg/adult/day, preferably 0.1 to 500 mg/adult/day, more preferably 0.1 to 100 mg/adult/day. An injection can be given at a dose of approximately 1 to approximately 3000 μg/kg, preferably approximately 3 to approximately 1000 μg/kg.

BEST MODE FOR CARRYING OUT THE INVENTION

The compounds of this invention can be produced, for example, by methods described in the following Examples. However, these Examples are only provided to illustrate the compounds, and the compounds of this invention are not to be construed as being limited thereto under any circumstance. The phrase "purification by reverse phase high performance liquid chromatography" that appears in this description means reverse phase high performance liquid chromatographic purification that uses an acetonitrile-water mobile phase (containing 0.1% trifluoroacetic acid), unless there is a specific description.

Hereinafter, the number in front of the name of the compound indicates the Example number and also the compound number.

EXAMPLE 1

7-(2-Butynyl)-2-methoxy-9-methyl-6-(piperazin-1-yl)-7,9-dihydropurin-8-one trifluoroacetic acid salt 1a 7-(2-Butynyl)-3-methyl-3,7-dihydropurine-2,6-dione

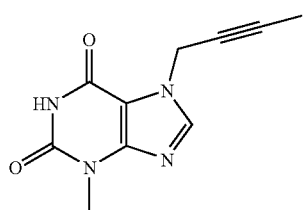

1-Bromo-2-butyne (55.3 mL) and anhydrous potassium carbonate (84.9 g) were added to a mixture of 3-methylxanthine [CAS No. 1076-22-8] (100 g) and N,N-dimethylformamide (1000 mL), and this reaction solution was stirred at room temperature for 18 hours. After completion of the reaction, water (1000 mL) was added to the reaction solution, this was stirred at room temperature for one hour, and then the white precipitate was collected by filtration. The white solid obtained was washed with water and t-butyl methyl ether to give the title compound (112 g).

¹H-NMR (DMSO-d6)

δ 1.82 (t, J=2.2 Hz, 3H), 3.34 (s, 3H), 5.06 (q, J=2.2 Hz, 2H), 8.12 (s, 1H), 11.16 (br.s, 1H)

1b 7-(2-Butynyl)-8-chloro-3-methyl-3,7-dihydropurine-2,6-dione

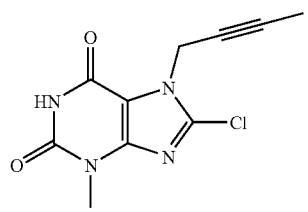

7-(2-Butynyl)-3-methyl-3,7-dihydropurine-2,6-dione (112 g) was dissolved in N,N-dimethylformamide (2200 mL), then N-chlorosuccinimide (75.3 g) was added to this mixture, and the reaction solution was stirred at room temperature for five hours. After completion of the reaction, water (2200 mL) was added to the reaction solution, this was stirred at room temperature for 1.5 hours. A white precipitate was then collected by filtration. The white solid obtained was washed with water and t-butyl methyl ether to give the title compound (117 g).

¹H-NMR (DMSO-d6)

δ 1.78 (t, J=2.0 Hz, 3H), 3.30 (s, 3H), 5.06 (q, J=2.0 Hz, 2H), 11.34 (br.s, 1H)

1c 7-(2-Butynyl)-2,6,8-trichloro-7H-purine

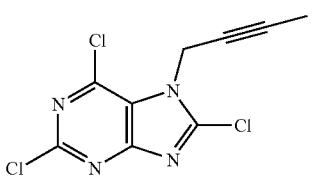

A mixture of 7-(2-butynyl)-8-chloro-3-methyl-3,7-dihydropurine-2,6-dione (2.52 g) and phosphorus oxychloride (100 mL) was stirred at 120° C. for 14 hours. The reaction solution was cooled to room temperature, then phosphorus pentachloride (4.15 g) was added, and the reaction solution was stirred again at 120° C. for 24 hours. The reaction solution was cooled to room temperature, the solvent was distilled off under reduced pressure, and the residue was dissolved in tetrahydrofuran. This reaction mixture was poured into a saturated aqueous solution of sodium bicarbonate, and extracted using ethyl acetate. The obtained organic layer was washed sequentially with water and saturated brine, and then dried over anhydrous magnesium sulfate. The organic layer was concentrated under reduced pressure, and the residue was purified by silica gel column chromatography (ethyl acetate: hexane=1:3), to give the title compound (2.40 g).

$^1$H-NMR (CDCl$_3$)

δ 1.82 (t, J=2.4 Hz, 3H), 5.21 (q, J=2.4 Hz, 2H)

1d 7-(2-Butynyl)-2,6-dichloro-7,9-dihydropurin-8-one

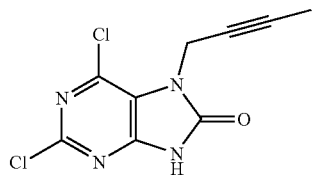

7-(2-Butynyl)-2,6,8-trichloro-7H-purine (1.0 g) was dissolved in dimethylsulfoxide (20 mL), and then sodium acetate (595 mg) and sodium bicarbonate (366 mg) were added to the mixture. This reaction solution was stirred at room temperature for 12 hours, and then 1 N of aqueous hydrochloric acid solution (5.0 mL) and 80 mL of water were added. This reaction solution was stirred at room temperature for one hour, and then a white precipitate was collected by filtration. The white solid obtained was washed with water and t-butyl methyl ether to give the title compound (800 mg).

$^1$H-NMR (DMSO-d6)

δ 1.79 (t, J=2.4 Hz, 3H), 4.70 (q, J=2.4 Hz, 2H), 12.95 (br.s, 1H)

MS m/e (ESI) 257 (MH$^+$)

1e 7-(2-Butynyl)-2,6-dichloro-9-methyl-7,9-dihydropurin-8-one

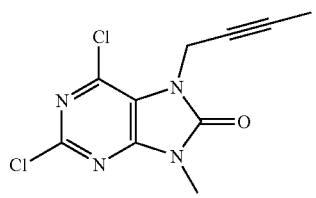

7-(2-Butynyl)-2,6-dichloro-7,9-dihydropurin-8-one (435 mg) was dissolved in N,N-dimethylformamide (10 mL), and then methyl iodide (158 μL) and anhydrous potassium carbonate (468 mg) were added to the solution. This reaction solution was stirred at room temperature for 12 hours, and then water (50 mL) was added. After stirring at room temperature for one hour, a white precipitate was collected by filtration. The white solid obtained was washed with water and t-butyl methyl ether to give the title compound (355 mg).

$^1$H-NMR (DMSO-d6)

δ 1.78 (t, J=2.4 Hz, 3H), 3.33 (s, 3H), 4.76 (q, J=2.4 Hz, 2H)

MS m/e (ESI) 271 (MH$^+$)

1f

4-[7-(2-Butynyl)-2-chloro-9-methyl-8-oxo-8,9-dihydro-7H-purin-6-yl]piperazine-1-carboxylic acid t-butyl ester

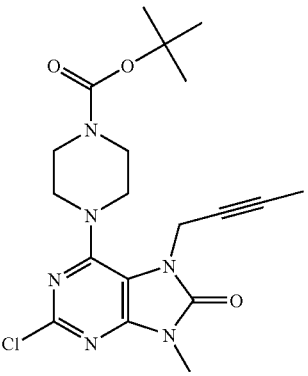

7-(2-Butynyl)-2,6-dichloro-9-methyl-7,9-dihydropurin-8-one (334 mg) was dissolved in acetonitrile (5 mL), piperazin-1-carboxylic acid t-butyl ester (300 mg) and triethylamine (190 μL) were added, and this reaction solution was stirred at room temperature for 96 hours. After completion of the reaction, 1 N hydrochloric acid (3 mL) and water (10 mL) were added to the reaction solution, and this was extracted with ethyl acetate. The obtained organic layer was washed sequentially with water and saturated brine, and dried over anhydrous magnesium sulfate. The resulting organic layer was concentrated under reduced pressure, and the residue was purified by silica gel column chromatography (ethyl acetate: hexane=1:3) to give the title compound (312 mg).

$^1$H-NMR (DMSO-d6)

δ 1.47 (s, 9H), 1.77 (t, J=2.4 Hz, 3H), 3.33-3.36 (m, 4H), 3.41 (s, 3H), 3.56-3.60 (m, 4H), 4.63 (q, J=2.4 Hz, 2H)

1 g 7-(2-Butynyl)-2-methoxy-9-methyl-6-(piperazin-1-yl)-7,9-dihydropurin-8-one trifluoroacetic acid salt

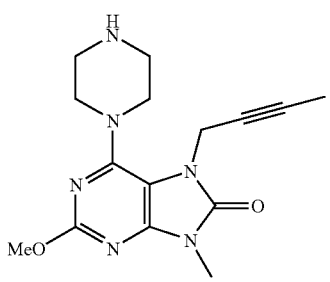 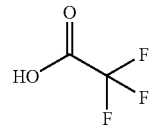

4-[7-(2-Butynyl)-2-chloro-9-methyl-8-oxo-8,9-dihydro-7H-purin-6-yl]piperazine-1-carboxylic acid t-butyl ester (8 mg) was dissolved in methanol (0.5 mL), and then sodium hydride (60-72%, in oil) (5 mg) was added to this solution. After stirring at 80° C. for four hours, saturated aqueous ammonium chloride was added to the reaction solution, and this was extracted with ethyl acetate. The obtained organic layer was concentrated, and the residue was dissolved in trifluoroacetic acid. This reaction solution was stirred at room temperature for five minutes, and then concentrated. The residue was purified by reverse phase high performance liquid chromatography to give the title compound (4.26 mg).

$^1$H-NMR (CD$_3$OD)

δ 1.78 (t, J=2.4 Hz, 3H), 3.37 (s, 3H), 3.41-3.45 (m, 4H), 3.60-3.64 (m, 4H), 3.97 (s, 3H), 4.66 (q, J=2.4 Hz, 2H)

MS m/e (ESI) 317(M+H)$^+$

EXAMPLE 2

7-(2-Butynyl)-2-chloro-9-methyl-6-(piperazin-1-yl)-7,9-dihydropurin-8-one trifluoroacetic acid salt

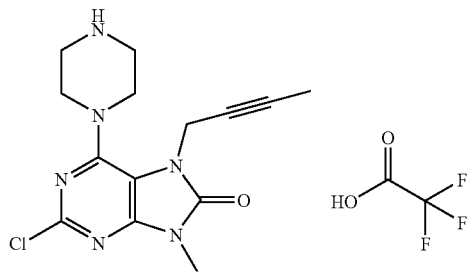

4-[7-(2-Butynyl)-2-chloro-9-methyl-8-oxo-8,9-dihydro-7H-purin-6-yl]piperazine-1-carboxylic acid t-butyl ester (compound 1f) (15 mg) was dissolved in trifluoroacetic acid (1 mL). This reaction solution was stirred at room temperature for five minutes, and then concentrated. The residue was purified by reverse phase high performance liquid chromatography to give the title compound (11.07 mg).

MS m/e (ESI) 321(M+H)$^+$

EXAMPLE 3

7-(2-Butynyl)-2-diethylamino-9-methyl-6-(piperazin-1-yl)-7,9-dihydropurin-8-one trifluoroacetic acid salt

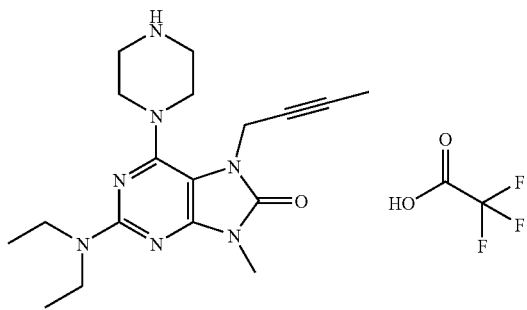

4-[7-(2-Butynyl)-2-chloro-9-methyl-8-oxo-8,9-dihydro-7H-purin-6-yl]piperazine-1-carboxylic acid t-butyl ester (compound 1f) (4 mg) was dissolved in 1-methyl-2-pyrrolidone (0.3 mL), and then diethyl amine (50 μL) was added to this solution. The reaction solution was stirred at 80° C. for four hours, and then concentrated. The residue was dissolved in trifluoroacetic acid, and this reaction solution was stirred at room temperature for five minutes, and then concentrated. The residue was purified by reverse phase high performance liquid chromatography to give the title compound (0.63 mg).

MS m/e (ESI) 358(M+H)$^+$

EXAMPLE 4

7-(2-Butynyl)-2-dimethylamino-9-methyl-6-(piperazin-1-yl)-7,9-dihydropurin-8-one trifluoroacetic acid salt

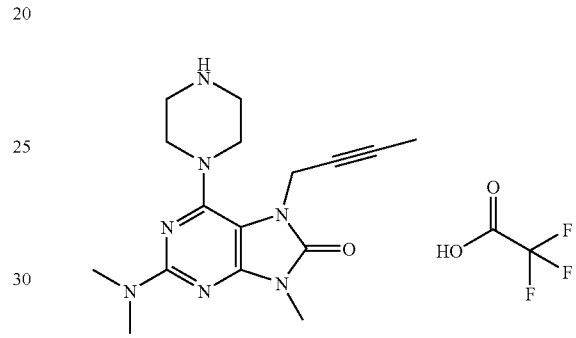

Using 4-[7-(2-butynyl)-2-chloro-9-methyl-8-oxo-8,9-dihydro-7H-purin-6-yl]piperazine-1-carboxylic acid t-butyl ester (10 mg) and dimethylamine (30 μL) instead of the diethylamine in Example 3, the title compound (5.96 mg) was obtained by treatment similar to that of Example 3.

MS m/e (ESI) 330(M+H)$^+$

EXAMPLE 5

7-(2-Butynyl)-9-methyl-2-methylamino-6-(piperazin-1-yl)-7,9-dihydropurin-8-one trifluoroacetic acid salt

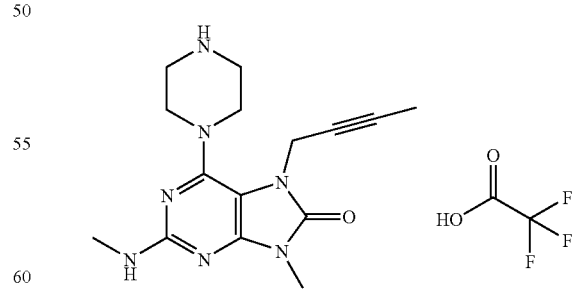

Using methylamine (40% methanol solution) (50 μL) instead of the diethylamine in Example 4, the title compound (4.35 mg) was obtained by treatment similar to that of Example 4.

MS m/e (ESI) 316(M+H)$^+$

EXAMPLE 6

2-Amino-7-(2-butynyl)-9-methyl-6-(piperazin-1-yl)-7,9-dihydropurin-8-one trifluoroacetic acid salt

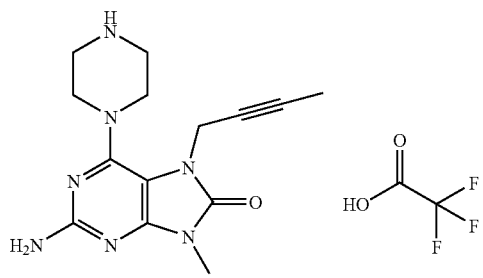

Using aqueous ammonia (28%-30%) (30 µL) instead of the diethylamine in Example 4, the title compound (0.84 mg) was obtained by treatment similar to that of Example 4.

EXAMPLE 7

7-(2-Butynyl)-2-isopropoxy-9-methyl-6-(piperazin-1-yl)-7,9-dihydropurin-8-one trifluoroacetic acid salt

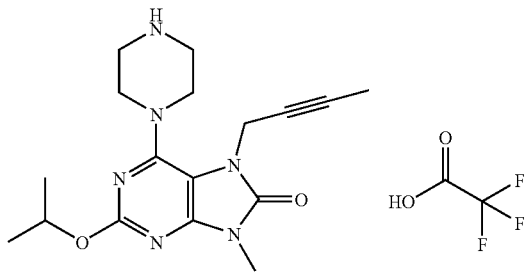

4-[7-(2-Butynyl)-2-chloro-9-methyl-8-oxo-8,9-dihydro-7H-purin-6-yl]piperazine-1-carboxylic acid t-butyl ester (compound 1f) (5 mg) was dissolved in isopropanol (0.5 mL), and then sodium hydride (60%-72%, in oil) (5 mg) was added to this solution. The reaction solution was stirred at 80° C. for four hours, saturated aqueous ammonium chloride solution was added to the reaction solution, and this was extracted with ethyl acetate. The obtained organic layer was concentrated, the residue was dissolved in trifluoroacetic acid, and this reaction solution was stirred at room temperature for five minutes, and then concentrated. The residue was purified by reverse phase high performance liquid chromatography to obtain the title compound (1.56 mg).

MS m/e (ESI) 345(M+H)$^+$

EXAMPLE 8

7-(2-Butynyl)-2-hydroxy-9-methyl-6-(piperazin-1-yl)-7,9-dihydropurin-8-one trifluoroacetic acid salt

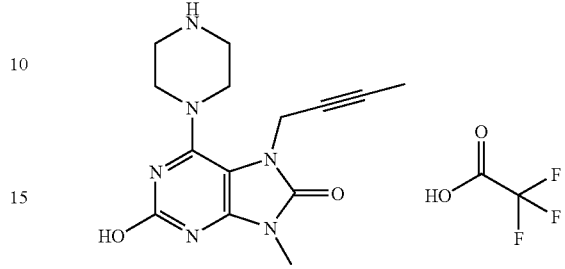

4-[7-(2-Butynyl)-2-chloro-9-methyl-8-oxo-8,9-dihydro-7H-purin-6-yl]piperazine-1-carboxylic acid t-butyl ester (compound 1f) (5 mg) was dissolved in 1-methyl-2-pyrrolidone (0.3 mL), and then 4-methoxybenzyl alcohol (30 µL) and sodium hydride (60%-72%, in oil) (5 mg) were added to this solution. The reaction solution was stirred at 80° C. for four hours, saturated aqueous ammonium chloride solution was added to the reaction solution, and this was extracted with ethyl acetate. The obtained organic layer was concentrated, the residue was dissolved in trifluoroacetic acid, and this reaction solution was stirred at room temperature for five minutes, and then concentrated. The residue was purified by reverse phase high performance liquid chromatography to obtain the title compound (1.56 mg).

MS m/e (ESI) 303(M+H)$^+$

EXAMPLE 9

7-(2-Butynyl)-2-methylsulfanyl-9-methyl-6-(piperazin-1-yl)-7,9-dihydropurin-8-one trifluoroacetic acid salt

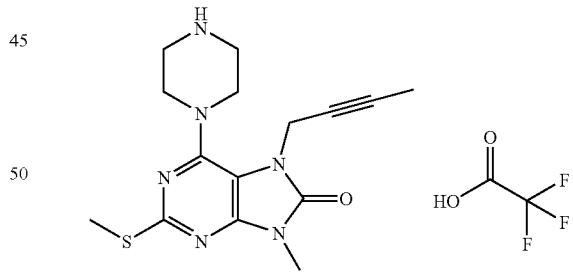

4-[7-(2-Butynyl)-2-chloro-9-methyl-8-oxo-8,9-dihydro-7H-purin-6-yl]piperazine-1-carboxylic acid t-butyl ester (compound 1f) (5 mg) was dissolved in 1-methyl-2-pyrrolidone (0.3 mL), and then methyl mercaptan (30%, methanol solution) (50 µL) and anhydrous potassium carbonate (5 mg) were added to this solution. The reaction solution was stirred at 60° C. for four hours, saturated aqueous ammonium chloride solution was added to the reaction solution, and this was extracted with ethyl acetate. The obtained organic layer was concentrated, the residue was dissolved in trifluoroacetic acid, and this reaction solution was stirred at room temperature for five minutes, and then concentrated. The residue was purified by reverse phase high performance liquid chromatography to give the title compound (1.87 mg).

MS m/e (ESI) 333(M+H)+

EXAMPLE 10

7-(2-Butynyl)-2-ethoxy-9-methyl-6-(piperazin-1-yl)-7,9-dihydropurin-8-one trifluoroacetic acid salt

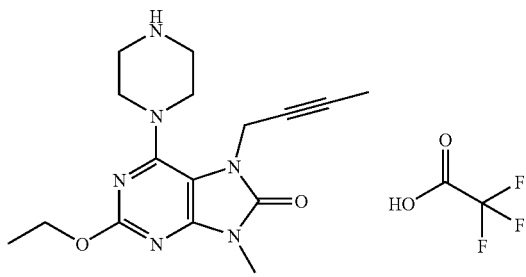

4-[7-(2-Butynyl)-2-chloro-9-methyl-8-oxo-8,9-dihydro-7H-purin-6-yl]piperazine-1-carboxylic acid t-butylester (compound 1f) (15 mg) was dissolved in 1-methyl-2-pyrrolidone (0.3 mL), and then ethanol (300 μL) and cesium carbonate (15 mg) were added to this solution. The reaction solution was stirred at 70° C. for 12 hours, and then concentrated. The residue was dissolved in trifluoroacetic acid, and this reaction solution was stirred at room temperature for five minutes and then concentrated. This residue was purified by reverse phase high performance liquid chromatography to give the title compound (8.50 mg).

$^1$H-NMR (CD$_3$OD)

δ 1.44 (t, J=7.0 Hz, 3H), 1.82 (t, J=2.4 Hz, 3H), 3.40 (s, 3H), 3.47 (m, 4H), 3.65 (m, 4H), 4.44 (2H, J=7.0 Hz, 2H), 4.70 (q, J=2.4 Hz, 2H)

MS m/e (ESI) 331(M+H)+

EXAMPLE 11

2-Benzyloxy-7-(2-butynyl)-9-methyl-6-(piperazin-1-yl)-7,9-dihydropurin-8-one trifluoroacetic acid salt

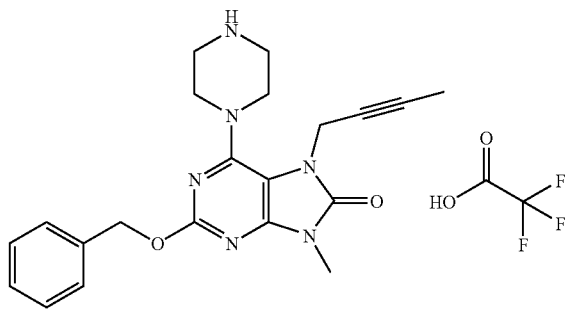

Using benzylalcohol (30 μL) instead of the ethanol in Example 10, the title compound (11.28 mg) was obtained by treatment similar to that of Example 10.

MS m/e (ESI) 393(M+H)+

EXAMPLE 12

7-(2-Butynyl)-9-methyl-2-phenoxy-6-(piperazin-1-yl)-7,9-dihydropurin-8-one trifluoroacetic acid salt

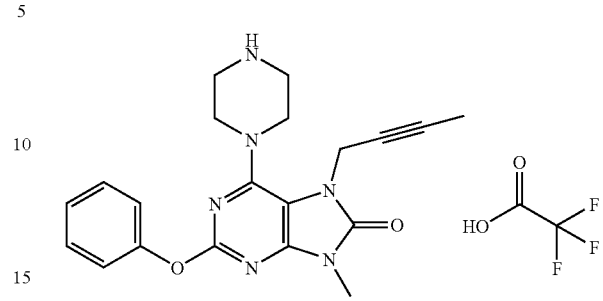

Using phenol (20 mg) instead of ethanol in Example 10, the title compound (11.83 mg) was obtained by the treatment similar to that of Example 10.

MS m/e (ESI) 379(M+H)+

EXAMPLE 13

2-[7-(2-Butynyl)-9-methyl-8-oxo-6-(piperazin-1-yl)-8,9-dihydro-7H-purin-2-yloxy]benzonitrile trifluoroacetic acid salt

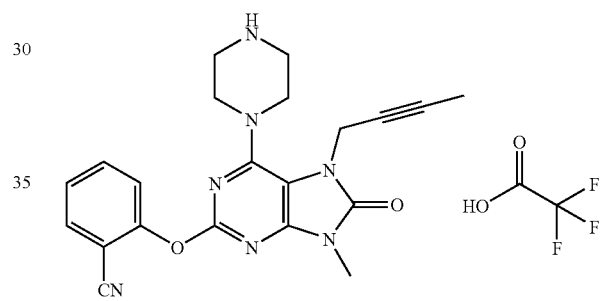

Using 2-cyanophenol (10 mg) instead of the ethanol in Example 10, the title compound (11.83 mg) was obtained by treatment similar to that of Example 10.

MS m/e (ESI) 404(M+H)+

EXAMPLE 14

2-[7-(2-Butynyl)-9-methyl-8-oxo-6-(piperazin-1-yl)-8,9-dihydro-7H-purin-2-yloxy]benzamide trifluoroacetic acid salt

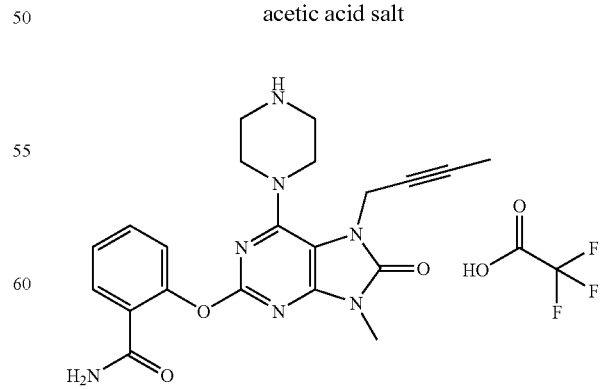

4-[7-(2-Butynyl)-2-chloro-9-methyl-8-oxo-8,9-dihydro-7H-purin-6-yl]piperazine-1-carboxylic acid t-butyl ester (compound 1f) (8 mg) was dissolved in 1-methyl-2-pyrrolidone (0.3 mL), and then salicylamide (10 mg) and cesium carbonate (10 mg) were added to this solution. The reaction solution was stirred at 80° C. for 14 hours, saturated aqueous ammonium chloride solution was added to the reaction solution, and this was extracted with ethyl acetate. The obtained organic layer was concentrated, the residue was dissolved in trifluoroacetic acid, and this reaction solution was stirred at room temperature for five minutes, and then concentrated. The residue was purified by reverse phase high performance liquid chromatography to obtain the title compound (1.54 mg).

MS m/e (ESI) 422(M+H)$^+$

EXAMPLE 15

2-Allyloxy-7-(2-butynyl)-9-methyl-6-(piperazin-1-yl)-7,9-dihydropurin-8-one trifluoroacetic acid salt

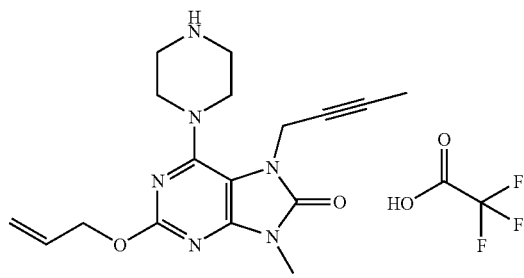

Using allylalcohol (30 μL) instead of the salicylamide in Example 14, the title compound (1.20 mg) was obtained by treatment similar to that of Example 14.

MS m/e (ESI) 343(M+H)$^+$

EXAMPLE 16

7-(2-Butynyl)-2-(2-butynyloxy)-9-methyl-6-(piperazin-1-yl)-7,9-dihydropurin-8-one trifluoroacetic acid salt

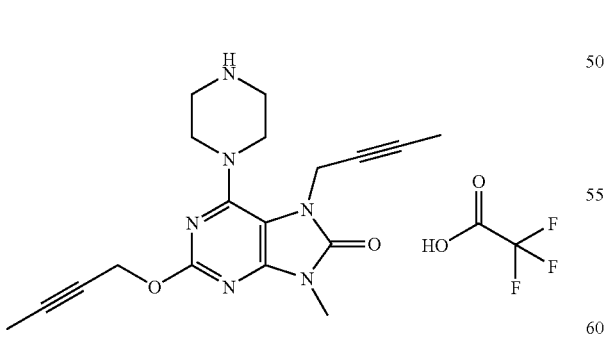

Using 2-butyn-1-ol (30 μL) instead of the salicylamide in Example 16, the title compound (1.20 mg) was obtained by treatment similar to that of Example 14.

MS m/e (ESI) 355(M+H)$^+$

EXAMPLE 17

2-Benzylamino-7-(2-butynyl)-9-methyl-6-(piperazin-1-yl)-7,9-dihydropurin-8-one trifluoroacetic acid salt

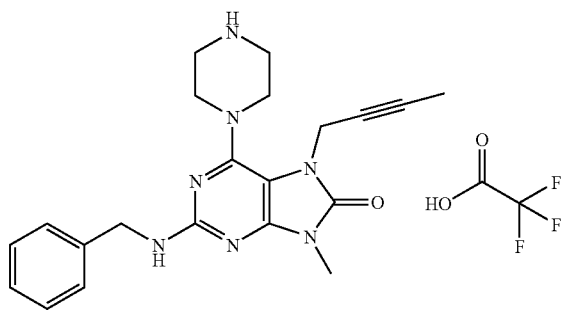

4-[7-(2-Butynyl)-2-chloro-9-methyl-8-oxo-8,9-dihydro-7H-purin-6-yl]piperazin-1-carboxylic acid t-butyl ester (compound 1f) (15 mg) was dissolved in 1-methyl-2-pyrrolidone 0.3 mL, and then benzylamine (50 μL) was added to this solution. The reaction solution was stirred at 70° C. for 12 hours, and then the reaction solution was concentrated. The residue was dissolved in trifluoroacetic acid, and this reaction solution was stirred at room temperature for five minutes, and then concentrated. The residue was purified by reverse phase high performance liquid chromatography to give the title compound (9.78 mg).

MS m/e (ESI) 392(M+H)$^+$

EXAMPLE 18

2-Chloro-9-methyl-7-(2-pentynyl)-6-(piperazin-1-yl)-7,9-dihydropurin-8-one trifluoroacetic acid salt 18a 4-(2-Chloro-9H-purin-6-yl)piperazine-1-carboxylic acid t-butyl ester

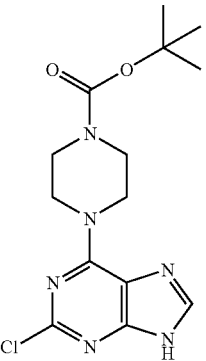

2,6-Dichloropurine [CAS No. 5451-40-1] (5.0 g) was dissolved in acetonitrile (70 mL), and then piperazine-1-carboxylic acid t-butyl ester (4.93 g) and triethylamine (4.1 mL) were added to this solution, and the reaction solution was stirred at room temperature for 22 hours. Water (200 mL) was added to the reaction solution, and this was stirred at room temperature for one hour, and then the white precipitate was collected by filtration. The white solid obtained was washed with water and hexane to give the title compound (8.5 g).

¹H-NMR (DMSO-d6)

δ 1.43 (s, 9H), 3.32 (m, 4H), 3.46 (m, 4H), 8.16 (s, 1H), 13.21 (br.s, 1H)

18b 4-(2-Chloro-9-methyl-9H-purin-6-yl)piperazine-1-carboxylic acid t-butyl ester

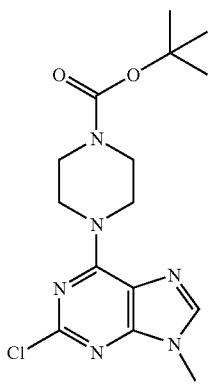

4-(2-Chloro-9H-purin-6-yl)piperazine-1-carboxylic acid t-butyl ester (6.62 g) was dissolved in N,N-dimethylformamide (66 mL), methyl iodide (1.34 mL) and anhydrous potassium carbonate (3.51 g) were added to this solution cooled in an ice bath. After stirring the reaction solution at room temperature for five hours, 1 N hydrochloric acid (5 mL) and water (200 mL) were added to this reaction solution, which was then extracted using ethyl acetate. The obtained organic layer was washed sequentially with water and then saturated brine, and then dried over anhydrous magnesium sulfate. The organic layer was concentrated under reduced pressure to give the title compound as a solid (7.40 g).

¹H-NMR (DMSO-d6)

δ 1.43 (s, 9H), 3.32 (m, 4H), 3.46 (m, 4H), 3.71 (s, 3H), 8.18 (s, 1H)

18c 4-(2,8-Dichloro-9-methyl-9H-purin-6-yl)piperazine-1-carboxylic acid t-butyl ester

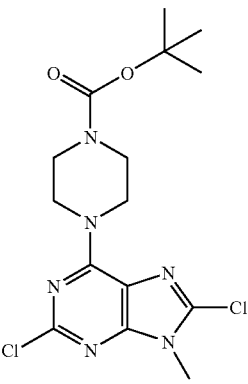

4-(2-Chloro-9-methyl-9H-purin-6-yl)piperazine-1-carboxylic acid t-butyl ester (7.3 g) was dissolved in N,N-dimethylformamide (70 mL), and then N-chlorosuccinimide (2.9 g) was added to this solution. The reaction solution was stirred at room temperature for 23 hours. Water (260 mL) was added to the reaction solution, and this was stirred at room temperature for one hour. A white precipitate was then collected by filtration. The white solid obtained was washed with water and hexane to give the title compound (8.6 g).

¹H-NMR (DMSO-d6)

δ 1.43 (s, 9H), 3.16 (m, 4H), 3.47 (m, 4H), 3.64 (s, 3H)

18d 4-(2-Chloro-9-methyl-8-oxo-8,9-dihydro-7H-purin-6-yl)piperazine-1-carboxylic acid t-butyl ester

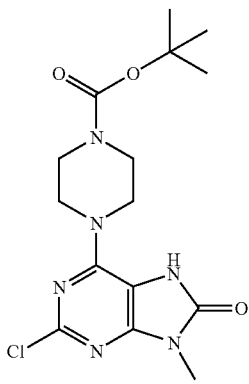

4-(2,8-Dichloro-9-methyl-9H-purin-6-yl)piperazine-1-carboxylic acid t-butyl ester (1.0 g) was dissolved in dimethylsulfoxide (10 mL), and then sodium acetate (425 mg) and sodium bicarbonate (326 mg) were added to this solution. After stirring the reaction solution at 120° C. for 22 hours, 1 N aqueous hydrochloric acid (5.0 mL) and water (80 mL) were added to the reaction solution, and this was extracted with ethyl acetate. The obtained organic layer was washed sequentially with water and saturated brine, and dried over anhydrous magnesium sulfate. The organic layer was then concentrated under reduced pressure, and the residue was purified by silica gel column chromatography to give the title compound (200 mg).

¹H-NMR (DMSO-d6)

δ 1.44 (s, 9H), 3.22 (s, 3H), 3.42 (m, 4H), 3.54 (m, 4H), 11.20 (br.s, 1H)

18e

2-Chloro-9-methyl-7-(2-pentynyl)-6-(piperazin-1-yl)-7,9-dihydropurin-8-one trifluoroacetic acid salt

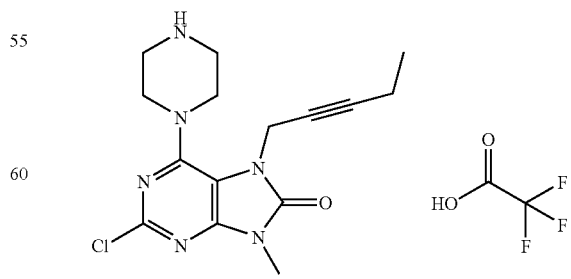

4-(2-Chloro-9-methyl-8-oxo-8,9-dihydro-7H-purin-6-yl)piperazine-1-carboxylic acid t-butyl ester (5 mg) was dissolved in N,N-dimethylformamide (0.2 mL), and then 1-bromo-2-pentyne (15 μL) and anhydrous potassium carbonate (5 mg) were added to this solution. The reaction solution was stirred at room temperature for 12 hours. Saturated aqueous ammonium chloride solution was added to the reaction solution, and this was extracted with ethyl acetate. The organic layer was concentrated, the residue was dissolved in trifluoroacetic acid, and after stirring this reaction solution at room temperature for five minutes, it was concentrated. The residue was purified by reverse phase high performance liquid chromatography to give the title compound (1.93 mg).

¹H-NMR (CD₃OD)

δ 1.09 (t, J=7.6 Hz, 3H), 2.20 (br.q, J=7.6 Hz, 2H), 3.40 (s, 3H), 3.43 (m, 4H), 3.61 (m, 4H), 4.72 (br.s, 2H)

MS m/e (ESI) 335(M+H)⁺

EXAMPLE 19

2-Chloro-9-methyl-7-(3-methyl-2-butenyl)-6-(piperazin-1-yl)-7,9-dihydropurin-8-one trifluoroacetic acid salt

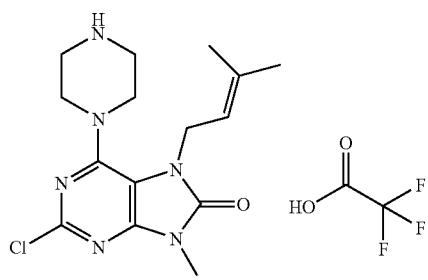

Using 1-bromo-3-methyl-2-butene (15 μL) instead of the 1-bromo-2-pentyne in Example 18e), the title compound (1.25 mg) was obtained by treatment similar to that of Example 18e).

¹H-NMR (CD₃OD)

δ 1.71 (br.s, 3H), 1.80 (br.s, 3H), 3.35 (m, 4H), 3.39 (s, 3H), 3.57 (m, 4H), 4.56 (br.s, 2H), 5.23 (br.s, 1H)

MS m/e (ESI) 337(M+H)⁺

EXAMPLE 20

7-(2-Butenyl)-2-chloro-9-methyl-6-(piperazin-1-yl)-7,9-dihydropurin-8-one trifluoroacetic acid salt

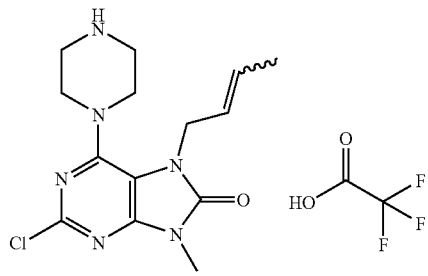

Using 1-bromo-2-butene (15 μL) instead of the 1-bromo-2-pentyne in Example 18e), the title compound (1.84 mg) was obtained by treatment similar to that of Example 18e).

MS m/e (ESI) 323(M+H)⁺

EXAMPLE 21

7-Benzyl-2-chloro-9-methyl-6-(piperazin-1-yl)-7,9-dihydropurin-8-one trifluoroacetic acid salt

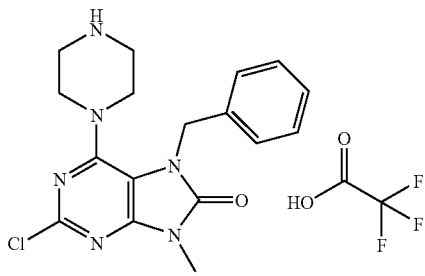

Using benzyl bromide (15 μL) instead of the 1-bromo-2-pentyne in Example 18e), the title compound (2.91 mg) was obtained by treatment similar to that of Example 18e).

MS m/e (ESI) 359(M+H)⁺

EXAMPLE 22

2-Chloro-7,9-dimethyl-6-(piperazin-1-yl)-7,9-dihydropurin-8-one trifluoroacetic acid salt

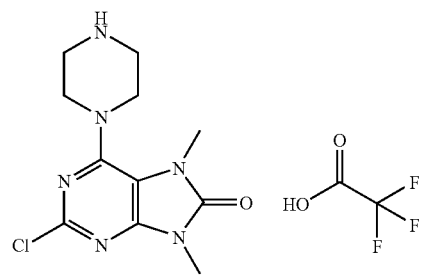

4-(2-Chloro-9-methyl-8-oxo-8,9-dihydro-7H-purin-6-yl)piperazine-1-carboxylic acid t-butyl ester (compound 18d) (10 mg) was dissolved in N,N-dimethylformamide (0.3 mL), and then iodomethane (25 μL) and anhydrous potassium carbonate (15 mg) were added to this solution. After stirring the reaction solution at room temperature for 12 hours, saturated aqueous ammonium chloride solution was added to the reaction solution. This was extracted with ethyl acetate, and the obtained organic layer was concentrated. The residue was dissolved in trifluoroacetic acid. This reaction solution was stirred at room temperature for five minutes, and then concentrated. The residue was purified by reverse phase high performance liquid chromatography to give the title compound (10.01 mg).

¹H-NMR (CD₃OD)

δ 3.44 (s, 3H), 3.45 (m, 4H), 3.59 (s, 3H), 3.64 (m, 4H)

MS m/e (ESI) 283(M+H)⁺

EXAMPLE 23

7,9-Dimethyl-8-oxo-6-(piperazin-1-yl)-8,9-dihydro-7H-purin-2-carbonitrile trifluoroacetic acid salt

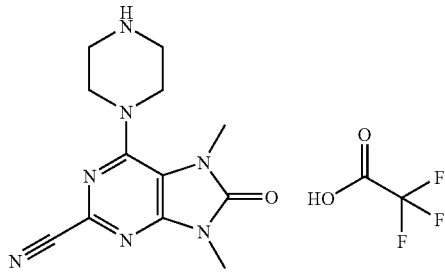

4-(2-Chloro-9-methyl-8-oxo-8,9-dihydro-7H-purin-6-yl)piperazine-1-carboxylic acid t-butyl ester (compound 18d) (20 mg) was dissolved in N,N-dimethylformamide (0.5 mL). Iodomethane (30 μL) and anhydrous potassium carbonate (15 mg) were then added to this solution. After stirring the reaction solution at room temperature for 12 hours, saturated aqueous ammonium chloride solution was added to the reaction solution. This was then extracted with ethyl acetate, and the obtained organic layer was concentrated. Half of the obtained residue was dissolved in dimethylsulfoxide (0.3 mL), and then sodium cyanide (15 mg) was added to this solution. After stirring the reaction solution at 100° C. for 14 hours, water was added to the reaction solution. This was then extracted with ethyl acetate, and the resulting organic layer was concentrated. The residue was dissolved in trifluoroacetic acid. This reaction solution was stirred at room temperature for five minutes, and then concentrated. The residue was purified by reverse phase high performance liquid chromatography to give the title compound (3.43 mg).

$^1$H-NMR (CD$_3$OD)

δ 3.48 (m, 4H), 3.49 (s, 3H), 3.65 (s, 3H), 3.66 (m, 4H)

MS m/e (ESI) 274(M+H)$^+$

EXAMPLE 24

2-Chloro-9-methyl-6-(piperazin-1-yl)-7,9-dihydro-purin-8-one trifluoroacetic acid salt

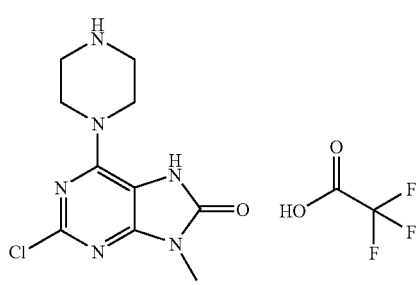

4-(2-Chloro-9-methyl-8-oxo-8,9-dihydro-7H-purin-6-yl)piperazine-1-carboxylic acid t-butyl ester (compound 18d) (8 mg) was dissolved in trifluoroacetic acid. This reaction solution was stirred at room temperature for five minutes, and then concentrated. The residue was purified by reverse phase high performance liquid chromatography to give the title compound (5.08 mg).

MS m/e (ESI) 269(M+H)$^+$

EXAMPLE 25

Piperidin-3-yl carbamic acid t-butyl ester

25a 3-t-Butoxycarbonylaminopiperidin-1-carboxylic acid benzyl ester

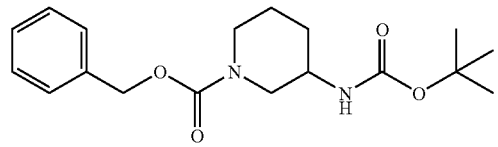

Benzyl chloroformate (30% solution in toluene) (88 g) was added dropwise over 30 minutes an ice-cooled a mixture of piperidin-3-carboxylic acid ethyl ester (24.3 g), triethylamine (26 mL), and ethyl acetate (300 mL). The reaction solution was filtered to remove insoluble substances, and the filtrate was filtered through a small amount of silica gel, and then concentrated.

Ethanol (200 mL) and 5M aqueous sodium hydroxide solution (40 mL) were added to the residue, and this was stirred at room temperature overnight. The reaction solution was concentrated, and water (200 mL) was added to this residue, which was then extracted with t-butyl methyl ether. 5M aqueous hydrochloric acid was added to the aqueous layer, which was then extracted with ethyl acetate. The organic layer was washed with water and saturated brine, then dried over anhydrous magnesium sulfate, and concentrated to give an oily residue (30.9 g).

A mixture of this residue (30 g), diphenylphosphoryl azide (24.5 mL), triethylamine (15.9 mL), and t-butanol (250 mL) was stirred at room temperature for 1.5 hours, and then in an oil bath at 100° C. for 20 hours. The reaction solution was concentrated, the residue was extracted using ethyl acetate and water, and the organic layer was washed with dilute aqueous sodium bicarbonate solution and then with saturated brine. It was then dried over anhydrous magnesium sulfate, and concentrated. The residue was purified by performing silica gel column chromatography using 10% to 20% ethyl acetate/hexane, and a subsequent recrystallization using ethyl acetate and hexane to give the title compound (21.4 g).

$^1$H-NMR (CDCl$_3$)

δ 1.43 (s, 9H), 1.48-1.92 (m, 4H), 3.20-3.80 (m, 5H), 4.58 (br.s, 1H), 5.13 (s, 2H), 7.26-7.40 (m, 5H)

25b

Piperidin-3-yl-carbamic acid t-butyl ester

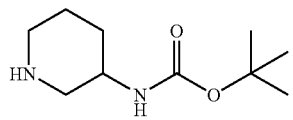

A mixture of 3-t-butoxycarbonylaminopiperidine-1-carboxylic acid benzyl ester (10 g), 10% palladium on carbon (500 mg), and ethanol (100 mL) was stirred under hydrogen atmosphere at room temperature overnight. The catalyst was removed by filtration, and the filtrate was concentrated to dryness to give the title compound (6.0 g).

$^1$H-NMR (CDCl$_3$)

δ 1.44 (s, 9H), 1.47-1.80 (m, 4H), 2.45-2.60 (m, 1H), 2.60-2.75 (m, 1H), 2.75-2.90 (m, 1H), 3.05 (dd, J=3 Hz, 12 Hz, 1H), 3.57 (br.s, 1H), 4.83 (br.s, 1H)

EXAMPLE 26

N-methyl-N-(piperidin-3-yl) carbamic acid t-butyl ester

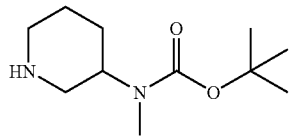

In a water bath at room temperature, sodium hydride (60% in oil) (0.4 g) was added to a mixture of 3-t-butoxycarbonylaminopiperidin-1-carboxylic acid benzyl ester (compound 25a) (3.3 g), methyl iodide (0.75 mL), and N,N-dimethylformamide (20 mL), and this was stirred at room temperature for four hours. The reaction solution was extracted using ethyl acetate and water, the organic layer was washed with water, and then with saturated brine, dried over anhydrous magnesium sulfate, and concentrated. The residue was purified by silica gel column chromatography using 10% to 20% ethyl acetate/hexane to give an oily substance (3.04 g). A mixture of all of the resulting material with ethanol (20 mL) and 10% palladium on carbon was stirred under hydrogen atmosphere at room temperature for five hours. The catalyst was filtered off, and the filtrate was concentrated to give the title compound (1.82 g).

$^1$H-NMR (CDCl$_3$)

δ 1.46 (s, 9H), 1.48-1.64 (m, 2H), 1.72-1.84 (m, 2H), 2.43 (dt, J=3 Hz, 12 Hz, 1H), 2.60 (t, J=12 Hz, 1H), 2.75 (s, 3H), 2.74-3.02 (m, 2H), 3.86 (br.s, 1H)

EXAMPLE 27

6-(3-Amino-piperidin-1-yl)-7-(2-butynyl)-2-chloro-9-methyl-7,9-dihydropurin-8-one trifluoroacetic acid salt 27a

[1-[7-(2-Butynyl)-2-chloro-9-methyl-8-oxo-8,9-dihydro-7H-purin-6-yl]piperazin-3-yl]carbamic acid t-butyl ester

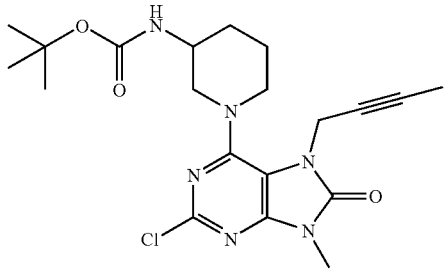

7-(2-Butynyl)-2,6-dichloro-9-methyl-7,9-dihydropurin-8-one (compound 1e) (100 mg) was dissolved in acetonitrile (1.5 mL). Piperidin-3-yl-carbamic acid t-butyl ester (compound 25b) (111 mg) and triethylamine (77 μL) were then added to this solution. After stirring the reaction solution at room temperature for 24 hours, water (6 mL) was added. After stirring this reaction solution at room temperature for 30 minutes, the precipitate was filtered, and the white solid obtained was washed with water and hexane to give the title compound (88 mg).

$^1$H-NMR (DMSO-d6)

δ 1.37 (s, 9H), 1.57-1.91 (m, 4H), 1.76 (t, J=2.3 Hz, 3H), 2.72 (m, 1H), 2.87 (m, 1H), 3.26 (s, 3H), 3.50-3.63 (m, 3H), 4.55 (dd, J=18.0, 2.3 Hz, 1H), 4.64 (dd, J=18.0, 2.3 Hz, 1H), 6.97 (d, J=7.5 Hz, 1H)

27b 6-(3-Amino-piperidin-1-yl)-7-(2-butynyl)-2-chloro-9-methyl-7,9-dihydropurin-8-one trifluoroacetic acid salt

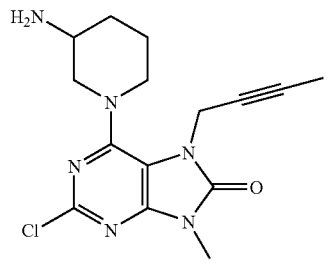 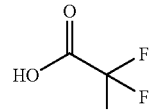

[1-[7-(2-Butynyl)-2-chloro-9-methyl-8-oxo-8,9-dihydro-7H-purin-6-yl]piperazin-3-yl]carbamic acid t-butyl ester (15 mg) was dissolved in trifluoroacetic acid. This reaction solution was stirred at room temperature for five minutes, and then concentrated. The residue was purified by reverse phase high performance liquid chromatography to give the title compound (7.23 mg).

MS m/e (ESI) 335(M+H)$^+$

EXAMPLE 28

7-(2-Butynyl)-2-chloro-9-methyl-6-(3-methylamino-piperidin-1-yl)-7,9-dihydropurin-8-one trifluoroacetic acid salt

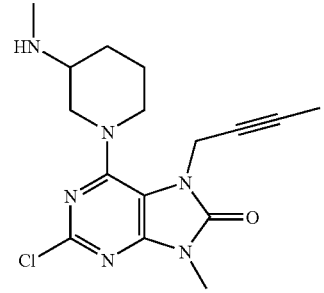 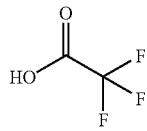

Using methyl(piperidin-3-yl)carbamic acid t-butyl ester (compound 26) instead of the (piperidin-3-yl)carbamic acid t-butyl ester in Example 27a, the title compound (4.16 mg) was obtained by treatment similar to that of Example 27.

MS m/e (ESI) 349(M+H)$^+$

EXAMPLE 29

2-[7-(2-Butynyl)-2-chloro-8-oxo-6-(piperazin-1-yl)-7,8-dihydropurin-9-ylmethyl]benzonitrile trifluoroacetic acid salt

29a 2,2-Dimethylpropionic acid [7-(2-butynyl)-2,6-dichloro-8-oxo-7,8-dihydropurin-9-yl]methyl ester

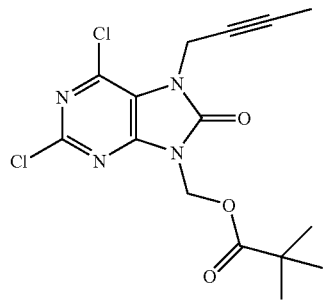

7-(2-Butynyl)-2,6-dichloro-7,9-dihydropurin-8-one (compound 1d) (193 mg) was dissolved in N,N-dimethylformamide (2 mL), and then 2,2-dimethylpropionic acid chloromethyl ester (163 μL) and anhydrous potassium carbonate (156 mg) were added to this solution. After stirring the reaction solution at room temperature for 18 hours, saturated aqueous ammonium chloride solution (5 mL) was added to the reaction solution. This was then extracted with ethyl acetate. The obtained organic layer was washed sequentially with water and then saturated brine, and then dried over anhydrous magnesium sulfate. The organic layer was concentrated under reduced pressure to give the title compound (434 mg).

$^1$H-NMR (CDCl$_3$)

δ 1.20 (s, 9H), 1.81 (t, J=2.4 Hz, 3H), 4.82 (q, J=2.4 Hz, 2H), 5.94 (s, 2H)

29b

4-[7-(2-Butynyl)-2-chloro-9-(2,2-dimethylpropionyloxymethyl)-8-oxo-8,9-dihydro-7H-purin-6-yl]piperazine-1-carboxylic acid t-butyl ester

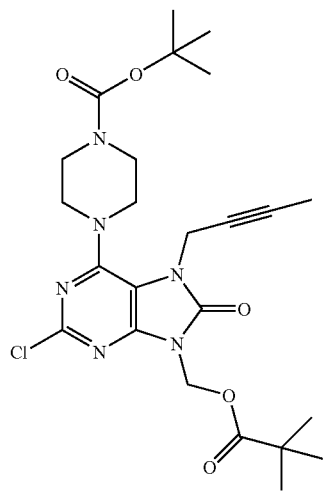

2,2-Dimethylpropionic acid [7-(2-butynyl)-2,6-dichloro-8-oxo-7,8-dihydropurin-9-yl] methyl ester (434 mg) was dissolved in acetonitrile (4 mL). Piperazine-1-carboxylic acid t-butyl ester (325 mg) and triethylamine (243 μL) were then added to this solution. The reaction solution was stirred at room temperature for 22 hours, then 1 N aqueous hydrochloric acid (3 mL) and water (10 mL) were added to the reaction solution. This was then extracted with ethyl acetate. The obtained organic layer was washed sequentially with water and then saturated brine, and then dried over anhydrous magnesium sulfate. The organic layer was concentrated under reduced pressure to give the title compound (660 mg).

$^1$H-NMR (CDCl$_3$)

δ 1.20 (s, 9H), 1.44 (s, 9H), 1.79 (t, J=2.4 Hz, 3H), 3.40 (m, 4H), 3.60 (m, 4H), 4.64 (q, J=2.4 Hz, 2H), 5.88 (s, 2H)

29c

4-[7-(2-Butynyl)-2-chloro-8-oxo-8,9-dihydro-7H-purin-6-yl]piperazine-1-carboxylic acid t-butyl ester

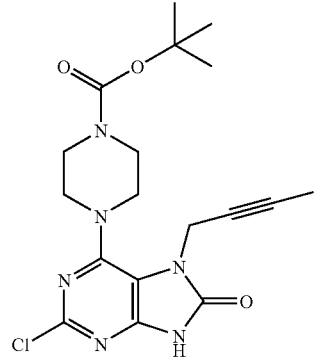

4-[7-(2-Butynyl)-2-chloro-9-(2,2-dimethylpropionyloxymethyl)-8-oxo-8,9-dihydro-7H-purin-6-yl]piperazine-1-carboxylic acid t-butyl ester (665 mg) was dissolved in a mixed solvent of methanol (5 mL) and tetrahydrofuran (3 mL), and then sodium hydride (60-72% in oil) (61 mg) was added to this solution. The reaction solution was stirred at room temperature for three hours. 1 N aqueous hydrochloric acid (3 mL) was then added to the reaction solution, which was extracted using ethyl acetate. The obtained organic layer was washed sequentially with water and saturated brine, and then dried over anhydrous magnesium sulfate. The organic layer was concentrated under reduced pressure, and the residue was purified by silica gel column chromatography (ethyl acetate:hexane=1:3) to give the title compound (294 mg).

$^1$H-NMR (CDCl$_3$)

δ 1.50 (s, 9H), 1.81 (t, J=2.4 Hz, 3H), 3.38-3.42 (m, 4H), 3.59-3.62 (m, 4H), 4.63 (q, J=2.4 Hz, 2H)

29d

2-[7-(2-Butynyl)-2-chloro-8-oxo-6-(piperazin-1-yl)-7,8-dihydropurin-9-ylmethyl]benzonitrile trifluoroacetic acid salt

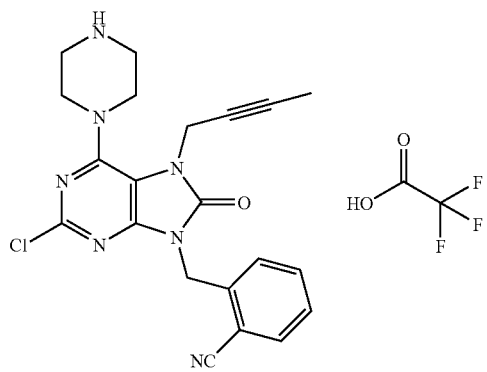

4-[7-(2-Butynyl)-2-chloro-8-oxo-8,9-dihydro-7H-purin-6-yl]piperazine-1-carboxylic acid t-butyl ester (8 mg) was dissolved in N,N-dimethylformamide (0.5 mL), and then 2-(bromomethyl)benzonitrile (8 mg) and anhydrous potassium carbonate (5 mg) were added to this solution. The reaction solution was stirred at room temperature for 12 hours, then saturated aqueous ammonium chloride was added to the reaction solution, and this was extracted with ethyl acetate. The organic layer was concentrated, and the residue was dissolved in trifluoroacetic acid. This reaction solution was stirred at room temperature for five minutes, and then concentrated. The residue was purified by reverse phase high performance liquid chromatography to give the title compound (4.36 mg).

MS m/e (ESI) 422(M+H)$^+$

EXAMPLE 30

7-(2-Butynyl)-2-chloro-6-(piperazin-1-yl)-9-propyl-7,9-dihydropurin-8-one trifluoroacetic acid salt

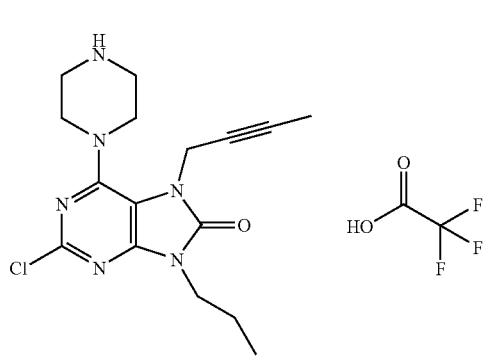

Using 3-iodopropane (20 μL) instead of the 2-(bromomethyl)benzonitrile in Example 29d, the title compound (3.71 mg) was obtained by treatment similar to that of Example 29d.

MS m/e (ESI) 349(M+H)$^+$

EXAMPLE 31

[7-(2-Butynyl)-2-chloro-8-oxo-6-(piperazin-1-yl)-7,8-dihydropurin-9-yl]acetic acid trifluoroacetic acid salt

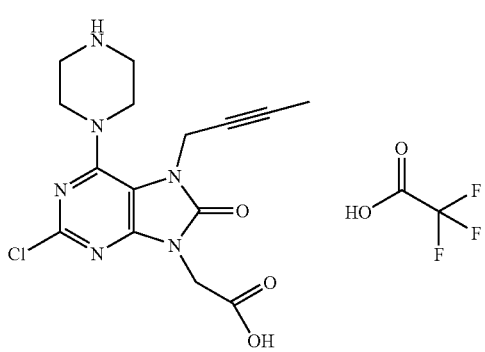

Using bromoacetic acid t-butyl ester (20 μL) instead of the 2-(bromomethyl)benzonitrile in Example 29d, the title compound (3.55 mg) was obtained by treatment similar to that of Example 29d.

MS m/e (ESI) 365(M+H)$^+$

EXAMPLE 32

[7-(2-Butynyl)-2-chloro-8-oxo-6-(piperazin-1-yl)-7,8-dihydropurin-9-yl]acetonitrile trifluoroacetic acid salt

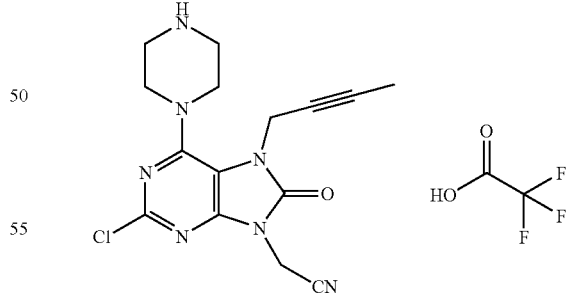

Using bromoacetonitrile (20 μL) instead of the 2-(bromomethyl)benzonitrile in Example 29d, the title compound (4.74 mg) was obtained by treatment similar to that of Example 29d.

MS m/e (ESI) 346(M+H)$^+$

EXAMPLE 33

2-[7-(2-Butynyl)-2-chloro-8-oxo-6-(piperazin-1-yl)-7,8-dihydropurin-9-yl]acetamide trifluoroacetic acid salt

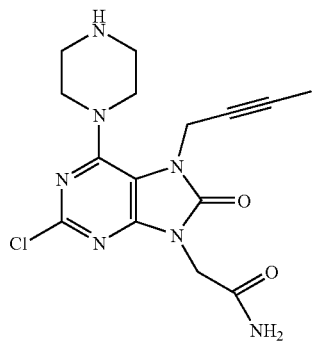 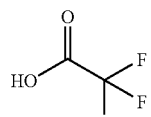

Using 2-bromoacetamide (5 mg) instead of the 2-(bromomethyl)benzonitrile in Example 29d, the title compound (4.71 mg) was obtained by treatment similar to that of Example 29d.

MS m/e (ESI) 364(M+H)+

EXAMPLE 34

7-(2-Butynyl)-2-chloro-9-(2-phenylethyl)-6-(piperazin-1-yl)-7,9-dihydropurin-8-one trifluoroacetic acid salt

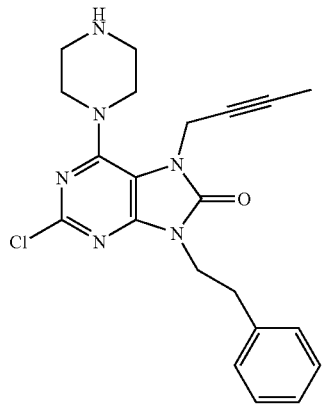 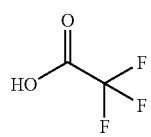

Using (2-bromoethyl)benzene (20 μL) instead of the 2-(bromomethyl)benzonitrile in Example 29d, the title compound (5.12 mg) was obtained by treatment similar to that of Example 29d.

MS m/e (ESI) 411(M+H)+

EXAMPLE 35

9-[2-(4-Bromophenyl)-ethyl]-7-(2-butynyl)-2-chloro-6-(piperazin-1-yl)-7,9-dihydropurin-8-one trifluoroacetic acid salt

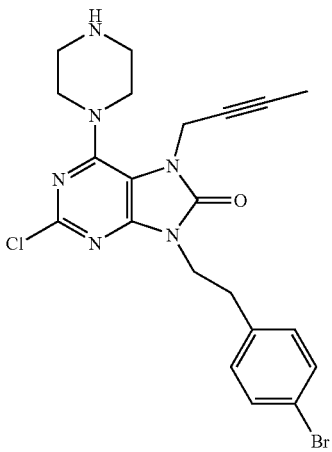 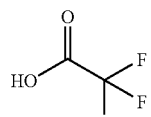

Using methanesulfonic acid 2-(4-bromophenyl)ethylester (10 mg) instead of the 2-(bromomethyl)benzonitrile in Example 29d, the title compound (1.56 mg) was obtained by treatment similar to that of Example 29d.

MS m/e (ESI) 491(M+H)+

EXAMPLE 36

9-Benzyl-7-(2-butynyl)-2-chloro-6-(piperazin-1-yl)-7,9-dihydropurin-8-one trifluoroacetic acid salt

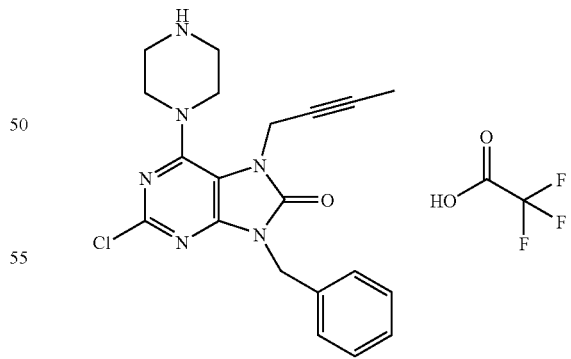

Using benzyl bromide (20 μL) instead of the 2-(bromomethyl)benzonitrile in Example 29d, the title compound (1.23 mg) was obtained by treatment similar to that of Example 29d.

MS m/e (ESI) 397(M+H)+

EXAMPLE 37

4-[7-(2-Butynyl)-2-chloro-8-oxo-6-(piperazin-1-yl)-7,8-dihydropurin-9-yl]butyronitrile trifluoroacetic acid

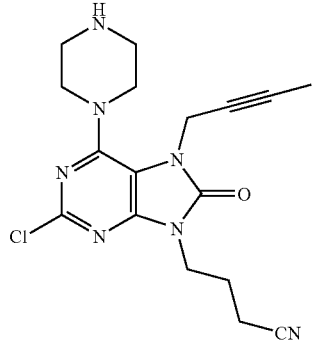 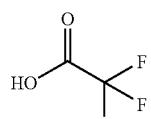

Using 4-chlorobutyronitrile (20 µL) instead of the 2-(bromomethyl)benzonitrile in Example 29d, the title compound (5.80 mg) was obtained by treatment similar to that of Example 29d.

MS m/e (ESI) 374(M+H)+

EXAMPLE 38

7-(2-Butynyl)-2-chloro-9-cyclopropylmethyl-6-(piperazin-1-yl)-7,9-dihydropurin-8-one trifluoroacetic acid salt

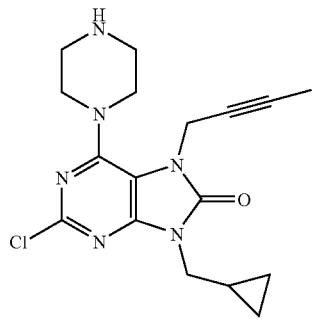 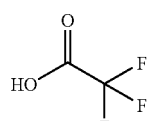

Using bromomethylcyclopropane (20 µL) instead of the 2-(bromomethyl)benzonitrile in Example 29d, the title compound (0.83 mg) was obtained by treatment similar to that of Example 29d.

MS m/e (ESI) 361(M+H)+

EXAMPLE 39

2-[7-(2-Butynyl)-2-chloro-8-oxo-6-(piperazin-1-yl)-7,8-dihydropurin-9-ylmethyl]benzamide trifluoroacetic acid salt

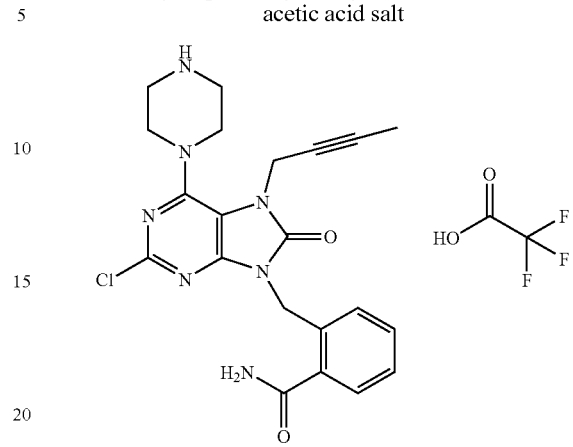

4-[7-(2-Butynyl)-2-chloro-8-oxo-8,9-dihydro-7H-purin-6-yl]piperazine-1-carboxylic acid t-butyl ester (compound 29c) (8 mg) was dissolved in N,N-dimethylformamide (0.5 mL), and then 2-bromomethylbenzonitrile (20 µL) and anhydrous potassium carbonate (8 mg) were added to this solution. The reaction solution was stirred at room temperature for 48 hours. Saturated aqueous ammonium chloride solution was then added to the reaction solution, and this was extracted with ethyl acetate. The obtained organic layer was concentrated. The residue was dissolved in methanol (0.25 mL) and tetrahydrofuran (0.25 mL), and then aqueous ammonia (0.5 mL) and 30% aqueous hydrogen peroxide (0.3 mL) were added to this solution. The reaction solution was stirred at room temperature for 12 hours, and the reaction solution was then concentrated. The residue was dissolved in trifluoroacetic acid, and this reaction solution was stirred at room temperature for five minutes, and then concentrated. The residue was purified by reverse phase high performance liquid chromatography to give the title compound (1.15 mg).

MS m/e (ESI) 440(M+H)+

EXAMPLE 40

[7-(2-Butynyl)-2-chloro-8-oxo-6-(piperazin-1-yl)-7,8-dihydropurin-9-yl]acetic acid methyl ester trifluoroacetic acid salt

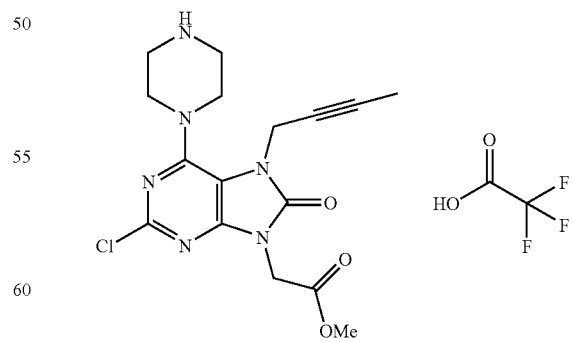

4-[7-(2-Butynyl)-2-chloro-8-oxo-8,9-dihydro-7H-purin-6-yl]piperazine-1-carboxylic acid t-butyl ester (compound 29c) (8 mg) was dissolved in N,N-dimethylformamide (0.5 mL), and then bromoacetonitrile (20 µL) and anhydrous potassium carbonate (8 mg) were added to this solution. The reaction solution was stirred at room temperature for 18 hours. Saturated aqueous ammonium chloride solution was then added to the reaction solution, and this was extracted with ethyl acetate. The obtained organic layer was concentrated, the residue was dissolved in methanol (0.5 mL), and then cesium carbonate (10 mg) was added to this solution. After stirring the reaction solution at 70° C. for 18 hours, the reaction solution was concentrated. The residue was dissolved in trifluoroacetic acid, and this reaction solution was stirred at room temperature for five minutes, and then concentrated. The residue was purified by reverse phase high performance liquid chromatography to give the title compound (2.85 mg).

MS m/e (ESI) 379(M+H)$^+$

EXAMPLE 41

7-(2-Butynyl)-2-chloro-9-phenyl-6-(piperazin-1-yl)-7,9-dihydropurin-8-one trifluoroacetic acid salt

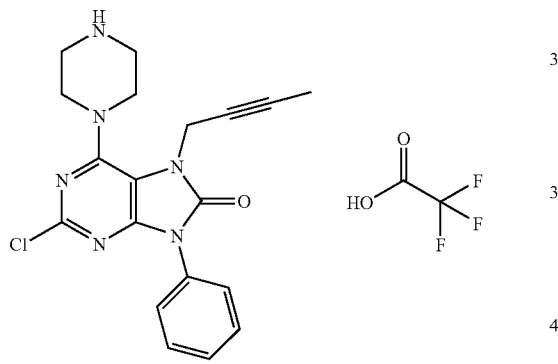

4-[7-(2-Butynyl)-2-chloro-8-oxo-8,9-dihydro-7H-purin-6-yl]piperazine-1-carboxylic acid t-butyl ester (compound 29c) (8 mg) was dissolved in N,N-dimethylformamide (0.3 mL). Phenylboronic acid (10 mg), copper(II) acetate (5 mg), and pyridine (100 μL) were then added to this solution. The reaction solution was stirred at 50° C. for 18 hours, then saturated aqueous ammonium chloride solution was added to the reaction solution, and this was extracted with ethyl acetate. The obtained organic layer was concentrated, and the residue was dissolved in trifluoroacetic acid. This reaction solution was stirred at room temperature for five minutes, and then concentrated. The residue was purified by reverse phase high performance liquid chromatography to give the title compound (3.43 mg).

$^1$H-NMR (CDCl$_3$)

δ 1.87 (t, J=2.0 Hz, 3H), 3.52 (m, 4H), 3.70 (m, 4H), 4.83 (q, J=2.0 Hz, 2H), 7.53-7.65 (m, 5H)

MS m/e (ESI) 383(M+H)$^+$

EXAMPLE 42

4-[7-(2-Butynyl)-2-chloro-8-oxo-6-(piperazin-1-yl)-7,8-dihydropurin-9-yl]benzonitrile trifluoroacetic acid salt

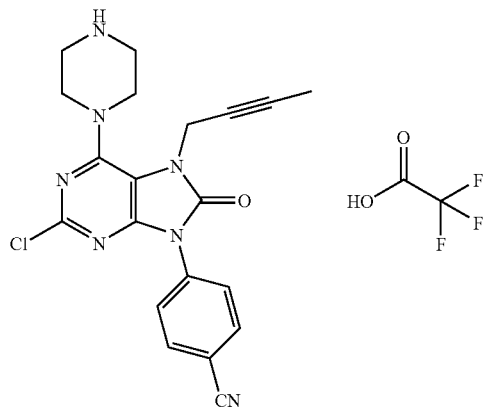

Using 4-cyanophenylboronic acid (10 mg) instead of the phenylboronic acid in Example 41, the title compound (1.57 mg) was obtained by treatment similar to that of Example 41.

MS m/e (ESI) 408(M+H)$^+$

EXAMPLE 43

7-(2-Butynyl)-2-chloro-9-(4-methoxyphenyl)-6-(piperazin-1-yl)-7,9-dihydropurin-8-one trifluoroacetic acid salt

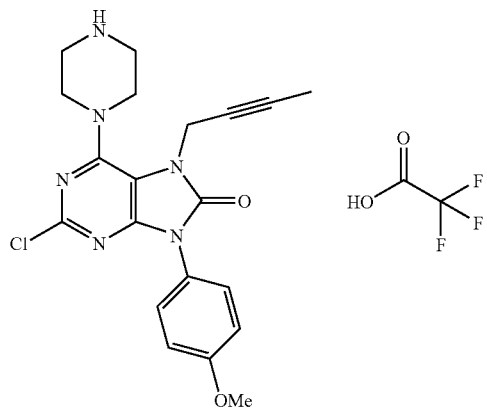

Using 4-methoxyphenylboronic acid (10 mg) instead of the phenylboronic acid in Example 41, the title compound (3.00 mg) was obtained by treatment similar to that of Example 41.

MS m/e (ESI) 413(M+H)$^+$

EXAMPLE 44

7-(2-Butynyl)-2-chloro-9-(furan-3-yl)-6-(piperazin-1-yl)-7,9-dihydropurin-8-one trifluoroacetic acid salt

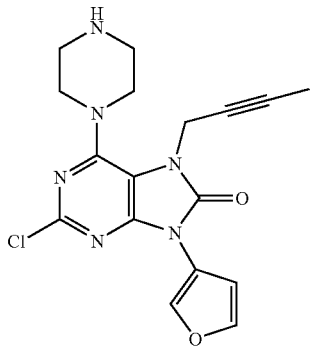 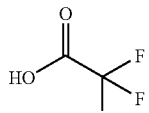

Using 3-furanboronic acid (10 mg) instead of the phenylboronic acid in Example 41, the title compound (1.23 mg) was obtained by treatment similar to that of Example 41.

MS m/e (ESI) 373(M+H)$^+$

EXAMPLE 45

7-(2-Butynyl)-2-chloro-6-(piperazin-1-yl)-9-(thiophen-3-yl)-7,9-dihydropurin-8-one trifluoroacetic acid salt

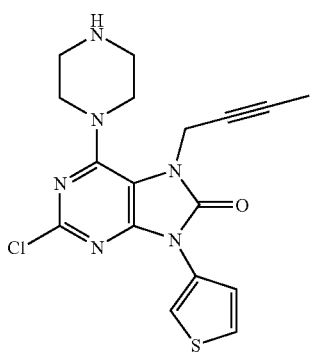 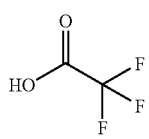

Using 3-thiopheneboronic acid (10 mg) instead of the phenylboronic acid in Example 41, the title compound (3.57 mg) was obtained by treatment similar to that of Example 41

MS m/e (ESI) 389(M+H)$^+$

EXAMPLE 46

7-(2-Butynyl)-2-chloro-6-(piperazin-1-yl)-9-(pyridin-3-yl)-7,9-dihydropurin-8-one trifluoroacetic acid salt

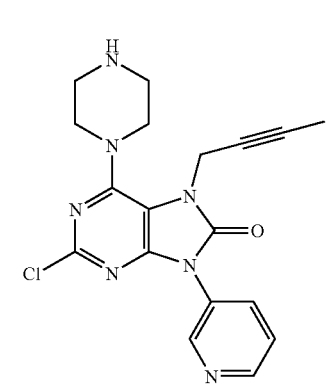 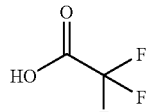

Using pyridine-3-boronic acid (10 mg) instead of the phenylboronic acid in Example 41, the title compound (3.44 mg) was obtained by treatment similar to that of Example 41

MS m/e (ESI) 384(M+H)$^+$

EXAMPLE 47

9-Allyl-7-(2-butynyl)-2-methoxy-6-(piperazin-1-yl)-7,9-dihydropurin-8-one trifluoroacetic acid salt

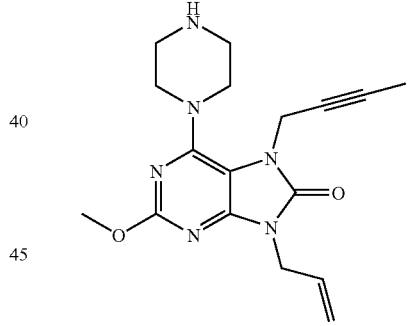 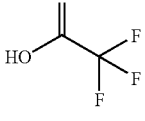

4-[7-(2-Butynyl)-2-chloro-8-oxo-8,9-dihydro-7H-purin-6-yl]piperazine-1'-carboxylic acid t-butyl ester (compound 29c) (8 mg) was dissolved in N,N-dimethylformamide (0.3 mL). Allyl bromide (20 µL) and anhydrous potassium carbonate (8 mg) were then added to this solution. The reaction solution was stirred at room temperature for 18 hours, then saturated aqueous ammonium chloride solution was added to the reaction solution, and this was extracted with ethyl acetate. The obtained organic layer was concentrated, the residue was dissolved in methanol (0.5 mL), and then cesium carbonate (10 mg) was added to this solution. After stirring the reaction solution at 70° C. for 18 hours, the reaction solution was concentrated. The residue was dissolved in trifluoroacetic acid, and this reaction solution was stirred at room temperature for five minutes, and then concentrated. The residue was purified by reverse phase high performance liquid chromatography to give the title compound (4.72 mg).

$^1$H-NMR (CD$_3$OD)

δ 1.83 (t, J=2.4 Hz, 3H), 3.47 (m, 4H), 3.67 (m, 4H), 4.00 (s, 3H), 4.52 (dt, J=5.6, 1.6 Hz, 2H), 4.71 (q, J=2.4 Hz, 2H), 5.20 (dm, J=16.8 Hz, 1H), 5.24 (dm, J=9.6 Hz, 1H), 6.00 (ddt, J=16.8, 9.6, 5.6 Hz, 1H)

MS m/e (ESI) 343(M+H)$^+$

EXAMPLE 48

7,9-Di-(2-butynyl)-2-methoxy-6-(piperazin-1-yl)-7,9-dihydropurin-8-one trifluoroacetic acid salt

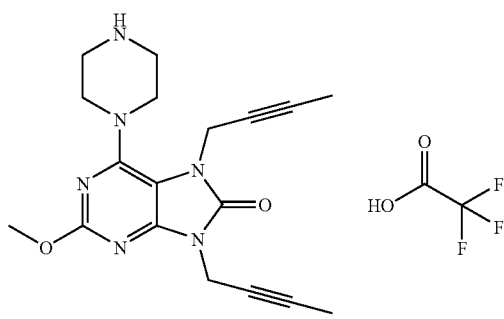

Using 1-bromo-2-butyne (20 µL) instead of the allyl bromide in Example 47, the title compound (1.99 mg) was obtained by treatment similar to that of Example 47.

MS m/e (ESI) 355(M+H)$^+$

EXAMPLE 49

4-[7-(2-Butynyl)-2-methoxy-8-oxo-6-(piperazin-1-yl)-7,8-dihydropurin-9-ylmethyl]benzonitrile trifluoroacetic acid salt

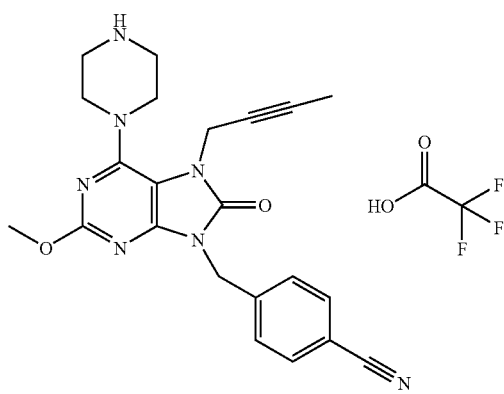

Using 4-cyano-benzylbromide (15 mg) instead of the allyl bromide in Example 47, the title compound (5.36 mg) was obtained by treatment similar to that of Example 47.

MS m/e (ESI) 418(M+H)$^+$

EXAMPLE 50

2-[7-(2-Butynyl)-2-methoxy-8-oxo-6-(piperazin-1-yl)-7,8-dihydropurin-9-ylmethyl]benzonitrile trifluoroacetic acid salt

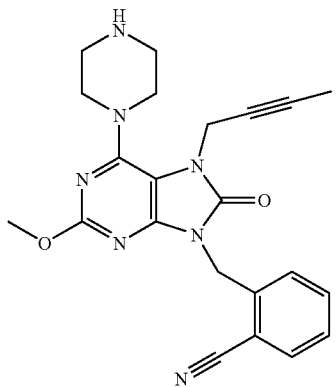 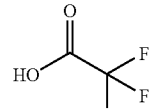

Using 2-cyano-benzylbromide (15 mg) instead of the allyl bromide in Example 47, the title compound (5.51 mg) was obtained by treatment similar to that of Example 47.

MS m/e (ESI) 418(M+H)$^+$ $^1$H-NMR (CD$_3$OD)

δ 1.83 (t, J=2.4 Hz, 3H), 3.47 (m, 4H), 3.68 (m, 4H), 3.97 (s, 3H), 4.72 (q, J=2.4 Hz, 2H), 5.32 (s, 2H), 7.46-7.81 (m, 4H)

EXAMPLE 51

7-(2-Butynyl)-9-cyclopropylmethyl-2-methoxy-6-(piperazin-1-yl)-7,9-dihydropurin-8-one trifluoroacetic acid salt

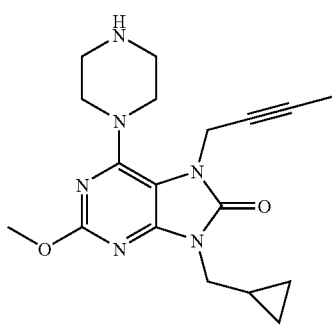 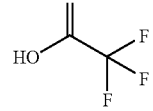

Using bromomethylcyclopropane (25 µL) instead of the allyl bromide in Example 47, the title compound (2.46 mg) was obtained by treatment similar to that of Example 47.

MS m/e (ESI) 357(M+H)$^+$

EXAMPLE 52

7-(2-Butynyl)-2-methoxy-6-(piperazin-1-yl)-9-propyl-7,9-dihydropurin-8-one trifluoroacetic acid salt

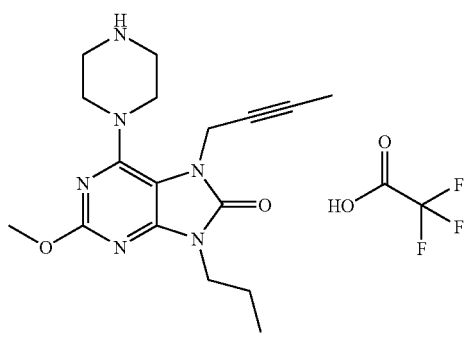

Using 1-iodopropane (25 µL) instead of the allyl bromide in Example 47, the title compound (3.90 mg) was obtained by treatment similar to that of Example 47.

MS m/e (ESI) 345(M+H)$^+$

EXAMPLE 53

7-(2-Butynyl)-2-methoxy-6-(piperazin-1-yl)-7,9-dihydropurin-8-one trifluoroacetic acid salt

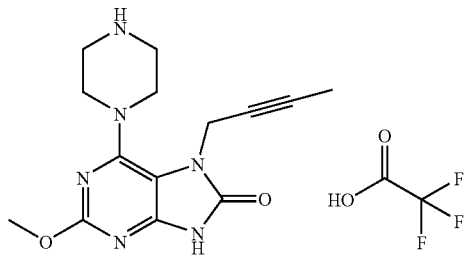

Using propargyl bromide (25 µL) instead of the allyl bromide in Example 47, the title compound (2.63 mg) was obtained by treatment similar to that of Example 47.

MS m/e (ESI) 303(M+H)$^+$

EXAMPLE 54

7-(2-Butynyl)-2-methoxy-9-phenyl-6-(piperazin-1-yl)-7,9-dihydropurin-8-one trifluoroacetic acid salt

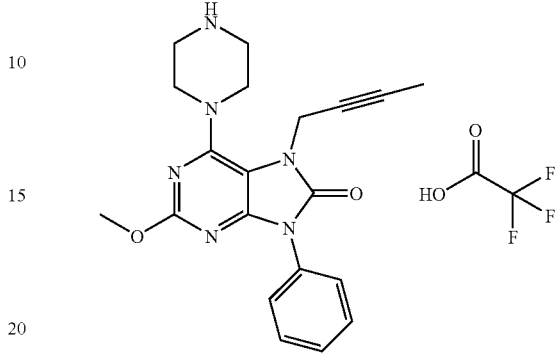

4-[7-(2-Butynyl)-2-chloro-8-oxo-8,9-dihydro-7H-purin-6-yl]piperazine-1-carboxylic acid t-butyl ester (compound 29c) (10 mg) was dissolved in N,N-dimethylformamide (0.3 mL). Phenylboronic acid (10 mg), copper(II) acetate (5 mg), and pyridine (100 µL) were then added to this solution. The reaction solution was stirred at 40° C. for 18 hours, then saturated aqueous ammonium chloride solution was added to the reaction solution, and this was extracted with ethyl acetate. The obtained organic layer was concentrated, the residue was dissolved in methanol (0.5 mL), and then cesium carbonate (10 mg) was added to the solution. The reaction solution was stirred at 70° C. for 18 hours, and then concentrated. The residue was dissolved in trifluoroacetic acid. This was then stirred at room temperature for five minutes, and concentrated. The residue was purified by reverse phase high performance liquid chromatography to give the title compound (2.88 mg).

MS m/e (ESI) 379(M+H)$^+$

EXAMPLE 55

7-(2-Butynyl)-2-methoxy-6-(piperazin-1-yl)-9-(pyridin-3-yl)-7,9-dihydropurin-8-one trifluoroacetic acid salt

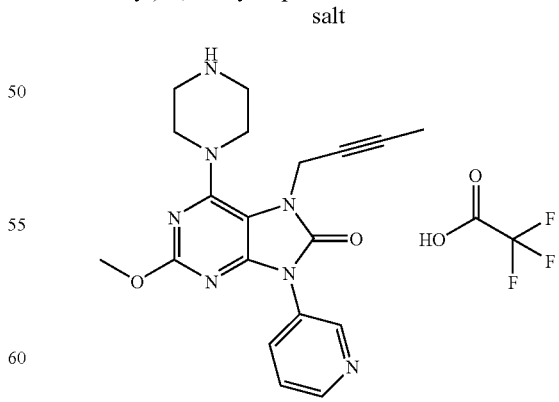

Using pyridine-3-boronic acid (10 mg) instead of the phenylboronic acid in Example 54, the title compound (2.29 mg) was obtained by treatment similar to that of Example 54.

MS m/e (ESI) 380(M+H)$^+$

EXAMPLE 56

7-(2-Butynyl)-9-(furan-3-yl)-2-methoxy-6-(piperazin-1-yl)-7,9-dihydropurin-8-one trifluoroacetic acid salt

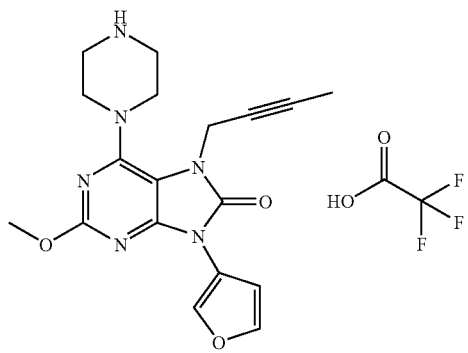

Using furan-3-boronic acid (10 mg) instead of the phenylboronic acid in Example 54, the title compound (2.19 mg) was obtained by treatment similar to that of Example 54.
MS m/e (ESI) 369(M+H)+

EXAMPLE 57

7-(2-Butynyl)-9-(thiophen-3-yl)-2-methoxy-6-(piperazin-1-yl)-7,9-dihydropurin-8-one trifluoroacetic acid salt

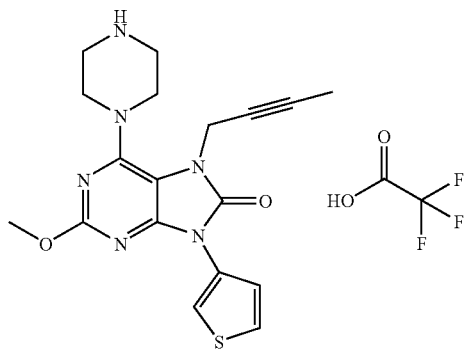

Using thiophene-3-boronic acid (10 mg) instead of the phenylboronic acid in Example 54, the title compound (3.18 mg) was obtained by treatment similar to that of Example 54.
MS m/e (ESI) 385(M+H)+

EXAMPLE 58

7-(2-Butynyl)-2-methoxy-6-(piperazin-1-yl)-9-(4-vinyl-phenyl)-7,9-dihydropurin-8-one trifluoroacetic acid salt

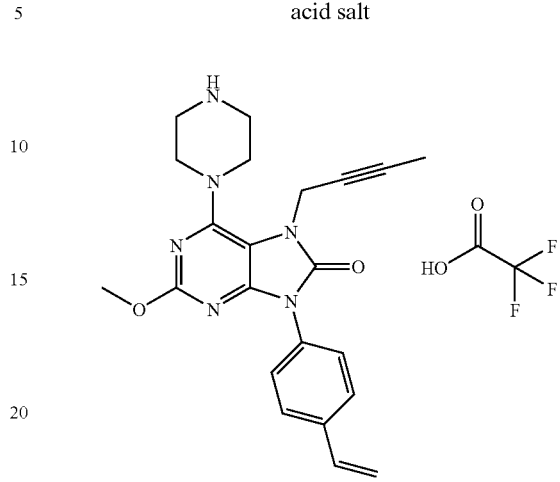

Using 4-vinylphenylboronic acid (10 mg) instead of the phenylboronic acid in Example 54, the title compound (3.12 mg) was obtained by treatment similar to that of Example 54.
MS m/e (ESI) 405(M+H)+

EXAMPLE 59

9-Allyl-7-(2-butynyl)-2-ethoxy-6-(piperazin-1-yl)-7,9-dihydropurin-8-one trifluoroacetic acid salt

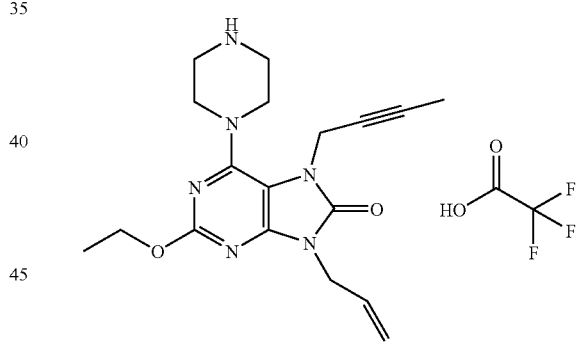

4-[7-(2-Butynyl)-2-chloro-8-oxo-8,9-dihydro-7H-purin-6-yl]piperazine-1-carboxylic acid t-butyl ester (compound 29c) (8 mg) was dissolved in N,N-dimethylformamide (0.5 mL). Allyl bromide (20 μL) and anhydrous potassium carbonate (8 mg) were then added to this solution. The reaction solution was stirred at room temperature for 12 hours, then saturated aqueous ammonium chloride solution was added. This reaction solution was then extracted with ethyl acetate. The obtained organic layer was concentrated, the residue was dissolved in ethanol (0.5 mL), and then cesium carbonate (10 mg) was added to this solution. The reaction solution was stirred at 80° C. for 14 hours, and then concentrated. The residue was dissolved in trifluoroacetic acid. This reaction solution was stirred at room temperature for five minutes, and then concentrated. The residue was purified by reverse phase high performance liquid chromatography to give the title compound (4.21 mg).
MS m/e (ESI) 356(M+H)+

EXAMPLE 60

2-[9-Allyl-7-(2-butynyl)-8-oxo-6-(piperazin-1-yl)-8, 9-dihydro-7H-purin-2-yloxy]benzamide trifluoroacetic acid salt

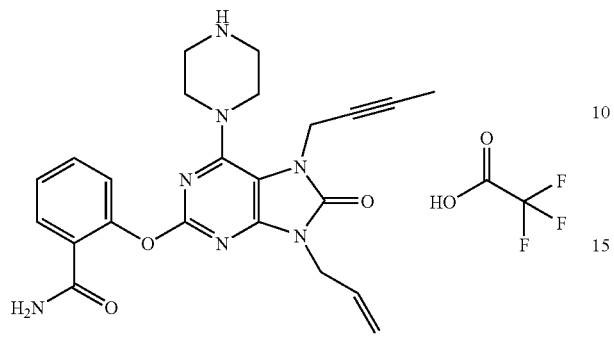

4-[7-(2-Butynyl)-2-chloro-8-oxo-8,9-dihydro-7H-purin-6-yl]piperazine-1-carboxylic acid t-butyl ester (compound 29c) (8 mg) was dissolved in N,N-dimethylformamide (0.5 mL). Allyl bromide (20 μL) and anhydrous potassium carbonate (8 mg) were then added to this solution. The reaction solution was stirred at room temperature for 12 hours, then saturated aqueous ammonium chloride solution was added. This reaction solution was then extracted with ethyl acetate. The obtained organic layer was concentrated, and the residue was dissolved in 1-methyl-2-pyrrolidone (0.5 mL). Salicylamide (10 mg) and cesium carbonate (10 mg) were added to this solution. The reaction solution was stirred at 80° C. for 14 hours and then concentrated. The residue was dissolved in trifluoroacetic acid. This reaction solution was stirred at room temperature for five minutes, and then concentrated. The residue was purified by reverse phase high performance liquid chromatography to give the title compound (1.69 mg).

MS m/e (ESI) 448(M+H)$^+$

EXAMPLE 61

7-(2-Butynyl)-6-(piperazin-1-yl)-9-(pyridin-3-yl)-7, 9-dihydropurin-8-one trifluoroacetic acid salt

61a 4-(6-Chloro-5-nitro-pyrimidin-4-yl)piperazine-1-carboxylic acid t-butyl ester

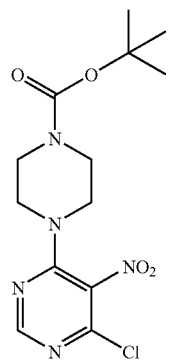

4,6-Dichloro-5-nitropyrimidine [CAS No. 4316-93-2] (2.0 g) was dissolved in acetonitrile (30 mL), and then piperazine-1-carboxylic acid t-butyl ester (1.92 g) and triethylamine (2.1 mL) were added to this solution. The reaction solution was stirred at room temperature for 14 hours, and then water (30 mL) was added. The reaction solution was stirred at room temperature for 30 minutes, and then the precipitate was collected by filtration. The obtained solid was washed with water and hexane to give the title compound (2.94 g).

$^1$H-NMR (CDCl$_3$)
δ 1.48 (s, 9H) 3.54-3.61 (m, 8H) 8.39 (s, 1H)

61b

4-[6-(2-Cyano-ethylamino)-5-nitro-pyrimidin-4-yl]piperazine-1-carboxylic acid t-butyl ester

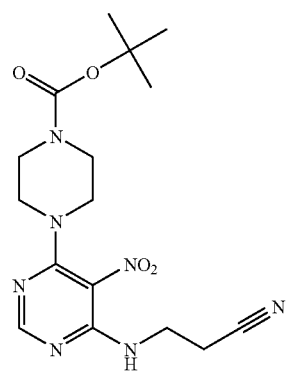

4-(6-Chloro-5-nitro-pyrimidin-4-yl)piperazine-1-carboxylic acid t-butyl ester (3.0 g) was dissolved in acetonitrile (30 mL), and then 3-aminopropionitrile (0.71 mL) and triethylamine (1.58 mL) were added to this solution. After stirring the reaction solution at room temperature for 14 hours, water (60 mL) was added. The reaction solution was stirred at room temperature for 30 minutes, and then the precipitate was collected by filtration. The obtained yellow solid was washed with water and hexane to give the title compound (1.97 g).

61c

4-[9-(2-Cyano-ethyl)-8-oxo-8,9-dihydro-7H-purin-6-yl]piperazine-1-carboxylic acid t-butyl ester

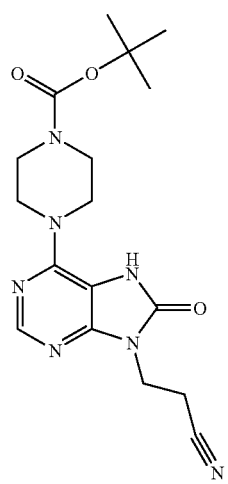

4-[6-(2-Cyano-ethylamino)-5-nitro-pyrimidin-4-yl]piperazine-1-carboxylic acid t-butyl ester (1.0 g) was dissolved in tetrahydrofuran (12 mL), and then 10% palladium on carbon powder (wet type) (200 mg) was added to this solution. The reaction solution was stirred under a hydrogen atmosphere at room temperature for 20 hours. Insoluble substances were then removed by filtration, and the obtained filtrate was concentrated under reduced pressure. The obtained residue was dissolved in acetonitrile (30 mL), and then N,N'-disuccinimidyl carbonate (1.13 g) was added to this solution. The reaction solution was stirred at room temperature for five hours, then 40 mL of water was added. This reaction solution was then concentrated under reduced pressure to 40 mL. The precipitate was collected by filtration. The obtained solid was washed with water and hexane to give the title compound (623 mg). A portion of the obtained compound was purified by silica gel column chromatography for use in NMR analysis.

¹H-NMR (CDCl₃)

δ 1.51 (s, 9H), 2.97 (t, J=6.8 Hz, 2H), 3.61 (m, 4H), 3.73 (m, 4H), 4.25 (t, J=6.8 Hz, 2H), 8.27 (s, 1H), 10.90 (br.s, 1H)

61d

4-[7-(2-Butynyl)-9-(2-cyano-ethyl)-8-oxo-8,9-dihydro-7H-purin-6-yl]piperazine-1-carboxylic acid t-butyl ester

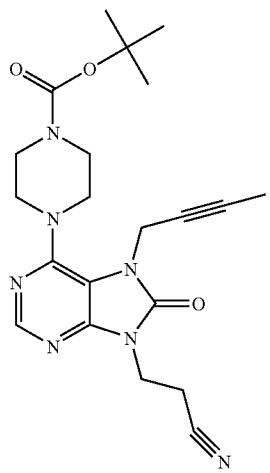

4-[9-(2-Cyano-ethyl)-8-oxo-8,9-dihydro-7H-purin-6-yl]piperazine-1-carboxylic acid t-butyl ester (623 mg) was dissolved in N,N-dimethylformamide (10 mL). Potassium carbonate (300 mg) and 1-bromo-2-butyne (0.18 mL) were then added to this solution. The reaction solution was stirred at room temperature for 19 hours, then water (20 mL) and 1 N hydrochloric acid (5 mL) were added. This was then twice extracted with ethyl acetate, and the obtained organic layer was washed with water and saturated brine. The resulting organic layer was dried over magnesium sulfate, and then concentrated under reduced pressure. The residue was purified by silica gel column chromatography to give the title compound (484 mg).

¹H-NMR (CDCl₃)

δ 1.51 (s, 9H), 1.81 (t, J=2.4 Hz, 3H), 2.96 (t, J=7.2 Hz, 2H), 3.36 (m, 4H), 3.62 (m, 4H), 4.27 (t, J=7.2 Hz, 2H), 4.70 (q, J=2.4 Hz, 2H), 8.37 (s, 1H)

61e

4-[7-(2-Butynyl)-8-oxo-8,9-dihydro-7H-purin-6-yl]piperazine-1-carboxylic acid t-butyl ester

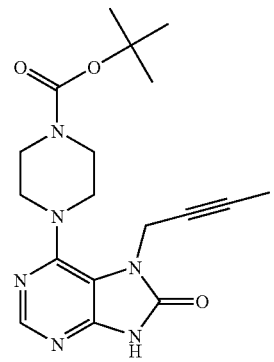

4-[7-(2-Butynyl)-9-(2-cyano-ethyl)-8-oxo-8,9-dihydro-7H-purin-6-yl]piperazine-1-carboxylic acid t-butyl ester (1.22 g) was dissolved in ethanol (20 mL). Sodium hydride (60%, in oil) (344 mg) was then added slowly to this solution. After stirring the reaction solution at room temperature for 72 hours, water (50 mL) and 1 N hydrochloric acid (10 mL) were added to the reaction solution, and this was extracted using ethyl acetate. The obtained organic layer was washed with water and saturated brine. The obtained organic layer was then dried over magnesium sulfate, and concentrated under reduced pressure to give the title compound (1.25 g).

¹H-NMR (CDCl₃)

δ 1.51 (s, 9H), 1.81 (t, J=2.4 Hz, 3H), 3.36 (m, 4H), 3.63 (m, 4H), 4.70 (q, J=2.4 Hz, 2H), 8.38 (s, 1H)

61f 7-(2-Butynyl)-6-(piperazin-1-yl)-9-(pyridin-3-yl)-7,9-dihydropurin-8-one trifluoroacetic acid salt

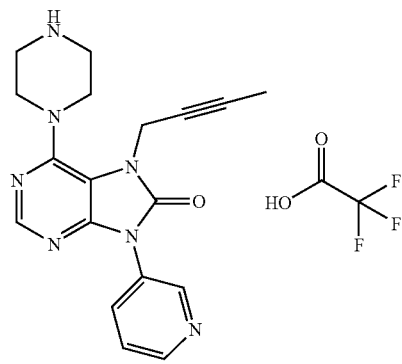

4-[7-(2-Butynyl)-8-oxo-8,9-dihydro-7H-purin-6-yl]piperazine-1-carboxylic acid t-butyl ester (12 mg) was dissolved in N,N-dimethylformamide (0.5 mL). Pyridine-3-boronic acid (10 mg), copper(II) acetate (5 mg), and pyridine (50 μL) were then added to this solution. The reaction solution was stirred at room temperature for 120 hours, and then water was added. This reaction solution was then extracted with ethyl acetate. The organic layer was concentrated, and the residue was dissolved in trifluoroacetic acid. This reaction solution was then stirred at room temperature for five minutes, and concentrated. The residue was purified by reverse phase high performance liquid chromatography to give the title compound (6.71 mg).

MS m/e (ESI) 350(M+H)+

EXAMPLE 62

7-(2-Butynyl)-9-phenyl-6-(piperazin-1-yl)-7,9-dihydropurin-8-one trifluoroacetic acid salt

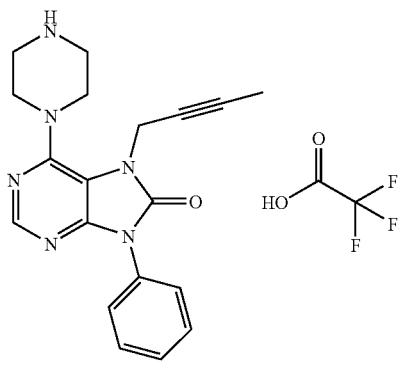

Using phenylboronic acid (10 mg) instead of the pyridine-3-boronic acid in Example 61f, the title compound (6.94 mg) was obtained by treatment similar to that of Example 61f.

MS m/e (ESI) 349(M+H)+

EXAMPLE 63

7-(2-Butynyl)-9-(furan-3-yl)-6-(piperazin-1-yl)-7,9-dihydropurin-8-one trifluoroacetic acid salt

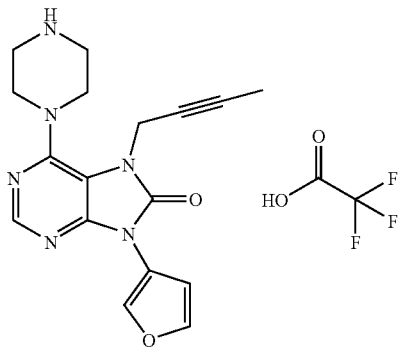

Using furan-3-boronic acid (10 mg) instead of the pyridine-3-boronic acid in Example 61f, the title compound (1.28 mg) was obtained by treatment similar to that of Example 61f, but at a reaction temperature of 50° C.

MS m/e (ESI) 339(M+H)+

EXAMPLE 64

7-(2-Butynyl)-9-(2-methoxy-pyrimidin-5-yl)-6-(piperazin-1-yl)-7,9-dihydropurin-8-one trifluoroacetic acid salt

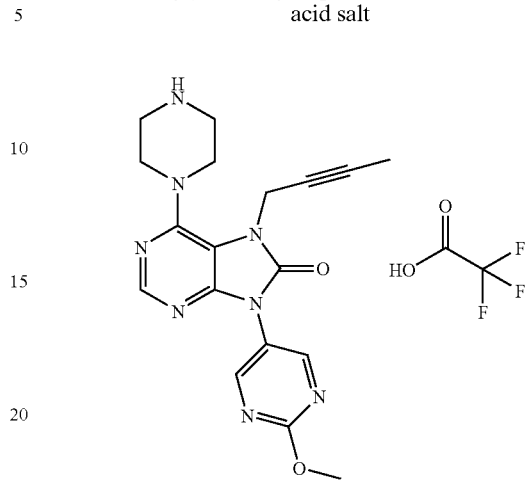

Using 2-methoxy-5-pyrimidineboronic acid (10 mg) instead of the pyridine-3-boronic acid in Example 61f, the title compound (2.52 mg) was obtained by treatment similar to that of Example 61f, but at a reaction temperature of 50° C. and over a reaction time of 48 hours.

$^1$H-NMR (CD$_3$OD)

δ 1.87 (t, J=2.0 Hz, 3H) 3.53 (m, 4H) 3.70 (m, 4H) 4.13 (s, 3H) 4.87 (q, J=2.0 Hz, 2H) 8.45 (s, 1H) 8.95 (s, 2H)

MS m/e (ESI) 381(M+H)+

EXAMPLE 65

7-(2-Butynyl)-9-(2-chloro-pyridin-4-yl)-6-(piperazin-1-yl)-7,9-dihydropurin-8-one trifluoroacetic acid salt

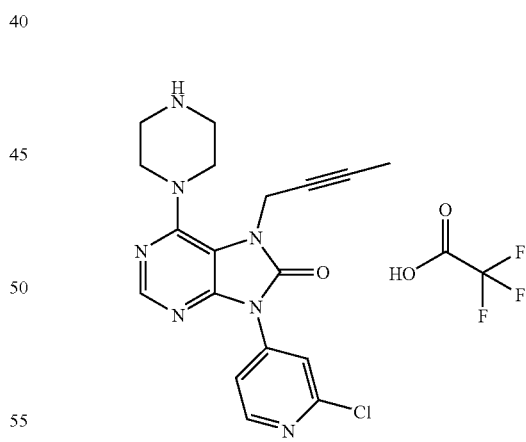

Using 2-chloropyridine-4-boronic acid (10 mg) instead of the pyridine-3-boronic acid in Example 61f, the title compound (4.48 mg) was obtained by treatment similar to that of Example 61f, but at a reaction temperature of 90° C. and over a reaction time of 48 hours.

$^1$H-NMR (CD$_3$OD)

δ 1.86 (t, J=2.4 Hz, 3H) 3.53 (m, 4H) 3.69 (m, 4H) 4.86 (q, J=2.4 Hz, 2H) 8.19 (dd, J=5.6, 2.0 Hz, 1H) 8.27 (d, J=2.0 Hz, 1H) 8.53 (s, 1H) 8.54 (d, J=5.6 Hz, 1H)

MS m/e (ESI) 384(M+H)+

EXAMPLE 66

7-(2-Butynyl)-9-(6-methoxy-pyridin-3-yl)-6-(piperazin-1-yl)-7,9-dihydropurin-8-one trifluoroacetic acid salt

66a

4-[7-(2-Butynyl)-9-(6-methoxy-pyridin-3-yl)-8-oxo-8,9-dihydro-7H-purin-6-yl]piperazine-1-carboxylic acid t-butyl ester

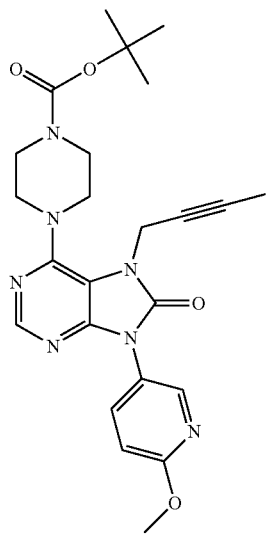

Using 5-methoxy-2-aminopyridine instead of the 3-aminopropionitrile in Example 61b, the title compound was obtained by treatment similar to that of Examples 61b-d.

$^1$H-NMR (CDCl$_3$)

δ 1.50 (s, 9H), 1.82 (t, J=2.4 Hz, 3H), 3.36 (m, 4H), 3.64 (m, 4H), 3.97 (s, 3H), 4.78 (q, J=2.4 Hz, 2H), 6.87 (d, J=8.8 Hz, 1H), 7.83 (dd, J=8.8, 2.8 Hz, 1H), 8.36 (S, 1H), 8.44 (d, J=2.8 Hz, 1H)

66b 7-(2-Butynyl)-9-(6-methoxy-pyridin-3-yl)-6-(piperazin-1-yl)-7,9-dihydropurin-8-one trifluoroacetic acid salt

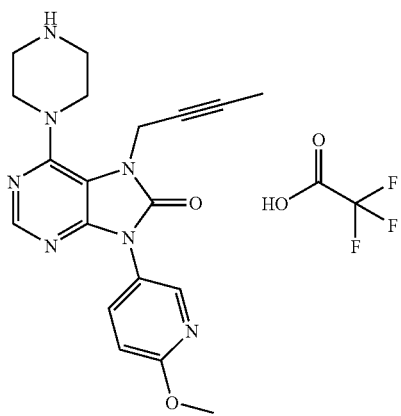

4-[7-(2-Butynyl)-9-(6-methoxy-pyridin-3-yl)-8-oxo-8,9-dihydro-7H-purin-6-yl]piperazine-1-carboxylic acid t-butyl ester (60 mg) was dissolved in trifluoroacetic acid, and this reaction solution was stirred at room temperature for five minutes, and then concentrated. The residue was purified by reverse phase high performance liquid chromatography to give the title compound (48.25 mg).

$^1$H-NMR (CD$_3$OD)

δ 1.87 (t, J=2.4 Hz, 3H), 3.53 (m, 4H), 3.69 (m, 4H), 4.02 (s, 3H), 4.86 (q, J=2.4 Hz, 2H), 7.00 (dd, J=8.8, 0.8 Hz, 1H), 7.95 (dd, J=8.8, 2.8 Hz, 1H), 8.42 (S, 1H), 8.43 (d, J=2.8, 0.8 Hz, 1H)

MS m/e (ESI) 380(M+H)$^+$

EXAMPLE 67

7-(2-Butynyl)-9-(6-oxo-16-dihydro-pyridin-3-yl)-6-(piperazin-1-yl)-7,9-dihydropurin-8-one trifluoroacetic acid salt

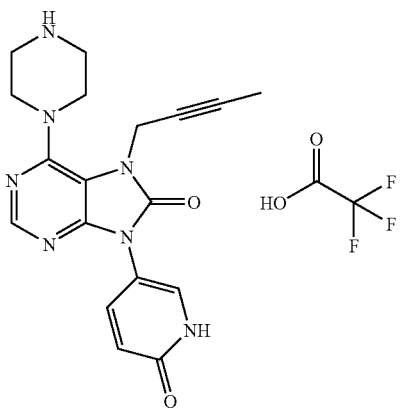

4-[7-(2-Butynyl)-9-(6-methoxy-pyridin-3-yl)-8-oxo-8,9-dihydro-7H-purin-6-yl]piperazine-1-carboxylic acid t-butyl ester (compound 66a) (40 mg) was dissolved in ethanol (0.2 mL), and then 4 N hydrochloric acid/dioxane (0.2 mL) was added to this solution. The reaction solution was stirred at 90° C. overnight, and then concentrated. The residue was purified by reverse phase high performance liquid chromatography to give the title compound (17.58 mg).

$^1$H-NMR (CD$_3$OD)

δ 1.86 (t, J=2.4 Hz, 3H), 3.52 (m, 4H), 3.68 (m, 4H), 4.84 (q, J=2.4 Hz, 2H), 6.70 (d, J=10.4 Hz, 1H), 7.83-7.86 (m, 2H), 8.43 (s, 1H)

MS m/e (ESI) 366(M+H)$^+$

EXAMPLE 68

7-(2-Butynyl)-9-(1-methyl-6-oxo-16-dihydro-pyridin-3-yl)-6-(piperazin-1-yl)-7,9-dihydropurin-8-one trifluoroacetic acid

68a

4-[7-(2-Butynyl)-9-(1-methyl-6-oxo-1,6-dihydropyridin-3-yl)-8-oxo-8,9-dihydro-7H-purin-6-yl]piperazine-1-carboxylic acid t-butyl ester

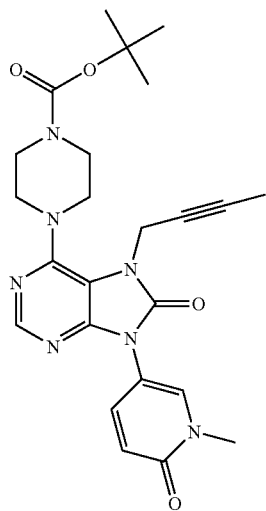

Using 5-amino-1-methyl-1H-pyridin-2-one instead of the 3-aminopropionitrile in Example 61b, the title compound was obtained by treatment similar to that of Examples 61b-d.

68b 7-(2-Butynyl)-9-(1-methyl-6-oxo-1,6-dihydro-pyridin-3-yl)-6-(piperazin-1-yl)-7,9-dihydropurin-8-one trifluoroacetic acid salt

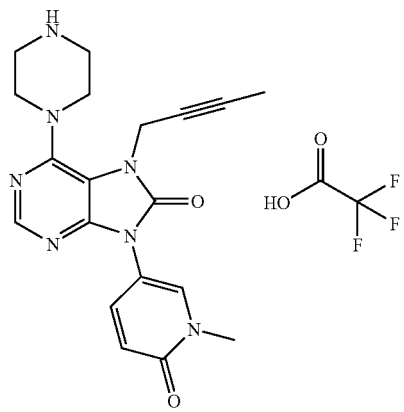

4-[7-(2-Butynyl)-9-(1-methyl-6-oxo-1,6-dihydro-pyridin-3-yl)-8-oxo-8,9-dihydro-7H-purin-6-yl]piperazine-1-carboxylic acid t-butyl ester (15 mg) was dissolved in trifluoroacetic acid, and this reaction solution was stirred at room temperature for five minutes and then concentrated. The residue was purified by reverse phase high performance liquid chromatography to give the title compound (10.52 mg).

$^1$H-NMR (CD$_3$OD)
δ 1.88 (t, J=2.4 Hz, 3H), 2.74 (s, 3H), 3.52 (m, 4H), 3.68 (m, 4H), 4.72 (q, J=2.4 Hz, 2H), 6.70 (d, J=9.6 Hz, 1H), 7.77 (dd, J=9.6, 2.8 Hz, 1H), 8.09 (d, J=2.8 Hz, 1H), 8.43 (S, 1H)
MS m/e (ESI) 380(M+H)$^+$

EXAMPLE 69

9-Allyl-7-(2-butynyl)-6-(piperazin-1-yl)-7,9-dihydropurin-8-one trifluoroacetic acid salt

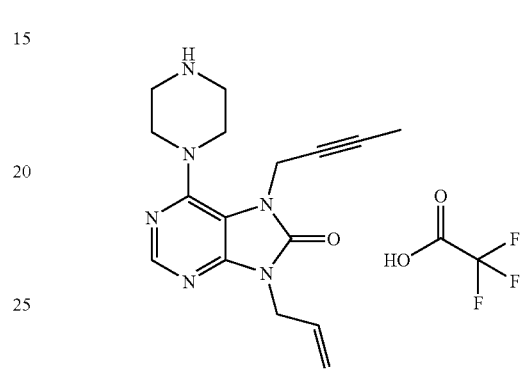

4-[7-(2-Butynyl)-8-oxo-8,9-dihydro-7H-purin-6-yl]piperazine-1-carboxylic acid t-butyl ester (compound 61e) (15 mg) was dissolved in N,N-dimethylformamide (0.5 mL), and then allyl bromide (25 µL) and anhydrous potassium carbonate (10 mg) were added to this solution. After stirring the reaction solution at room temperature for 14 hours, water was added to the reaction solution, and this was extracted with ethyl acetate. The obtained organic layer was concentrated, and the residue was dissolved in trifluoroacetic acid. This reaction solution was then stirred at room temperature for five minutes and concentrated. The residue was purified by reverse phase high performance liquid chromatography to give the title compound (8.00 mg).
MS m/e (ESI) 313(M+H)$^+$

EXAMPLE 70

7-(2-Butynyl)-6-(piperazin-1-yl)-9-(2-propynyl)-7,9-dihydropurin-8-one trifluoroacetic acid salt

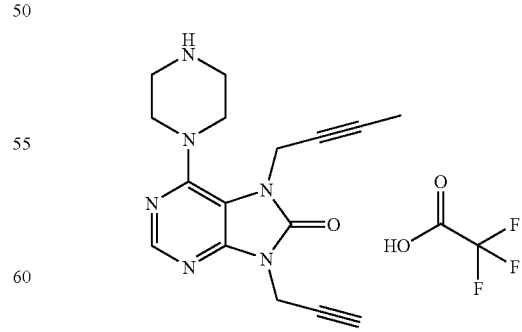

Using propargyl bromide (25 µL) instead of the allyl bromide in Example 69, the title compound (3.71 mg) was obtained by treatment similar to that of Example 69.
MS m/e (ESI) 311(M+H)$^+$

EXAMPLE 71

2-[7-(2-Butynyl)-8-oxo-6-(piperazin-1-yl)-7,8-dihydropurin-9-yl]acetamide trifluoroacetic acid salt

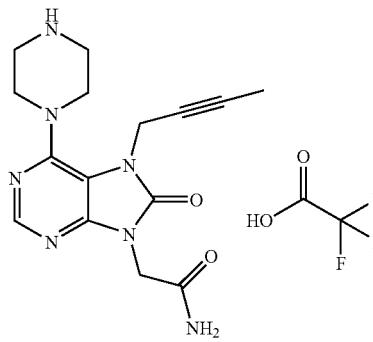

Using 2-bromoacetamide (20 mg) instead of the allyl bromide in Example 69, the title compound (7.55 mg) was obtained by treatment similar to that of Example 69.

MS m/e (ESI) 330(M+H)$^+$

EXAMPLE 72

7-(2-Butynyl)-9-cyclopropylmethyl-6-(piperazin-1-yl)-7,9-dihydropurin-8-one trifluoroacetic acid salt

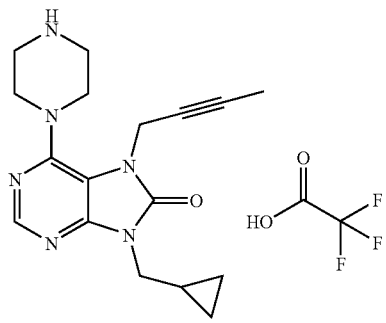

Using bromomethylcyclopropane (25 μL) instead of the allyl bromide in Example 69, the title compound (7.28 mg) was obtained by treatment similar to that of Example 69.

MS m/e (ESI) 327(M+H)$^+$

EXAMPLE 73

4-[7-(2-Butynyl)-8-oxo-6-(piperazin-1-yl)-7,8-dihydropurin-9-ylmethyl]benzonitrile trifluoroacetic acid salt

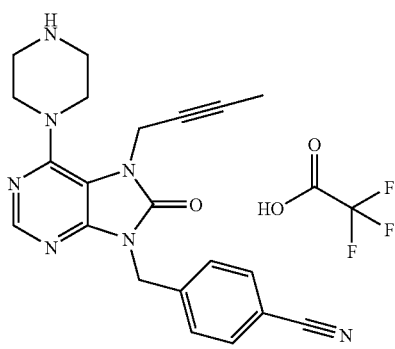

Using 4-cyano-benzylbromide (20 mg) instead of the allyl bromide in Example 69, the title compound (9.56 mg) was obtained by treatment similar to that of Example 69.

MS m/e (ESI) 388(M+H)$^+$

EXAMPLE 74

7-(2-Butynyl)-9-phenethyl-6-(piperazin-1-yl)-7,9-dihydropurin-8-one trifluoroacetic acid salt

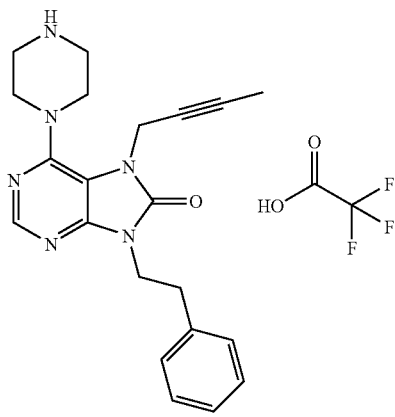

Using phenethylbromide (25 μL) instead of the allyl bromide in Example 69, the title compound (7.14 mg) was obtained by treatment similar to that of Example 69

MS m/e (ESI) 377(M+H)$^+$

EXAMPLE 75

7-(2-Butynyl)-6-(piperazin-1-yl)-7,9-dihydropurin-8-one trifluoroacetic acid salt

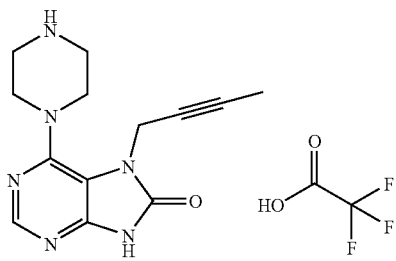

4-[7-(2-Butynyl)-8-oxo-8,9-dihydro-7H-purin-6-yl]piperazine-1-carboxylic acid t-butyl ester (compound 61e) (12 mg) was dissolved in trifluoroacetic acid. This reaction solution was stirred at room temperature for five minutes, and then concentrated. The residue was purified by reverse phase high performance liquid chromatography to give the title compound (8.86 mg).

MS m/e (ESI) 273(M+H)$^+$

EXAMPLE 76

7-(2-Butynyl)-9-methyl-6-(piperazin-1-yl-7,9-dihydropurin-8-one trifluoroacetic acid salt 76a 4-(9H-purin-6-yl)-piperazine-1-carboxylic acid t-butyl ester

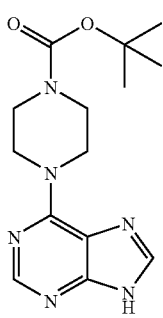

To a solution of 6-chloropurine [CAS No. 87-42-3] (7.73 g) in ethanol (100 mL), diisopropylethylamine (26.1 mL) and piperazine-1-carboxylic acid t-butylester (11.16 g) were added, and this was heated under reflux for 16 hours. The solvent was removed under reduced pressure, and the residue was suspended in water (200 mL). The precipitate was collected by filtration, and then washed twice with 50 mL of water and twice with 50 mL of t-butyl methyl ether to give the title compound (13.99 g).

$^1$H-NMR (CDCl$_3$)

1.50 (s, 9H), 3.58-3.62 (m, 4H), 4.29-4.37 (m, 4H,), 7.90 (s, 1H), 8.35 (s, 1H)

76b 4-(9-Methyl-9H-purin-6-yl)-piperazine-1-carboxylic acid t-butyl ester

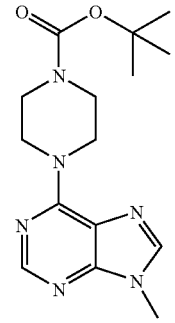

Potassium carbonate (1.52 g) and methyl iodide (0.94 mL) were added to a solution of 4-(9H-purin-6-yl)-piperazine-1-carboxylic acid t-butyl ester (3.04 g) in N,N-dimethylformamide (100 mL), and this was stirred at room temperature for 16 hours. Ethyl acetate (300 mL) and water (100 mL) were added, the organic layer was washed twice with 100 mL of water and then once with 100 mL of saturated aqueous sodium chloride solution, and then dried over anhydrous magnesium sulfate. The organic layer was filtered, and concentrated under reduced pressure to give the title compound (2.70 g).

$^1$H-NMR (CDCl$_3$)

1.50 (s, 9H), 3.56-3.61 (m, 4H), 3.83 (s, 3H), 4.26-4.34 (m, 4H), 7.73 (s, 1H), 8.36 (s, 1H)

76c 4-(8-Chloro-9-methyl-9H-purin-6-yl)-piperazine-1-carboxylic acid t-butyl ester

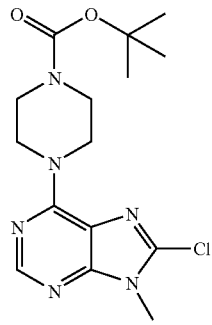

N-chlorosuccinimide (1.25 g) was added to a solution of 4-(9-methyl-9H-purin-6-yl)-piperazine-1-carboxylic acid t-butyl ester (2.70 g) in N,N-dimethylformamide (30 mL), and this was stirred at room temperature for 20 hours. Ethyl acetate (200 mL) and water (50 mL) were added, the organic layer was washed twice with 50 mL of water and then once with 50 mL of saturated aqueous solution of sodium chloride, and dried over anhydrous magnesium sulfate. The organic layer was filtered and then concentrated under reduced pressure. The residue was purified by silica gel chromatography, and the ethyl acetate:hexane 4:1 fraction gave the title compound (1.97 g).

$^1$H-NMR (CDCl$_3$)

1.50 (s, 9H), 3.56-3.60 (m, 4H), 3.76 (s, 3H), 4.18-4.25 (m, 4H), 8.34 (s, 1H)

76d 4-(9-Methyl-8-oxo-8,9-dihydro-7H-purin-6-yl)-piperazine-1-carboxylic acid t-butyl ester

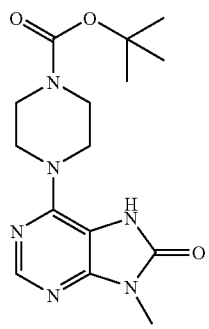

Sodium acetate (0.168 g) and sodium bicarbonate (0.100 g) were added to a solution of 4-(8-chloro-9-methyl-9H-purin-6-yl)-piperazine-1-carboxylic acid t-butyl ester (0.353 g) in dimethylsulfoxide (5 mL). This was then heated at 135° C. for 64 hours. The reaction solution was filtered, and was directly loaded onto a column for purification by reverse phase high performance liquid chromatography to give the title compound (0.179 g).

$^1$H-NMR (CDCl$_3$)

1.50 (s, 9H), 3.47 (s, 3H), 3.58-3.62 (m, 4H), 3.72-3.77 (m, 4H), 8.33 (s, 1H), 10.87-10.92 (br.s, 1H)

76e 7-(2-Butynyl)-9-methyl-6-(piperazin-1-yl)-7,9-dihydropurin-8-one trifluoroacetic acid

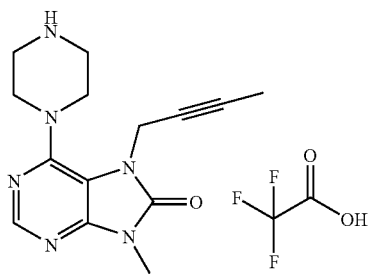

Potassium carbonate (6 mg) and 1-bromo-2-butyne (4 μL) were added to a solution of 4-(9-methyl-8-oxo-8,9-dihydro-7H-purin-6-yl)-piperazine-1-carboxylic acid t-butyl ester (10 mg) in N,N-dimethylformamide (0.5 mL). This was stirred at room temperature for 15 hours. Ethyl acetate (1 mL) and water (1 mL) were added, and the organic layer was concentrated. The residue was dissolved in dichloromethane (0.5 mL) and trifluoroacetic acid (0.5 mL). This was stirred for two hours, and the solvent was then removed. The residue was purified by reverse phase high performance liquid chromatography to give the title compound (0.0012 g).

MS m/e (ESI) 287.20 (M+H)$^+$

EXAMPLE 77

9-Methyl-7-(3-methyl-2-butenyl)-6-(piperazin-1-yl)-7,9-dihydropurin-8-one trifluoroacetic acid salt

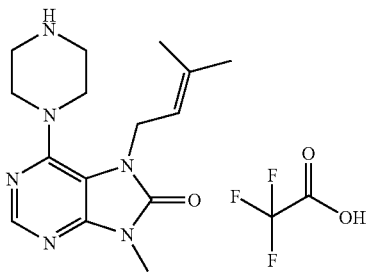

Using 1-bromo-3-methyl-2-butene (5 μL) instead of the 1-bromo-2-butyne in Example 76e, the title compound (4.3 mg) was obtained by treatment similar to that of Example 76e.

MS m/e (ESI) 303.26 (M+H)$^+$

EXAMPLE 78

7-Benzyl-9-methyl-6-(piperazin-1-yl)-7,9-dihydropurin-8-one trifluoroacetic acid salt

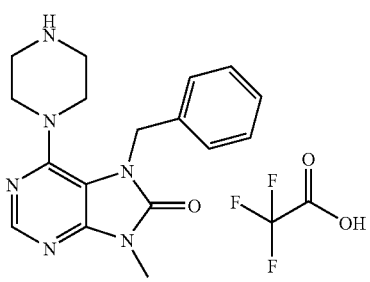

Using benzyl bromide (5 μL) instead of the 1-bromo-2-butyne in Example 76e, the title compound (4.8 mg) was obtained by treatment similar to that of Example 76e.

MS m/e (ESI) 325.23 (M+H)$^+$

EXAMPLE 79

2-[7-(2-Butynyl)-8-oxo-6-piperazin-1-yl-7,8-dihydropurin-9-ylmethyl]benzonitrile trifluoroacetic acid salt 79a 4-[9-(2-Cyanobenzyl)-9H-purin-6-yl]-piperazine-1-carboxylic acid t-butyl ester

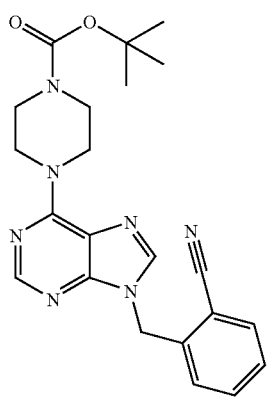

Potassium carbonate (0.76 g) and (2-bromomethyl)benzonitrile (1.08 g) were added to a solution of 4-(9H-purin-6-yl)-piperazine-1-carboxylic acid t-butyl ester (compound 76a) (1.52 g) in N,N-dimethylformamide (100 mL). This was then stirred at room temperature for 16 hours. Ethyl acetate (500 mL) and water (500 mL) were added to the reaction solution, and this was filtered. The organic layer was washed twice with 200 mL of water and then once with 200 mL of saturated aqueous sodium chloride solution. The solid collected by filtration was dissolved in dichloromethane (500 mL). This solution was then washed sequentially with 5% aqueous solution of sodium bicarbonate (200 mL) and water (200 mL), combined with the ethyl acetate organic layer, and then dried over anhydrous magnesium sulfate. The organic layer was filtered, concentrated under reduced pressure, and the residue was recrystallized from toluene to give the title compound (2.04 g).

$^1$H-NMR (CDCl$_3$)

1.50 (s, 9H), 3.53-3.61 (m, 4H), 4.04-4.15 (br.s, 4H), 5.58 (s, 2H), 7.37 (d, J=7.5 Hz, 1H), 7.42 (t, J=7.5 Hz, 1H), 7.54 (t, J=7.5 Hz, 1H), 7.70 (d, J=7.5 Hz, 1H), 7.89 (s, 1H), 8.36 (s, 1H)

79b)

4-[8-Chloro-9-(2-cyanobenzyl)-9H-purin-6-yl]-piperazine-1-carboxylic acid t-butyl ester

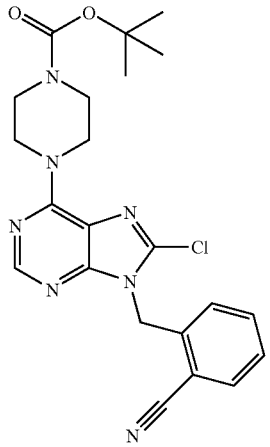

4-[9-(2-Cyanobenzyl)-9H-purin-6-yl]-piperazine-1-carboxylic acid t-butyl ester (0.419 g) was suspended in N,N-dimethylformamide (80 mL), and then N-chlorosuccinimide (0.160 g) was added. This was stirred at room temperature for 72 hours. N-chlorosuccinimide (0.160 g) was added again, and this was then heated at 60° C. for 18 hours. Ethyl acetate (200 mL) and water (100 mL) were then added, and the organic layer was washed twice with 50 mL of water and then once with 5 mL of saturated aqueous sodium chloride solution. This was then dried over anhydrous magnesium sulfate, filtered and concentrated under reduced pressure, and then the residue was purified by silica gel chromatography. The dichloromethane:ethyl acetate 7:3 fraction gave the title compound (0.100 g).

$^1$H-NMR (CDCl$_3$)

1.50 (s, 9H), 3.53-3.60 (m, 4H), 4.18-4.27 (br.s, 4H), 5.62 (s, 2H), 6.99 (d, J=7.4 Hz, 1H), 7.40 (t, J=7.4 Hz, 1H), 7.49 (t, J=7.4 Hz, 1H), 7.71 (d, J=7.4 Hz, 1H), 8.31 (s, 1H)

79c

4-[9-(2-Cyanobenzyl)-8-oxo-8,9-dihydro-7H-purin-6-yl]-piperazine-1-carboxylic acid t-butyl ester

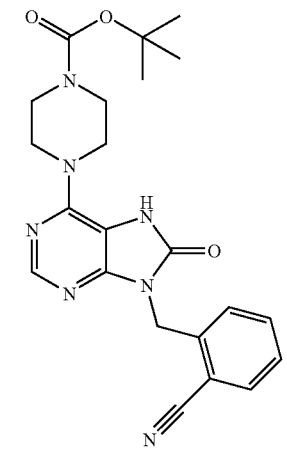

Sodium acetate (0.168 g) and sodium bicarbonate (0.100 g) were added to a solution of 4-[8-chloro-9-(2-cyanobenzyl)-

9H-purin-6-yl]-piperazine-1-carboxylic acid t-butyl ester (0.100 g) in dimethylsulfoxide (3 mL). This was then heated at 135° C. for 45 hours. The reaction solution was filtered, and then directly loaded onto a column for purification by reverse phase high performance liquid chromatography to give the title compound (0.044 g).

$^1$H-NMR (CDCl$_3$)

1.50 (s, 9H), 3.53-3.57 (m, 4H), 3.65-3.70 (m, 4H), 5.34 (s, 2H), 7.38 (d, J=7.5 Hz, 1H), 7.39 (t, J=7.5 Hz, 1H), 7.53 (d, J=7.5 Hz, 1H), 7.70 (d, J=7.5 Hz, 1H), 8.25 (s, 1H), 10.87 (s, 1H)

79d

2-[7-(2-Butynyl-8-oxo-6-piperazin-1-yl-7,8-dihydro-purin-9-ylmethyl]benzonitrile trifluoroacetic acid salt

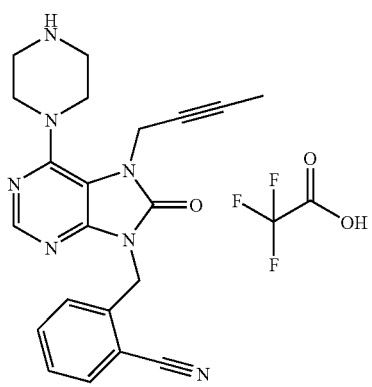

Potassium carbonate (0.017 g) and 1-bromo-2-butyne (0.011 mL) were added to a solution of 4-[9-(2-cyanobenzyl)-8-oxo-8,9-dihydro-7H-purin-6-yl]-piperazine-1-carboxylic acid t-butyl ester (0.044 g) in N,N-dimethylformamide (3 mL). This was then stirred at room temperature for 72 hours. Ethyl acetate (10 mL) and water (10 mL) were added, and the organic layer was dried over anhydrous magnesium sulfate, filtered, and then concentrated under reduced pressure. The residue was dissolved in dichloromethane (3 mL) and trifluoroacetic acid (3 mL) was added. This was stirred for 2 hours, toluene (10 mL) was added, and this was then concentrated under reduced pressure. The residue was purified by reverse phase high performance liquid chromatography to give the title compound (0.0162 g).

$^1$H-NMR (CDCl$_3$)

1.80 (s, 3H), 3.30-3.45 (br.s, 4H), 3.63-3.75 (br.s, 4H), 4.70 (s, 2H), 5.35 (s, 2H), 7.30-7.41 (m, 2H), 7.52 (d, J=7.5 Hz, 1H), 7.63 (d, J=7.5 Hz, 1H), 8.39 (s, 1H)

MS m/e (ESI) 388.18 (M+H)$^+$

EXAMPLE 80

2-(3-Benzyl-2-oxo-4-piperazin-1-yl-2,3-dihydroimidazo[4.5-c]pyridin-1-ylmethyl)benzonitrile 80a Allyl-(3-nitropyridin-4-yl)amine

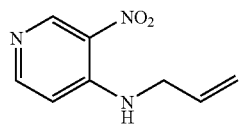

Allyl amine (40 mL) was added to a solution of 4-ethoxy-3-nitropyridine hydrochloride [CAS No. 94602-04-7] (18.0 g) in ethanol (400 mL), and this was heated under reflux for eight hours. The reaction solution was concentrated under reduced pressure, and the residue was purified by silica gel column chromatography. The fraction eluted by ethyl acetate-hexane (1:1) gave the title compound (13.6 g).

$^1$H-NMR (CDCl$_3$) δ 4.00 (m, 2H), 5.29-5.35 (m, 2H), 5.87-5.98 (m, 1H), 6.63 (d, J=6.5 Hz, 1H), 8.30 (d, J=6.5 Hz, 1H), 8.31 (br.s, 1H), 9.23 (s, 1H)

80b

N*4*-Allyl-2-chloropyridin-3,4-diamine

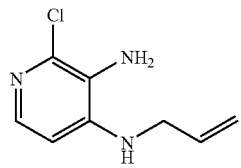

35% Hydrochloric acid (55 mL) was added to allyl(3-nitropyridin-4-yl) amine (3.02 g) and this was heated to 90° C. Tin chloride (19.1 g) was added, and this was reacted at 90° C. for 30 minutes. The reaction solution was cooled on iced water, and 250 mL of iced water was added. The reaction solution was concentrated under reduced pressure, and then a saturated solution of ammonia-methanol (250 mL) was added, and this was stirred for 20 hours. Ethyl acetate (750 mL) was then added, and this was filtered through celite, and then concentrated under reduced pressure. The residue was purified by silica gel column chromatography, and the fraction eluted by ethyl acetate-hexane (1:1) gave the title compound (2.88 g).

$^1$H-NMR (CDCl$_3$)

δ 3.29-3.58 (br.s, 2H), 3.84 (d, J=6.3 Hz, 2H), 4.26-4.37 (br.s, 1H), 5.24 (d, J=11.0 Hz, 1H), 5.29 (d, J=16.0 Hz, 1H), 5.85-5.98 (ddt, J=16.0, 11.0, 6.3 Hz, 1H), 6.43 (d, J=6.5 Hz, 1H), 7.66 (d, J=6.5 Hz, 1H)

80c

1-Allyl-4-chloro-1,3-dihydroimidazo[4.5-c]pyridin-2-one

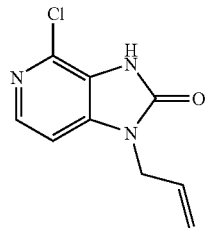

A solution of N,N'-disuccinimidyl carbonate (4.46 g) in acetonitrile (400 mL) was added to a solution of N*4*-allyl-2-chloropyridine-3,4-diamine (2.88 g) in acetonitrile. This was then heated under reflux for 70 hours. The solvent was removed under reduced pressure, the residue was dissolved in ethyl acetate (500 mL) and water (300 mL). The organic layer was then washed twice with 100 mL of 1 N hydrochloric acid and then once with 100 mL of saturated aqueous sodium chloride solution. This was then dried over magnesium sulfate, and concentrated under reduced pressure. The residue was purified by silica gel column chromatography, and the fraction eluted by ethyl acetate-dichloromethane (1:1) gave the title compound (2.30 g).

$^1$H-NMR (CDCl$_3$)

δ 4.51 (d, J=5.7 Hz, 2H), 5.25 (d, J=16.0 Hz, 1H), 5.30 (d, J=10.9 Hz, 1H), 5.85-5.95 (ddt, J=16.0, 10.9, 5.7 Hz, 1H), 6.91 (d, J=6.9 Hz, 1H), 8.10 (d, J=6.9 Hz, 1H), 8.99 (br.s, 1H)

80d

1-Allyl-3-benzyl-4-chloro-1,3-dihydroimidazo[4.5-c]pyridin-2-one

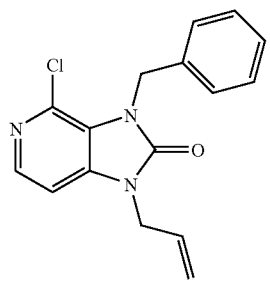

Potassium carbonate (0.76 g) and benzylbromide (0.94 g) were added to a solution of 1-allyl-4-chloro-1,3-dihydroimidazo[4.5-c]pyridin-2-one (1.05 g) in N,N-dimethylformamide (50 mL). This was stirred at room temperature for 14 hours. Water (300 mL) and ethyl acetate (300 mL) were added, and the organic layer was washed three times with 100 mL of water and then once with 100 mL of saturated aqueous sodium chloride solution, then was dried over magnesium sulfate, and concentrated under reduced pressure to give the title compound (1.57 g).

$^1$H-NMR (CDCl$_3$)

δ 4.56 (d, J=5.7 Hz, 2H), 5.23 (d, J=16.0 Hz, 1H), 5.30 (d, J=10.9 Hz, 1H), 5.44 (s, 2H), 5.85-5.95 (ddt, J=16.0, 10.9, 5.7 Hz, 1H), 6.91 (d, J=6.9 Hz, 1H), 7.25-7.34 (m, 5H), 8.08 (d, J=6.9 Hz, 1H), 8.99 (br.s, 1H)

80e

3-Benzyl-4-chloro-1,3-dihydroimidazo[4.5-c]pyridin-2-one

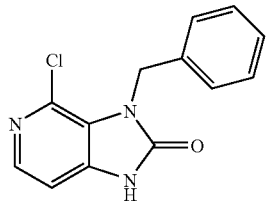

Water (1.5 mL), 4-methylmorpholin-N-oxide (1.06 g), 2% aqueous osmic acid solution (3 mL), and a solution of sodium periodate (1.94 g) in water (6 mL) were added to a solution of 1-allyl-3-benzyl-4-chloro-1,3-dihydroimidazo[4.5-c]pyridin-2-one (0.75 g) in 1,4-dioxane (15 mL). This was then heated at 60° C. for 18 hours. Water (200 mL) was added, and this was extracted with ethyl acetate (100 mL). The obtained organic layer was washed twice with 50 mL of water and then once with 50 mL of saturated aqueous sodium chloride solution, dried over magnesium sulfate, and then concentrated under reduced pressure. The residue was purified by silica gel column chromatography, and the fraction eluted by ethyl acetate-hexane (1:1) gave the title compound (0.38 g).

$^1$H-NMR (CDCl$_3$)

δ 5.44 (s, 2H), 7.01 (d, J=6.5 Hz, 1H), 7.30-7.38 (m, 5H), 8.08 (d, J=6.5 Hz, 1H), 9.18 (s, 1H)

80f 2-(3-Benzyl-4-chloro-2-oxo-2,3-dihydroimidazo[4.5-c]pyridin-1-ylmethyl)benzonitrile

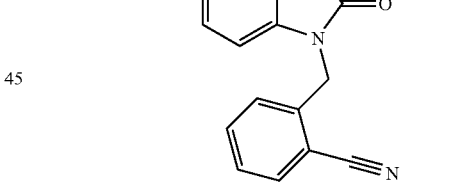

Potassium carbonate (0.152 g) and (2-bromomethyl)benzonitrile (0.216 g) were added to a solution of 3-benzyl-4-chloro1,3-dihydroimidazo[4.5-c]pyridin-2-one (0.259 g) in N,N-dimethylformamide (5 mL). This was stirred at room temperature for 16 hours. Ethyl acetate (60 mL) and water (30 mL) were added, and the organic layer was washed twice with 30 mL of water and once with 30 mL of saturated aqueous sodium chloride solution. This was then dried over anhydrous magnesium sulfate. The organic layer was filtered and concentrated under reduced pressure, and the residue was then purified by silica gel chromatography. The ethyl acetate:hexane 3:2 fraction gave the title compound (0.364 g).

$^1$H-NMR (CDCl$_3$)

5.35 (s, 2H), 5.49 (s, 2H), 6.96 (d, J=5.6 Hz, 1H), 7.24-7.35 (m, 5H), 7.41 (d, J=7.4 Hz, 1H), 7.44 (t, J=7.4 Hz, 1H), 7.57 (t, J=7.4 Hz, 1H), 7.73 (d, J=7.4 Hz, 1H), 8.06 (d, J=5.6 Hz, 1H)

80g 2-(3-Benzyl-2-oxo-4-piperazin-1-yl-2,3-dihydroimidazo[4.5-c]pyridin-1-ylmethyl)benzonitrile

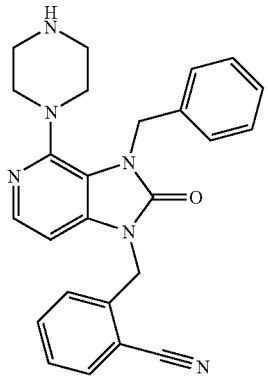

Under a Nitrogen Atmosphere, 2-(3-benzyl-4-chloro-2-oxo-2,3-dihydroimidazo[4.5-c]pyridin-1-ylmethyl)benzonitrile (0.364 g) and piperazine-1-carboxylic acid t-butyl ester (0.543 g) were heated at 170° C. for 12 hours. The residue was cooled, and then purified by silica gel chromatography using amine-treated silica.

The fraction eluted by ethyl acetate:hexane 4:1 to ethyl acetate:methanol 98:2 gave the title compound (0.150 g).

$^1$H-NMR (CDCl$_3$)

2.96-3.00 (m, 4H), 3.01-3.06 (m, 4H), 5.28 (s, 2H), 5.40 (s, 2H), 6.74 (d, J=5.6 Hz, 1H), 7.21-7.33 (m, 6H), 7.39 (t, J=7.4 Hz, 1H), 7.49 (t, J=7.4 Hz, 1H), 7.68 (d, J=7.4 Hz, 1H), 8.02 (d, J=5.6 Hz, 1H)

EXAMPLE 81

2-[3-Benzyl-1-(2-cyanobenzyl)-2-oxo-4-piperazin-1-yl-2,3-dihydro-1H-imidazo[4.5-c]pyridin-7-yloxy]-benzamide trifluoroacetic acid salt 81a 4-[3-Benzyl-1-(2-cyanobenzyl)-2-oxo-1H-imidazo[4.5-c]pyridin-4-yl]-piperazine-1-carboxylic acid t-butyl ester

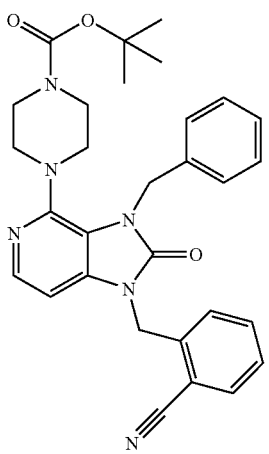

Di-t-butyl dicarbonate (0.094 g) and triethylamine (0.050 mL) were added to a solution of 2-(3-benzyl-2-oxo-4-piperazin-1-yl-2,3-dihydroimidazo[4.5-c]pyridin-1-ylmethyl)benzonitrile (compound 80 g) (0.146 g) in dichloromethane (10 mL). This was stirred at room temperature for 15 hours. The solvent was removed under reduced pressure, and the residue was purified by silica gel chromatography. The hexane:ethyl acetate 7:3 fraction gave the title compound (0.121 g).

$^1$H-NMR (CDCl$_3$)

1.46 (s, 9H), 2.95-3.00 (m, 4H), 3.41-3.53 (br.s, 4H), 5.30 (s, 2H), 5.40 (s, 2H), 6.78 (d, J=5.6 Hz, 1H), 7.20-7.25 (m, 5H), 7.31 (d, J=7.5 Hz, 1H), 7.40 (t, J=7.5 Hz, 1H), 7.51 (t, J=7.5 Hz, 1H), 7.69 (d, J=7.5 Hz, 1H), 8.02 (d, J=5.6 Hz, 1H)

81b

4-[3-Benzyl-7-bromo-1-(2-cyanobenzyl)-2-oxo-1H-imidazo[4.5-c]pyridin-4-yl]-piperazine-1-carboxylic acid t-butyl ester

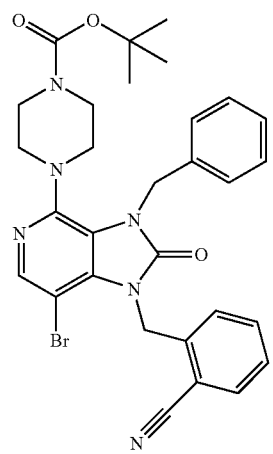

Sodium bicarbonate (0.029 g) and N-bromosuccinimide (0.044 g) were added to a solution of 4-[3-benzyl-1-(2-cyanobenzyl)-2-oxo-1H-imidazo[4.5-c]pyridin-4-yl]-piperazine-1-carboxylic acid t-butyl ester (0.121 g) in acetonitrile (5 mL). This was then stirred at room temperature for 15 hours. Ethyl acetate (100 mL) and water (50 mL) were added, and the organic layer was dried over anhydrous magnesium sulfate, filtered, and then concentrated under reduced pressure. The residue was purified by silica gel chromatography, and the hexane:ethyl acetate 7:3 fraction gave the title compound (0.148 g).

$^1$H-NMR (CDCl$_3$)

1.46 (s, 9H), 2.97-3.01 (m, 4H), 3.28-3.69 (br.s, 4H), 5.42 (s, 2H), 5.70 (s, 2H), 6.75 (d, J=7.5 Hz, 1H), 7.22-7.31 (m, 5H), 7.36 (t, J=7.5 Hz, 1H), 7.43 (t, J=7.5 Hz, 1H), 7.69 (d, J=7.5 Hz, 1H), 8.03 (s, 1H)

81c

4-[3-Benzyl-7-(2-carbamoylphenoxy)-1-(2-cyanobenzyl)-2-oxo-2,3-dihydro-1H-imidazo[4.5-c]pyridin-4-yl]-piperazine-1-carboxylic acid t-butyl ester

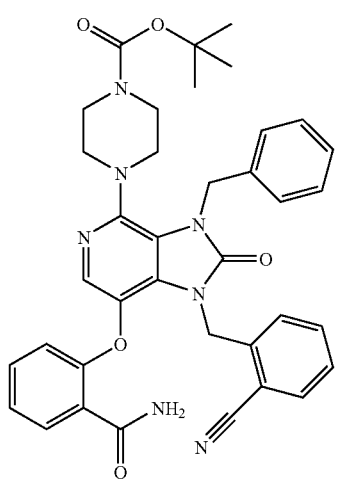

Salicylamide (0.056 g), cesium carbonate (0.130 g), 2,2,6,6-tetramethyl-3,5-heptanedione (0.005 mL), and copper(I) chloride (0.010 g) were added to a solution of 4-[3-benzyl-7-bromo-1-(2-cyanobenzyl)-2-oxo-1H-imidazo[4.5-c]pyridin-4-yl]-piperazine-1-car boxylic acid t-butyl ester (0.123 g) in 1-methyl-2-pyrolidone (2 mL). This was then heated at 130° C. for 22 hours under a nitrogen atmosphere. The reaction solution was cooled, t-butyl methyl ether was added, and this was filtered through celite. The celite was washed with ethyl acetate (25 mL), and the organic layers were combined, and then washed sequentially with 2 N hydrochloric acid (10 mL), 0.5 N hydrochloric acid (10 mL), 1 N aqueous sodium hydroxide solution (10 mL), and saturated aqueous sodium chloride solution (10 mL). This was then dried over anhydrous magnesium sulfate, filtered, and concentrated under reduced pressure. The residue was purified by reverse phase high performance liquid chromatography to give the title compound (0.023 g).

¹H-NMR (CDCl₃)

1.46 (s, 9H), 2.99-3.07 (br.s, 4H), 3.27-3.55 (br.s, 4H), 5.43 (s, 2H), 5.45 (s, 2H), 6.75 (t, J=7.3 Hz, 1H), 6.95 (t, J=7.1 Hz, 1H), 7.20 (d, J=6.9 Hz, 2H), 7.26-7.35 (m, 6H), 7.39 (t, J=7.3 Hz, 1H), 7.40 (d, J=7.1 Hz, 1H), 7.46 (t, J=7.3 Hz, 1H), 8.10 (s, 1H), 8.53 (br.s, 1H)

81d

2-[3-Benzyl-1-(2-cyanobenzyl)-2-oxo-4-piperazin-1-yl-2,3-dihydro-1H-imidazo[4.5-c]pyridin-7-yloxy]-benzamide trifluoroacetic acid salt

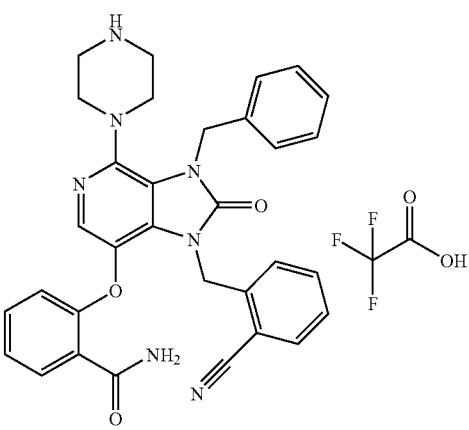

4-[3-Benzyl-7-(2-carbamoylphenoxy)-1-(2-cyanobenzyl)-2-oxo-2,3-dihydro-1H-imidazo[4.5-c]pyridin-4-yl]-piperazine-1-carboxylic acid t-butyl ester (0.023 g) was dissolved in dichloromethane and trifluoroacetic acid (1 mL). After stirring this at room temperature for two hours, then toluene (5 mL) was added, and this was concentrated under reduced pressure. The residue was purified by reverse phase high performance liquid chromatography to give the title compound (0.016 g).

MS m/e (ESI) 560.15 (M+H)⁺

EXAMPLE 82

3-(2-Butynyl-1-methyl-4-piperazin-1-yl-1,3-dihydroimidazo[4.5-c]pyridin-2-one

82a

Methyl-(3-nitro-pyridin-4-yl)amine

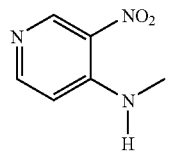

4-Ethoxy-3-nitropyridine (10.0 g) was dissolved in a 40% methanol solution of methyl amine (100 mL), and this was heated at 80° C. for 60 hours. The solution was cooled, ethyl acetate (500 mL) was added, and the organic layer was washed twice with 300 mL of water and once with 300 mL of saturated aqueous sodium chloride solution. This was then dried over anhydrous magnesium sulfate. The solution was filtered, and concentrated under reduced pressure to give the title compound (7.00 g).

¹H-NMR (CDCl₃)

3.06 (d, J=4.3 Hz, 3H), 6.72 (d, J=5.6 Hz, 1H), 8.11-8.21 (br.s, 1H), 8.23 (d, J=5.6 Hz, 1H), 9.22 (s, 1H)

82b

2-Chloro-N*4*-methylpyridine-3,4-diamine

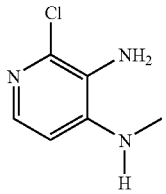

A solution of methyl-(3-nitro-pyridin-4-yl)amine (7.00 g) in concentrated hydrochloric acid (150 mL) was heated to 90° C. Tin(II) chloride dihydrate (52.2 g) was then added, and this was heated at 90° C. for 30 minutes. The reaction solution was cooled to 0° C., iced water (700 mL) was added, and this was stirred for 30 minutes. The solution was concentrated under reduced pressure, and then ammonia-saturated methanol solution (700 mL) was added to the residue, and this was stirred at 5° C. for 15 hours. The solvent was removed by concentration under reduced pressure. The residue was suspended in ethyl acetate (500 mL), and this was filtered through celite. The celite and the suspended material were washed five times with 250 mL of ethyl acetate, then the organic layers were combined, and this was concentrated under reduced pressure to give the title compound (7.22 g).

$^1$H-NMR (CDCl$_3$)

2.91 (d, J=4.5 Hz, 3H), 3.31-3.50 (br.s, 2H), 4.16-4.23 (br.s, 1H), 6.40 (d, J=5.8 Hz, 1H), 7.67 (d, J=5.8 Hz, 1H)

82c

4-Chloro-1-methyl-1,3-dihydroimidazo[4.5-c]pyridin-2-one

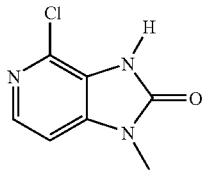

N,N'-disuccinimidyl carbonate (3.035 g) was added to a solution of 2-chloro-N*4*-methylpyridine-3,4-diamine (1.38 g) in acetonitrile (300 mL). The solution was stirred at room temperature for 48 hours, then additional N,N'-disuccinimidyl carbonate (3.035 g) was added, and this was heated at 50° C. for eight hours. The solvent was removed by concentration under reduced pressure, water (500 mL) was added, and this was extracted four times with dichloromethane (200 mL). The organic layers were combined and concentrated under reduced pressure. The residue was purified by silica gel chromatography, and the dichloromethane:ethyl acetate 1:1 fraction gave the title compound (1.038 g).

$^1$H-NMR (CDCl$_3$)

3.45 (s, 3H), 6.90 (d, J=5.7 Hz, 1H), 8.12 (d, J=5.7 Hz, 1H), 8.52-8.59 (s, 1H)

82d 3-(2-Butynyl)-4-chloro-1-methyl-1,3-dihydroimidazo[4.5-c]pyridin-2-one

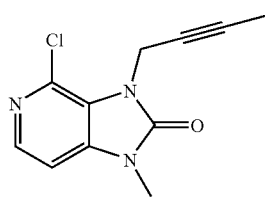

Potassium carbonate (1.17 g) and 1-bromo-2-butyne (0.742 mL) were added to a solution of 4-chloro-1-methyl-1,3-dihydroimidazo[4.5-c]pyridin-2-one in N,N-dimethylformamide (50 mL). This was then stirred at room temperature for 16 hours. Ethyl acetate (300 mL) and water (200 mL) were added, and the organic layer was washed twice with 200 mL of water and then once with 200 mL of saturated aqueous sodium chloride solution, then was dried over anhydrous magnesium sulfate. The organic layer was filtered and concentrated under reduced pressure, and the residue was purified by silica gel chromatography. The ethyl acetate:hexane 3:2 fraction gave the title compound (0.980 g).

$^1$H-NMR (CDCl$_3$)

1.79 (t, J=2.4 Hz, 3H), 3.45 (s, 3H), 4.81 (q, J=2.4 Hz, 2H), 6.90 (d, J=5.7 Hz, 1H), 8.11 (d, J=5.7 Hz, 1H)

82e 3-(2-Butynyl)-1-methyl-4-piperazin-1-yl-1,3-dihydroimidazo[4.5-c]pyridin-2-one

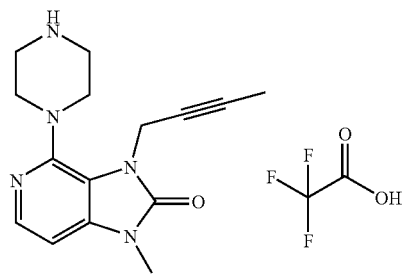

3-(2-butynyl)-4-chloro-1-methyl-1,3-dihydroimidazo[4.5-c]pyridin-2-one (0.041 g) and piperazine-1-carboxylic acid t-butyl ester (0.200 g) were heated at 175° C. for four hours under nitrogen atmosphere. Additional piperazine-1-carboxylic acid t-butyl ester (0.200 g) was then added, and this was heated at 175° C. for 16 hours. The residue was purified by reverse phase high performance liquid chromatography to give the title compound (0.032 g).

$^1$H-NMR (CD$_3$OD)

1.78 (t, J=2.4 Hz, 3H), 3.36 (s, 3H), 4.92 (q, J=2.4 Hz, 2H), 7.33 (d, J=5.7 Hz 1H), 8.20 (d, J=5.7 Hz, 1H)

MS m/e (ESI) 286.17 (M+H)$^+$

EXAMPLE 83

2-[3-(2-Butynyl)-1-methyl-2-oxo-4-piperazin-1-yl-2,3-dihydro-1H-imidazo[4.5-c]pyridin-7-ylox y]-benzamide trifluoroacetic acid salt

83a

4-[3-(2-Butynyl)-1-methyl-2-oxo-2,3-dihydro-1H-imidazo[4.5-c]pyridin-4-yl]-piperazine-1-carboxylic acid t-butyl ester

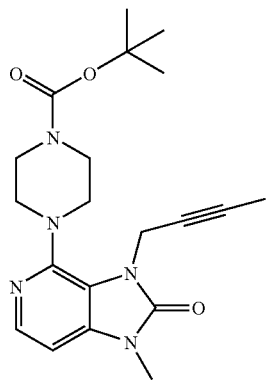

A solution of 3-(2-butynyl)-4-chloro-1-methyl-1,3-dihydroimidazo[4.5-c]pyridin-2-one (compound 82d) (0.865 g) and piperazine-1-carboxylic acid t-butyl ester (4.57 g) in 1-methyl-2-pyrrolidone (2 mL) was heated at 180° C. for two hours under a nitrogen atmosphere. Piperazine-1-carboxylic acid t-butyl ester (5.00 g) was then added again, and this was heated at 180° C. for five hours. Ethyl acetate (400 mL) and water (200 mL) were added, and the organic layer was washed twice with 200 mL of water and then once with 200 mL of saturated aqueous sodium chloride solution, and then was dried over anhydrous magnesium sulfate. The organic layer was filtered and concentrated under reduced pressure, and the residue was purified by silica gel chromatography. The ethyl acetate:hexane 3:2 fraction gave the title compound (0.447 g).

$^1$H-NMR (CDCl$_3$)

δ 1.50 (s, 9H), 1.78 (t, J=2.4 Hz, 3H), 3.10-3.17 (m, 4H), 3.40 (s, 3H), 3.59-3.60 (m, 4H), 4.92 (q, J=2.4 Hz, 2H), 6.68 (d, J=5.7 Hz, 1H), 8.08 (d, J=5.7 Hz, 1H)

83b

4-[7-Bromo-3-(2-butynyl)-1-methyl-2-oxo-2,3-dihydro-1H-imidazo[4.5-c]pyridin-4-yl]-piperazine-1-carboxylic acid t-butyl ester

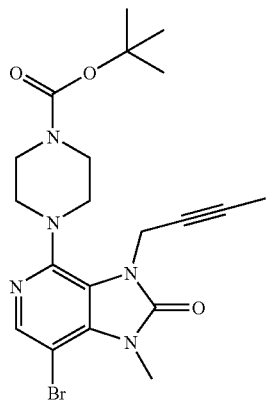

Sodium bicarbonate (0.146 g) and N-bromosuccinimide (0.288 g) were added to a solution of 4-[3-(2-butynyl)-1-methyl-2-oxo-2,3-dihydro-1H-imidazo[4.5-c]pyridin-4-yl]-piperazine-1-carboxylic acid t-butyl ester (0.447 g) in N,N-dimethylformamide (20 mL). This was then stirred at room temperature for 60 hours. Sodium bicarbonate (0.219 g) and N-bromosuccinimide (0.432 g) were added again, and this was stirred at room temperature for 15 hours. Ethyl acetate (100 mL) and water (50 mL) were then added, and the organic layer was washed twice with 50 mL of water and then once with 50 mL of saturated aqueous sodium chloride solution, then was dried over anhydrous magnesium sulfate, filtered, and concentrated under reduced pressure. The residue was purified by silica gel chromatography, and the hexane:ethyl acetate 1:1 fraction gave the title compound (0.201 g).

$^1$H-NMR (CDCl$_3$)

1.49 (s, 9H), 1.77 (t, J=2.4 Hz, 3H), 3.05-3.02 (m, 4H), 3.38-3.72 (br.s, 4H), 3.75 (s, 3H), 4.95 (q, J=2.4 Hz, 2H), 8.06 (s, 1H)

83c

2-[3-(2-Butynyl)-1-methyl-2-oxo-4-piperazin-1-yl-2,3-dihydro-1H-imidazo[4.5-c]pyridin-7-ylox y]-benzamide trifluoroacetic acid salt

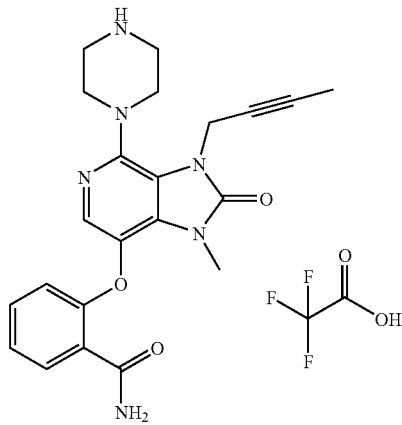

Salicylamide (0.030 g), cesium carbonate (0.071 g), 2,2,6,6-tetramethyl-3,5-heptanedione (0.003 mL), and copper(I) chloride (0.006 g) were added to a solution of 4-[7-bromo-3-(2-butynyl)-1-methyl-2-oxo-2,3-dihydro-1H-imidazo[4.5-c]pyridin-4-yl]-piperazine-1-carboxylic acid t-butyl ester (0.050 g) in 1-methyl-2-pyrrolidone (1 mL). This was heated under nitrogen atmosphere at 130° C. for 14 hours. The reaction solution was cooled, dichloromethane (2 mL) and trifluoroacetic acid (3 mL) were added, and this was stirred for two hours. The solvent was removed by concentration under reduced pressure, and the residue was purified by reverse phase high performance liquid chromatography to give the title compound (0.007 g).

MS m/e (ESI) 421.17 (M+H)$^+$

EXAMPLE 84

7-(2-Butynyl)-9-methyl-6-(piperazin-1-yl)-7,9-dihydropurin-8-thione trifluoroacetic acid salt

84a 4-(5-Amino-6-methylamino-pyrimidin-4-yl)piperazine-1-carboxylic acid t-butyl ester

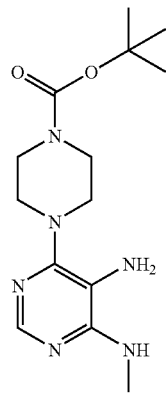

4-(6-Chloro-5-nitro-pyrimidin-4-yl)piperazine-1-carboxylic acid t-butyl ester (compound 61a) (5.0 g) was dissolved in acetonitrile (50 mL), and then methylamine (40%, methanol solution) (2.83 mL) was added to this solution. After stirring this reaction solution at room temperature for 17 hours, water (150 mL) was added. The reaction solution was stirred at room temperature for one hour, and then the precipitate was collected by filtration. The obtained yellow solid was washed with water and hexane to give a yellow solid (4.05 g). 1 g of the obtained yellow solid was dissolved in ethanol (20 mL). 10% palladium on carbon powder (wet) (200 mg) was then added to this solution. The reaction solution was stirred at room temperature for 15 hours under a hydrogen atmosphere. The insoluble substances were removed by filtration, and the obtained filtrate was concentrated under reduced pressure to give the title compound (920 mg).

$^1$H-NMR (CDCl$_3$)

δ 1.48 (s, 9H), 3.05 (d, J=4.8 Hz, 3H), 3.07 (m, 4H), 3.55 (m, 4H), 4.48 (br.s, 2H), 8.15 (s, 1H)

84b

4-[5-(2-Butynylamino)-6-methylamino-pyrimidine-4-yl]piperazine-1-carboxylic acid t-butyl ester

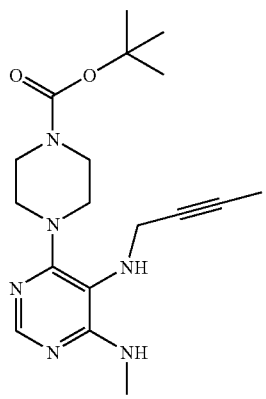

4-(5-Amino-6-methylamino-pyrimidin-4-yl)piperazine-1-carboxylic acid t-butyl ester (200 mg) was dissolved in N,N-dimethylformamide (5.0 mL), and then 1-bromo-2-butyne (57 μL) and anhydrous potassium carbonate (107 mg) were added to this solution. The reaction solution was stirred at room temperature for 20 hours, and then poured into a saturated aqueous ammonium chloride solution. It was then extracted with ethyl acetate, and the obtained organic layer was washed with water and saturated brine. The obtained organic layer was dried over anhydrous magnesium sulfate, and concentrated under reduced pressure. The residue was purified by silica gel column chromatography to give the title compound (118 mg).

$^1$H-NMR (CDCl$_3$)

δ 1.46 (s, 9H), 1.80 (t, J=2.4 Hz, 3H), 2.99 (d, J=4.8 Hz, 3H), 3.16 (m, 4H), 3.53 (m, 4H), 3.60 (br.d, J=2.4 Hz, 2H), 4.48 (br.d, J=4.8 Hz, 1H), 8.18 (s, 1H)

84c 7-(2-Butynyl)-9-methyl-6-(piperazin-1-yl)-7,9-dihydropurin-8-thione trifluoroacetic acid salt

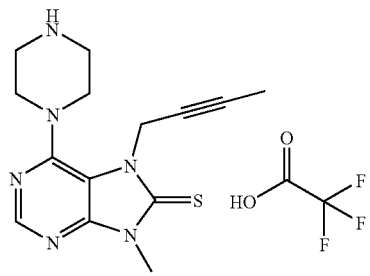

4-[5-(2-Butynylamino)-6-methylamino-pyrimidin-4-yl]piperazine-1-carboxylic acid t-butyl ester (18 mg) was dissolved in acetonitrile (0.5 mL), and then thiocarbonyldiimidazole (100 mg) was added to this solution. The reaction solution was stirred at 80° C. for 48 hours, and then 1 N hydrochloric acid was added to the reaction solution. This was extracted with ethyl acetate, and the obtained organic layer was concentrated under reduced pressure. The residue was purified by silica gel column chromatography (ethyl acetate:hexane=3:7). The obtained solid was dissolved in trifluoroacetic acid, and this solution was stirred at room temperature for five minutes, and then concentrated. The residue was purified by reverse phase high performance liquid chromatography to give the title compound (13.05 mg).

$^1$H-NMR (CD$_3$OD)

δ 1.85 (t, J=2.4 Hz, 3H), 3.52 (m, 4H), 3.70 (m, 4H), 3.76 (s, 3H), 5.21 (q, J=2.4 Hz, 2H), 8.53 (s, 1H)

MS m/e (ESI) 303(M+H)$^+$

EXPERIMENT 1

Control Compound (NVP DPP728)

The following compound, described in U.S. Pat. No. 6,011,155, was synthesized according to the Examples.

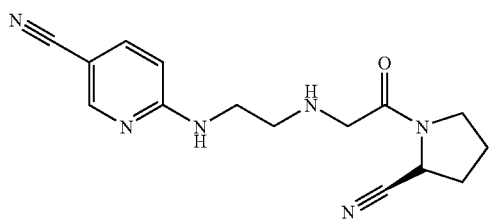

Measurement of DPPIV-Inhibiting Activity (In Vitro Experiment)

DPP-IV obtained from pig kidney was dissolved in a reaction buffer (50 mM Tris-HCl pH7.4, 0.1% BSA) at 10 mU/mL, and 110 μL of this was used. 15 μL of the drug obtained from the aforementioned Examples was added, and this was incubated at room temperature for 20 minutes, and then 25 μL of a 2 mM solution of Gly-Pro-p-nitroanilide (final concentration 0.33 mM) was added to start the enzymatic reaction. The reaction time was 20 minutes, and 1 N phosphoric acid solution (25 μL) was added to stop the reaction. The absorbance of this material at 405 nm was measured, the enzyme inhibition rate was determined, and the $IC_{50}$ was calculated. The results are shown in Table 1.

TABLE 1

| Example No. | $IC_{50}$ (μM) |
| --- | --- |
| 1 | 0.240 |
| 2 | 0.0864 |
| 3 | 0.325 |
| 4 | 0.334 |
| 5 | 0.172 |
| 6 | 0.450 |
| 7 | 0.199 |
| 8 | 1.16 |
| 9 | 0.214 |
| 10 | 0.251 |
| 11 | 0.179 |
| 12 | 0.0474 |
| 13 | 0.0247 |
| 14 | 0.124 |
| 15 | 0.319 |
| 16 | 0.364 |
| 17 | 0.263 |
| 18 | 0.972 |
| 19 | 5.41 |
| 20 | 0.642 |
| 21 | 2.45 |
| 27 | 3.14 |
| 28 | 89.5 |
| 29 | 0.00292 |
| 30 | 0.132 |
| 31 | 0.259 |
| 32 | 0.212 |
| 33 | 0.163 |
| 34 | 0.0148 |
| 35 | 0.0266 |
| 36 | 0.0807 |
| 37 | 0.149 |
| 38 | 0.150 |
| 39 | 0.0323 |
| 40 | 0.0896 |
| 41 | 0.0917 |
| 42 | 0.0425 |
| 43 | 0.0678 |
| 44 | 0.132 |
| 45 | 0.130 |
| 46 | 0.0426 |
| 47 | 0.167 |
| 48 | 0.0716 |
| 49 | 0.0400 |

TABLE 1-continued

| Example No. | $IC_{50}$ (μM) |
| --- | --- |
| 50 | 0.00365 |
| 51 | 0.130 |
| 52 | 0.175 |
| 53 | 1.37 |
| 54 | 0.0888 |
| 55 | 0.0372 |
| 56 | 0.0964 |
| 57 | 0.0775 |
| 58 | 0.0156 |
| 59 | 0.119 |
| 60 | 0.119 |
| 61 | 0.0619 |
| 62 | 0.139 |
| 63 | 0.146 |
| 64 | 0.0325 |
| 65 | 0.0167 |
| 66 | 0.0593 |
| 67 | 0.0498 |
| 68 | 0.187 |
| 69 | 0.224 |
| 70 | 0.0948 |
| 71 | 0.260 |
| 72 | 0.141 |
| 73 | 0.0484 |
| 74 | 0.0140 |
| 75 | 0.921 |
| 76 | 1.06 |
| 77 | 8.13 |
| 78 | 3.80 |
| 79 | 0.0042 |
| 80 | 3.01 |
| 81 | 0.409 |
| 82 | 5.23 |
| 83 | 1.13 |
| 84 | 13.6 |
| Control compound | 226 |

EXPERIMENT 2

Effects on Glucose Tolerance in Normal Mice (In Vivo Experiment)

Animals: Male C57BL/6N mice (purchased from Japan Charles River)

Methods:

Preparation and Administration of Test Compounds

The test compounds were suspended in a 0.5% methylcellulose (MC) solution at the doses indicated below in Table 2. These test compounds and the NVP DPP728 (U.S. Pat. No. 6,011,155) suspension, or the 0.5% MC solution (the solvent control group), were administered orally at a dose of 10 mL/kg. 30 minutes later, a glucose solution was orally administered at a dose of 10 mL/kg. Glucose was orally administered at a dose of 2 g/kg.

[Blood Collection and Measurement of Blood Glucose Level]

The tail vain of unanesthetized mice was cut with a razor blade to cause a small amount of bleeding immediately before administering the test substances or NVP DPP728, and immediately before, as well as 30, 60, and 120 minutes after, administration of the glucose solution. 10 μL of blood was collected, and this was mixed immediately with 0.6 M perchloric acid (140 μL). Glucose present in the supernatant obtained by centrifugation (1500 g, 10 minutes, 4° C., refrigerated centrifuge GS-6KR, Beckman) was measured using Glucose CII Test Wako (Wako Pure Chemicals).

Results: In each of the groups to which 0.5% MC solution, NVP DPP728, and the test compounds were administered, the area under the curve of blood glucose vs. time was calculated over 0 to 120 minutes from the time of glucose administration ($AUC_{0-120}$). Defining the $AUC_{0-120}$ for the 0.5% MC solution-administered group as 100%, and the $AUC_{0-120}$ for the NVP DPP728 (10 mg/kg)-administered group as 0%, the degree of improvement in glucose tolerance due to the test compound was calculated by the following equation:

Degree of improvement in glucose tolerance (%)=
($AUC_{0-120}$ of the test compound–$AUC_{0-120}$ of the NVP DPP728 (10 mg/kg)-administered group)/
($AUC_{0-120}$ of the 0.5% MC solution-administered group–$AUC_{0-120}$ of the NVP DPP728 (10 mg/kg)-administered group)×100

The lower the % value, the better the degree of improvement in glucose tolerance.

Table 2 shows the results (effects on glucose tolerance in normal mice).

TABLE 2

| Specimen (mg/kg) | Degree of improvement in glucose tolerance (%) |
| --- | --- |
| Example 1(1) | 19.8 |
| Example 7(1) | 19.8 |
| Example 10(1) | 17.3 |
| Example 13(1) | 33.5 |
| Example 15(1) | 46 |
| Example 46(1) | 37 |
| Example 47(1) | 11.6 |
| Example 48(1) | 37.4 |
| Example 51(1) | 59.3 |
| Example 52(1) | 29.7 |
| Example 54(1) | 24.4 |
| Example 56(1) | 11.3 |
| Example 61(1) | 9.4 |
| Example 64(1) | −11.4 |
| Example 65(1) | 9.5 |
| Example 69(1) | 44.1 |

Compounds with clear effects on glucose tolerance in normal mice were discovered among the novel fused 1,3-dihydro-imidazole ring compounds of this invention, at orally administered doses of 1 to 10 (mg/kg) using the above-mentioned in vivo experiment.

INDUSTRIAL APPLICABILITY

This invention was able to provide fused 1,3-dihydro-imidazole ring compounds that show DPPIV-inhibiting activity.

Therefore, the fused 1,3-dihydroimidazole ring compounds of this invention are useful as therapeutic and preventive agents, such as therapeutic agents for diabetes, obesity, hyperlipidemia, AIDS, osteoporosis, gastrointestinal disorder, angiogenesis, and infertility, and as anti-inflammatory agents, anti-allergic agents, immunoregulatory agents, hormone regulatory agents, anti-rheumatic agents, and therapeutic agents for cancer.

To confirm their drug efficacy when orally administered, examinations were carried out using improvement in glucose tolerance as the indicator. Their oral effectiveness was confirmed, and their usefulness as drugs was discovered.

The invention claimed is:

1. A compound represented by the formula (I), or a salt thereof,

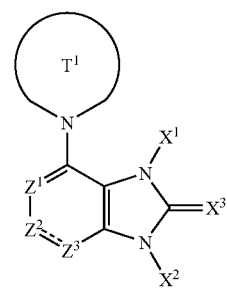

(I)

[wherein, $T^1$ is a piperazin-1-yl group, a 3-amino-piperidin-1-yl group, or a 3-methylamino-piperidin-1-yl group;

$X^3$ denotes an oxygen atom or a sulfur atom, $X^1$ denotes a $C_{1-6}$ alkyl group which may have substitutents, a $C_{2-6}$ alkenyl group which may have substitutents, a $C_{2-6}$ alkynyl group which may have substitutents, a $C_{6-10}$ aryl group which may have substitutents, a 5 to 10-membered heteroaryl group which may have substitutents, a $C_{6-10}$ aryl $C_{1-6}$ alkyl group which may have substitutents, or a 5 to 10-membered heteroaryl $C_{1-6}$ alkyl group which may have substitutents;

$Z^1$ denotes a nitrogen atom;

$Z^2$ denotes a group of the formula —$CR^1$— and $Z^3$ denotes a nitrogen atom;

in formula (I), the following formula

denotes a double bond;

$R^1$ and $X^2$ each independently denote a hydrogen atom, a 4 to 8-membered heterocyclic group which may have substitutents, or a group represented by the formula —$A^0$—$A^1$—$A^2$;

$A^0$ denotes a single bond, or a $C_{1-6}$ alkylene group that may have 1 to 3 substituents selected from the following substituent group A;

$A^1$ denotes a single bond, oxygen atom, sulfur atom, a sulfinyl group, a sulfonyl group, a carbonyl group, a group of the formula —O—CO, a group of the formula —CO—O—, a group of the formula —$NR^4$—, a group of the formula —CO—$NR^4$—, a group of the formula $NR^4$—CO—, a group of the formula —$SO_2$—$NR^4$—, or a group of the formula —$NR^4$—$SO_2$—;

$A^2$ and $R^4$ each independently denote a hydrogen atom, a cyano group, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5 to 10-membered heteroaryl group, a 4 to 8-membered heterocyclic group, or a $C_{6-10}$ aryl $C_{1-6}$ alkyl group;

however, $A^2$ and $R^A$ each independently may have 1 to 3 substituents selected from the substituent group A described below:

<Substituent group A> substituent group A refers to a group consisting of: a hydroxyl group, a mercapto group, a cyano group, a halogen atom, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5 to 10-membered heteroaryl group, a 4 to 8-membered heterocyclic group, a $C_{1-6}$ alkoxy group, a $C_{1-6}$ alkylthio group, a group of the formula —$NR^{B4}$—$R^{B5}$ (where $R^{B4}$ and $R^{B5}$ denote hydrogen atoms or $C_{1-6}$ alkyl groups), a group of the formula —CO—$R^{B6}$ (where $R^{B6}$ denotes a 1-pyrrolidinyl group, a 1-morpholinyl group, a 1-piperazinyl group, or a 1-piperidyl group), and a group of the formula —CO—$R^B$—$R^{B2}$ (where $R^B$ denotes a single bond, an oxygen atom, or a group represented by the formula —$NR^{B3}$—; $R^{B2}$ and $R^{B3}$ each independently denote a hydrogen atom, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5 to 10-membered heteroaryl group, a $C_{6-10}$ aryl $C_{1-6}$ alkyl group, or a 5 to 10-membered heteroaryl $C_{1-6}$ alkyl group)].

2. A compound represented by the formula (II), or a salt thereof,

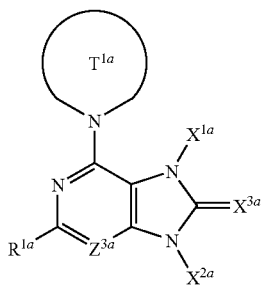

(II)

[wherein, $Z^{3a}$ denotes a nitrogen atom;

$X^{3a}$ denotes an oxygen atom or a sulfur atom;

$T^{1a}$ is a piperazin-1-yl group, a 3-amino-piperidin-1-yl group, or a 3-methylamino-piperidin-1-yl group;

$X^{1a}$ denotes a hydrogen atom, a $C_{2-6}$ alkenyl group, a $C_{2-6}$ alkynyl group, or a benzyl group;

$R^{1a}$ denotes a hydrogen atom, a halogen atom, a $C_{1-6}$ alkyl group, a cyano group, or a group represented by the formula —$A^{0a}$—$A^{1a}$;

$A^{0a}$ denotes an oxygen atom, a sulfur atom, or a group represented by the formula —$NA^{2a}$;

$A^{1a}$ denotes a hydrogen atom, a $C_{1-6}$ alkyl group, a $C_{2-6}$ alkenyl group, a $C_{2-6}$ alkynyl group, a phenyl group, a cyanophenyl group, a carbamoylphenyl group, a benzyl group, a pyridylmethyl group, or a pyridyl group;

$A^{2a}$ denotes a hydrogen atom, or a $C_{1-6}$ alkyl group;

$X^{2a}$ denotes a hydrogen atom, a $C_{2-6}$ alkenyl group, a $C_{2-6}$ alkynyl group, a cyclohexenyl group, a 1H-pyridin-2-on-yl group, a 1-methyl-1H-pyridin-2-on-yl group, a $C_{1-6}$ alkyl group that may have a group selected from substituent group B described below, a phenyl group that may have a group selected from substituent group B described below, a 5 or 6-membered heteroaryl group that may have a group selected from substituent group B described below, a phenyl $C_{1-6}$ alkyl group that may have a group selected from substituent group B described below, or a pyridyl $C_{1-6}$ alkyl group that may have a group selected from substituent group B described below:

<Substituent group B> substituent group B refers to a group consisting of a chlorine atom, a bromine atom, a cyano group, a $C_{1-6}$ alkyl group, a $C_{2-6}$ alkenyl group, a $C_{2-6}$ alkynyl group, a $C_{3-8}$ cycloalkyl group, a $C_{1-6}$ alkoxy group, a carbamoyl group, a carboxyl group, and a $C_{1-6}$ alkoxycarbonyl group].

3. A compound represented by the formula (III), or a salt thereof,

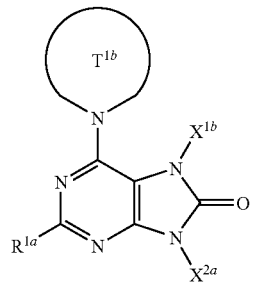

(III)

[wherein, $T^{1b}$ stands for a piperazin-1-yl group, a 3-amino-piperidin-1-yl group, or a 3-methylamino-piperidin-1-yl group;

$X^{1b}$ denotes a 2-pentynyl group, a 2-butynyl group, a 3-methyl-2-butenyl group, a 2-butenyl group, or a benzyl group; and $R^{1a}$ and $X^{2a}$ have the same meaning as $R^{1a}$ and $X^{2a}$ of claim 2 defined above].

4. The compound of claim 2 or 3, or a salt thereof, wherein $R^{1a}$ is a hydrogen atom, a chlorine atom, a cyano group, a methoxy group, an ethoxy group, an i-propyloxy group, a methylthio group, an allyloxy group, a 2-butynyloxy group, a phenyloxy group, a cyanophenyloxy group, a carbamoylphenyloxy group, a phenylmethyloxy group, a (phenylmethyl)amino group, a pyridylmethyloxy group, a pyridyloxy group, an amino group, a methylamino group, a dimethylamino group, or a diethylamino group.

5. The compound of claim 2 or 3, or a salt thereof, wherein $R^{1a}$ is a hydrogen atom, a methoxy group, an ethoxy group, an i-propyloxy group, a 2-cyanophenyloxy group, or a 2-carbamoylphenyloxy group.

6. The compound of claim 2 or 3, or a salt or a hydrate thereof, wherein $X^{2a}$ is a hydrogen atom, a methyl group, an ethyl group, an n-propyl group, a 2-methylpropyl group, a group represented by the formula —$CH_2$—$R^{10}$ (where $R^{10}$ denotes a carbamoyl group, a carboxyl group, a methoxycarbonyl group, a cyano group, a cyclopropyl group, or a methoxy group), a 3-cyanopropyl group, an allyl group, a 2-propionyl group, a 2-butynyl group, a 2-methyl-2-propenyl group, a 2-cyclohexynyl group, a chloropyridyl group, a methoxypyridyl group, a methoxypyrimidyl group, a pyridyl group, a furyl group, a thienyl group, a pyridylmethyl group, a 1H-pyridin-2-on-5-yl group, a 1-methyl-1H-pyridin-2-on-5-yl group, a phenyl group that may have a group selected from substituent group Y described below, a benzyl group that may have a group selected from substituent group Y described below, or a phenethyl group that may have a group selected from substituent group Y described below:

substituent group Y is a group consisting of: a chlorine atom, a bromine atom, a methoxy group, a cyano group, a vinyl group, and a methyl group.

7. The compound of claim 2 or 3, or a salt thereof, wherein $X^{2a}$ is a methyl group, n-propyl group, allyl group, 2-propynyl group, 2-butynyl group, cyclopropylmethyl group, phenyl group, 3-pyridyl group, 3-furyl group, 3-thienyl group, 2-methoxy-5-pyrimidinyl group, 2-methoxy-5-pyridyl group, 2-chloro-4-pyridyl group, or 1H-pyridin-2-on-5-yl group.

8. A pharmaceutical composition comprising the compound of claim 1, or a salt thereof, and an adjuvant for formulation.

* * * * *